(12) United States Patent
Vogeley

(10) Patent No.: US 7,312,554 B2
(45) Date of Patent: Dec. 25, 2007

(54) PIEZOELECTRIC DEVICES AND METHODS AND CIRCUITS FOR DRIVING SAME

(75) Inventor: James Vogeley, Yorktown, VA (US)

(73) Assignee: Adaptivenergy, LLC, Hampton, VA (US)

( * ) Notice: Subject to any disclaimer, the term of this patent is extended or adjusted under 35 U.S.C. 154(b) by 104 days.

(21) Appl. No.: 10/815,975

(22) Filed: Apr. 2, 2004

(65) Prior Publication Data

US 2005/0219302 A1 Oct. 6, 2005

(51) Int. Cl.
*H01L 41/09* (2006.01)

(52) U.S. Cl. .................................. 310/317; 310/316.01

(58) Field of Classification Search .......... 310/316.01, 310/317
See application file for complete search history.

(56) References Cited

U.S. PATENT DOCUMENTS

| | | | |
|---|---|---|---|
| 3,500,799 A | 3/1970 | Benson | |
| 3,936,342 A | 2/1976 | Matsubara et al. | |
| 4,034,780 A | 7/1977 | Horvath | |
| 4,095,615 A | 6/1978 | Ramsauer | |
| 4,514,742 A | 4/1985 | Suga et al. | 347/85 |
| 4,853,579 A * | 8/1989 | Kawasaki et al. | 310/116 |
| 4,859,530 A | 8/1989 | Roark et al. | |
| 4,939,405 A * | 7/1990 | Okuyama et al. | 310/330 |
| 5,021,700 A | 6/1991 | Takahashi et al. | |
| 5,049,421 A | 9/1991 | Kosh | |
| 5,070,848 A * | 12/1991 | Mitsuyasu | 123/506 |
| 5,084,345 A | 1/1992 | Manos | |
| 5,130,598 A | 7/1992 | Verheyen et al. | |
| 5,195,046 A * | 3/1993 | Gerardi et al. | 702/35 |
| 5,271,724 A | 12/1993 | van Lintel | |
| 5,471,721 A | 12/1995 | Haertling | |
| 5,517,845 A * | 5/1996 | Yamashita et al. | 73/1.38 |
| 5,632,841 A | 5/1997 | Hellbaum et al. | |

(Continued)

FOREIGN PATENT DOCUMENTS

JP 57-211562 * 12/1982

(Continued)

OTHER PUBLICATIONS

International Search Report and Written Opinion mailed Nov. 16, 2006 in corresponding PCT application No. PCT/US05/11344.

(Continued)

*Primary Examiner*—Thomas M. Dougherty
(74) *Attorney, Agent, or Firm*—Nixon & Vanderhye, P.C.

(57) ABSTRACT

A drive circuit (18) senses a parameter of a piezoelectric actuator (14) operating in a device (10) and adjusts a drive signal of the piezoelectric actuator in accordance with the parameter. The drive circuit comprises a controller (100) which controls a drive signal applied to the piezoelectric actuator (14); a feedback monitor (122) which obtains a feedback signal from the piezoelectric actuator while the piezoelectric actuator works; and, a processor (116) which uses the feedback signal to determine the parameter of the piezoelectric actuator. In one example mode, the parameter of the piezoelectric actuator which is determined by the piezoelectric actuator drive circuit is the capacitance or dielectric constant of the piezoelectric actuator. In other example modes, the parameter of the piezoelectric actuator which is determined by the piezoelectric actuator drive circuit is impedance or resonant frequency of the piezoelectric actuator.

26 Claims, 47 Drawing Sheets

U.S. PATENT DOCUMENTS

| | | |
|---|---|---|
| 5,759,015 A | 6/1998 | van Lintel et al. |
| 5,816,780 A | 10/1998 | Bishop et al. ............... 417/322 |
| 5,849,125 A | 12/1998 | Clark |
| 5,876,187 A | 3/1999 | Afromowitz et al. |
| 5,892,315 A | 4/1999 | Gipson et al. |
| 5,945,768 A | 8/1999 | Treu, Jr. |
| 6,033,191 A | 3/2000 | Kamper et al. |
| 6,042,345 A | 3/2000 | Bishop et al. |
| 6,060,811 A | 5/2000 | Fox et al. |
| 6,071,087 A | 6/2000 | Jalink, Jr. et al. |
| 6,071,088 A | 6/2000 | Bishop et al. |
| 6,074,178 A | 6/2000 | Bishop et al. ............... 417/322 |
| 6,104,127 A | 8/2000 | Kameyama et al. |
| 6,109,889 A | 8/2000 | Zengerle et al. |
| 6,121,714 A | 9/2000 | Atsuta |
| 6,162,313 A | 12/2000 | Bansemir et al. |
| 6,179,584 B1 | 1/2001 | Howitz et al. |
| 6,213,735 B1 | 4/2001 | Henco et al. |
| 6,227,809 B1 | 5/2001 | Forster et al. |
| 6,227,824 B1 | 5/2001 | Stehr |
| 6,229,245 B1* | 5/2001 | Kitani .................... 310/316.02 |
| 6,246,152 B1* | 6/2001 | Fontanella et al. ......... 310/317 |
| 6,252,512 B1 | 6/2001 | Riley |
| 6,411,009 B2* | 6/2002 | Jaenker ................. 310/316.01 |
| 6,659,978 B1* | 12/2003 | Kasuga et al. ............... 604/151 |
| 6,716,002 B2 | 4/2004 | Higashino ................ 417/413.2 |
| 6,943,785 B2 | 9/2005 | Chou et al. |
| 6,950,640 B2* | 9/2005 | Ikeda et al. .................. 455/214 |
| 6,969,941 B1* | 11/2005 | Kapps et al. .......... 310/316.01 |
| 6,993,812 B2* | 2/2006 | Takahashi .................. 29/25.35 |
| 7,056,096 B2 | 6/2006 | Takagi et al. |
| 7,059,836 B2 | 6/2006 | Takagi et al. |
| 7,126,822 B2 | 10/2006 | Hu et al. |
| 2002/0140441 A1* | 10/2002 | Raffalt et al. ................ 324/682 |
| 2002/0185938 A1* | 12/2002 | Ikeda et al. .................. 310/348 |
| 2003/0146956 A1* | 8/2003 | Takahashi ..................... 347/71 |
| 2004/0000843 A1 | 1/2004 | East |
| 2004/0018100 A1* | 1/2004 | Takagi et al. ............... 417/322 |
| 2004/0021398 A1 | 2/2004 | East |
| 2005/0186117 A1* | 8/2005 | Uchiyama et al. ............. 422/91 |
| 2005/0244288 A1* | 11/2005 | O'Neill .................... 417/413.2 |

FOREIGN PATENT DOCUMENTS

| | | | |
|---|---|---|---|
| JP | 62-150051 | * | 7/1987 |
| JP | 62-186077 | * | 8/1987 |
| JP | 02-248671 | * | 10/1990 |
| JP | 03-015674 | * | 1/1991 |
| JP | 03-168373 | * | 7/1991 |
| JP | 06-117377 | * | 4/1994 |
| JP | 2002-136158 A | | 10/2002 |
| WO | 87/07218 | | 12/1987 |

OTHER PUBLICATIONS

International Preliminary Report on Patentability mailed Oct. 12, 2006 in corresponding PCT application No. PCT/US05/11344.

Office Action mailed Jun. 13, 2007 in U.S. Pat. Appl. No. 10/815,999.

International Search Report and Written Opinion mailed May 16, 2007 in PCT application PCT/US05/11342.

International Search Report and Written Opinion mailed May 18, 2007 in PCT application PCT/US05/11579.

* cited by examiner

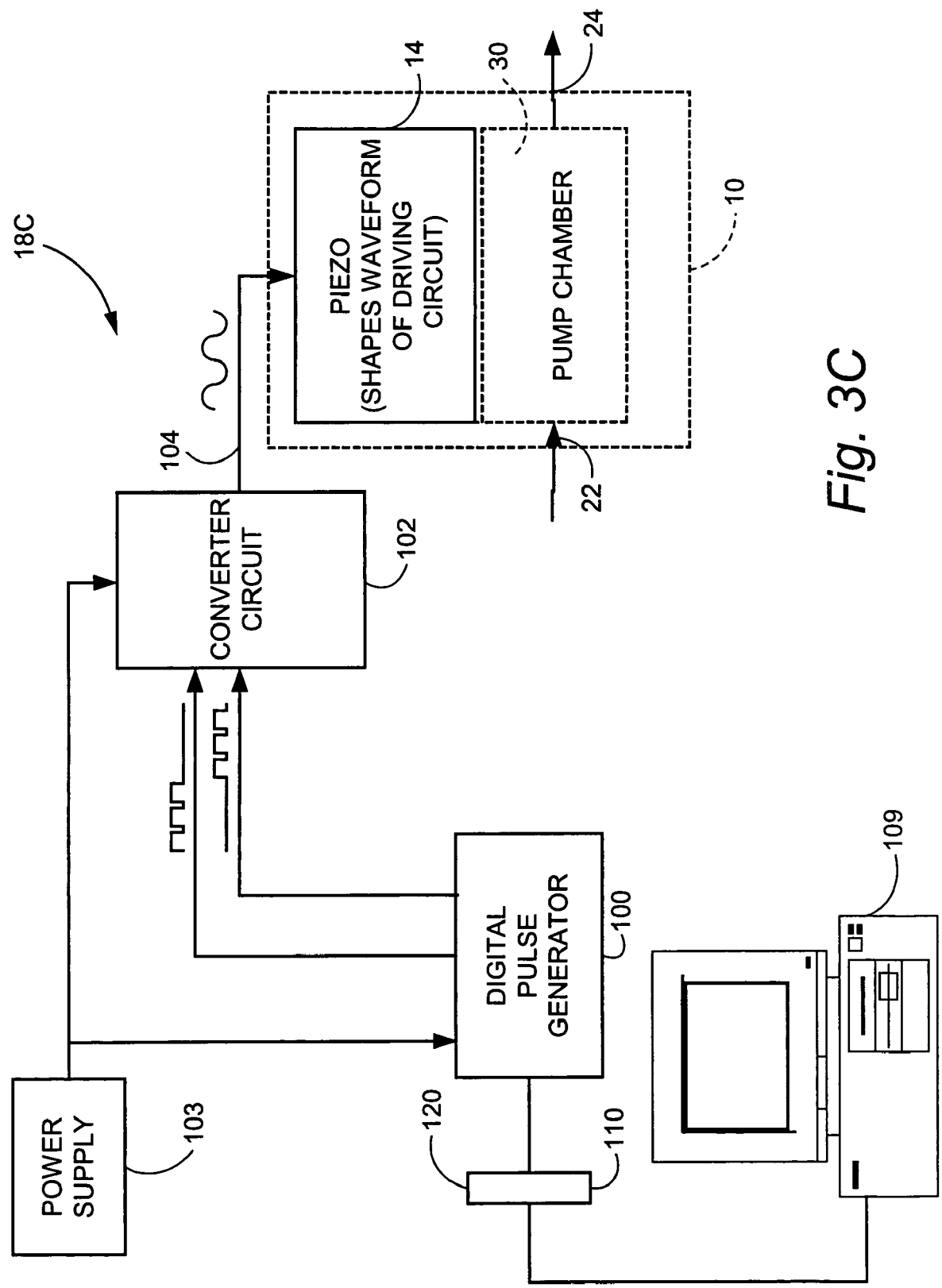

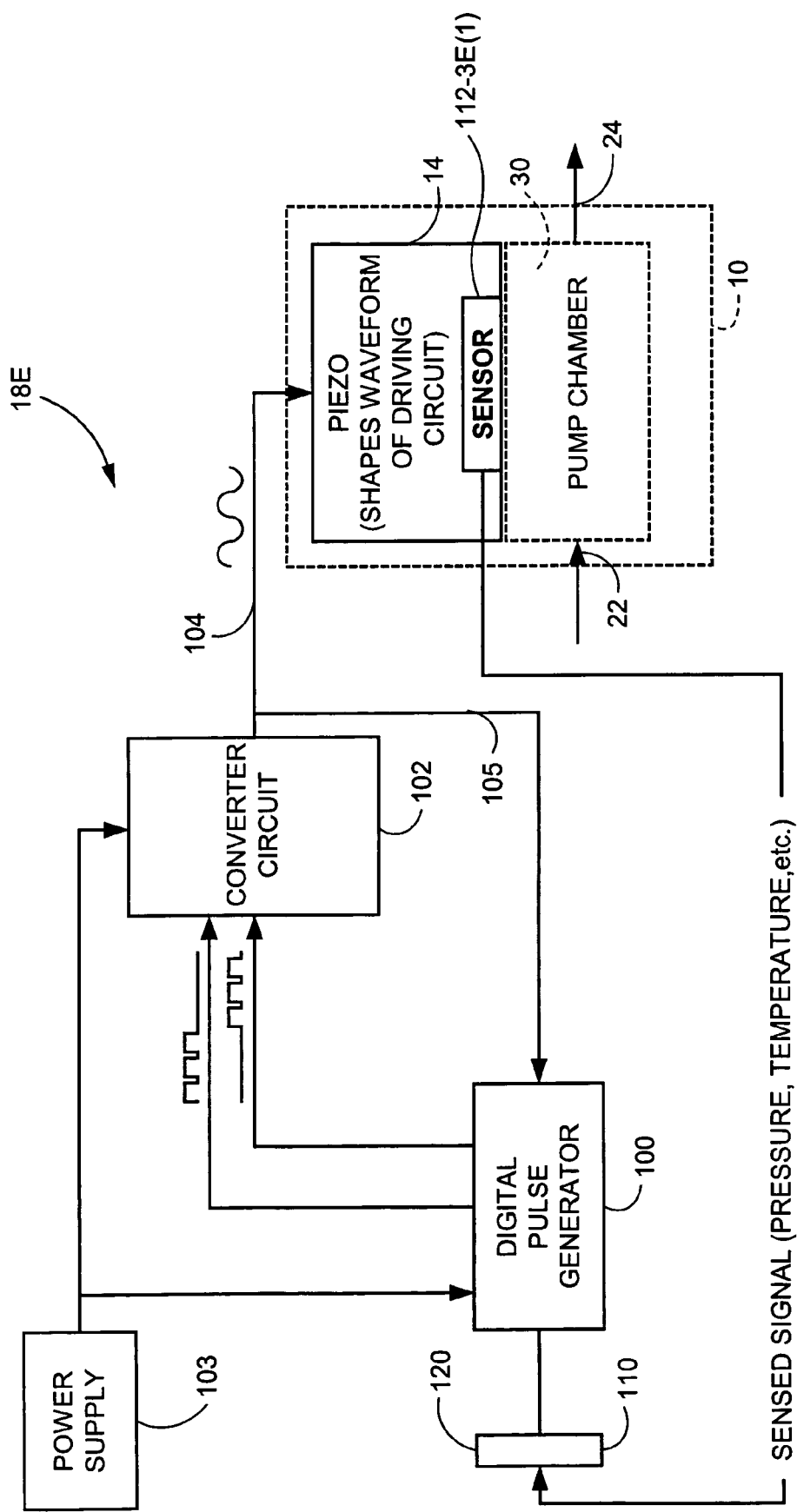
Fig. 3E(1)

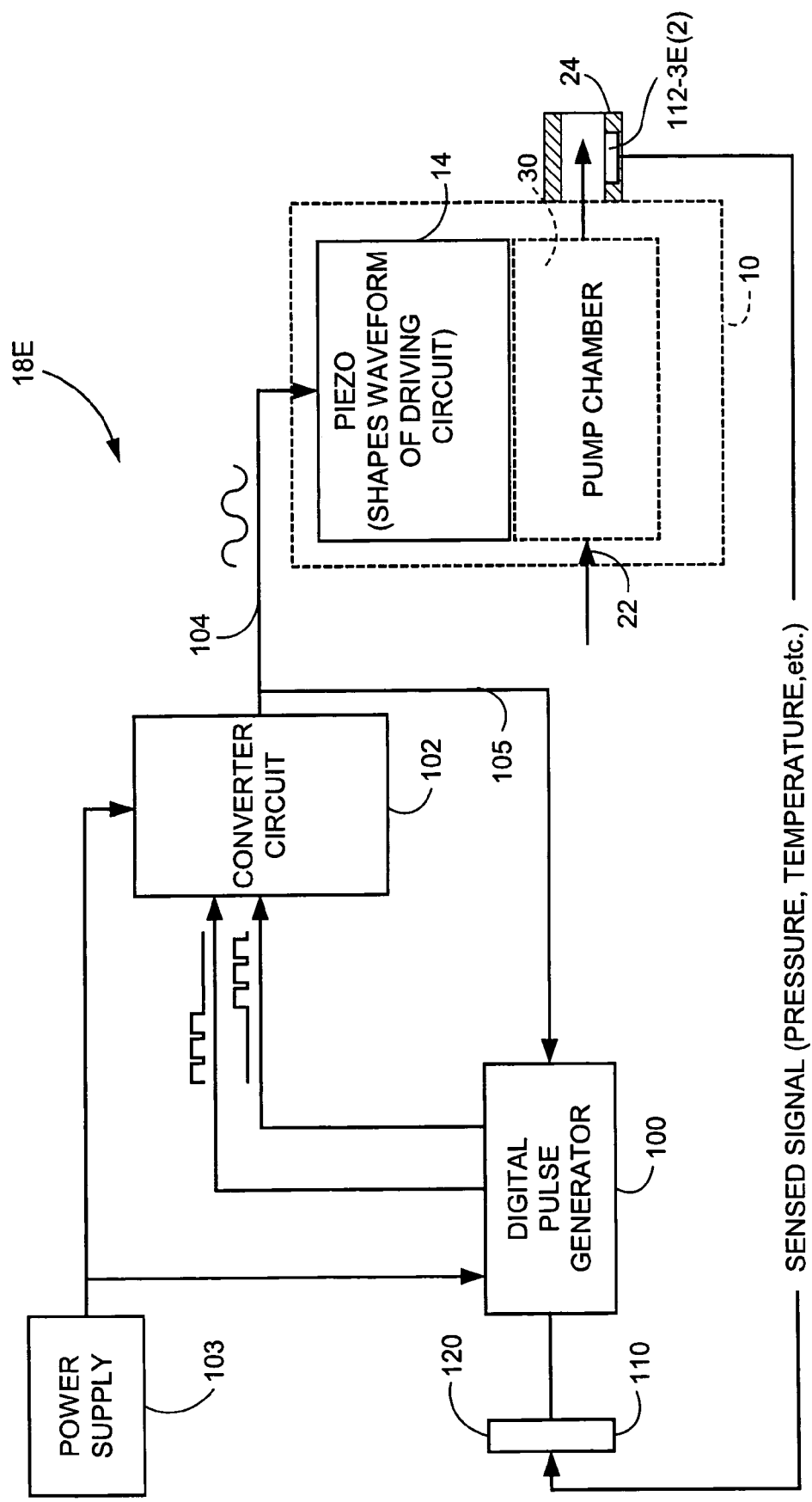
Fig. 3E(2)

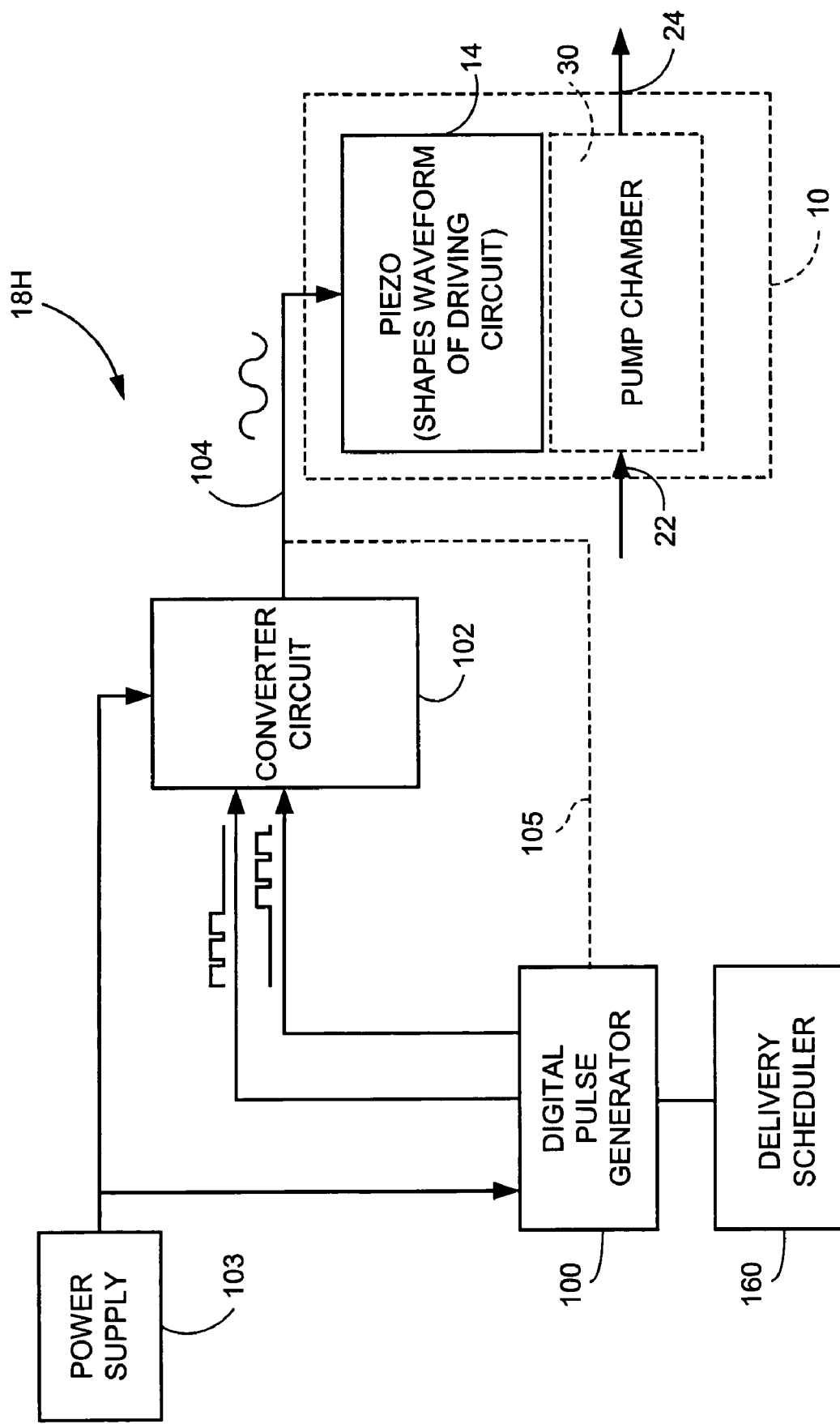
Fig. 3H(1)

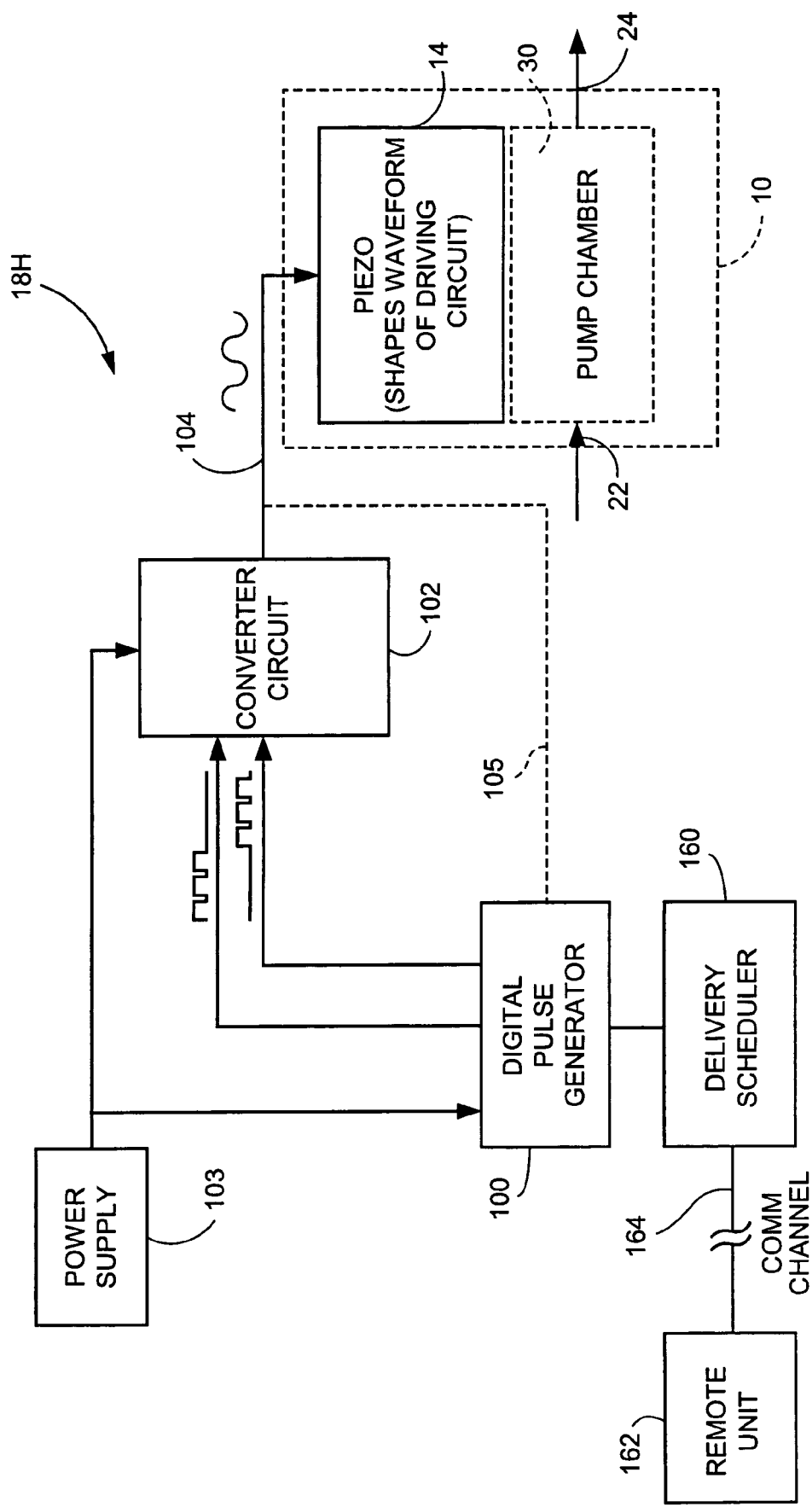
Fig. 3H(2)

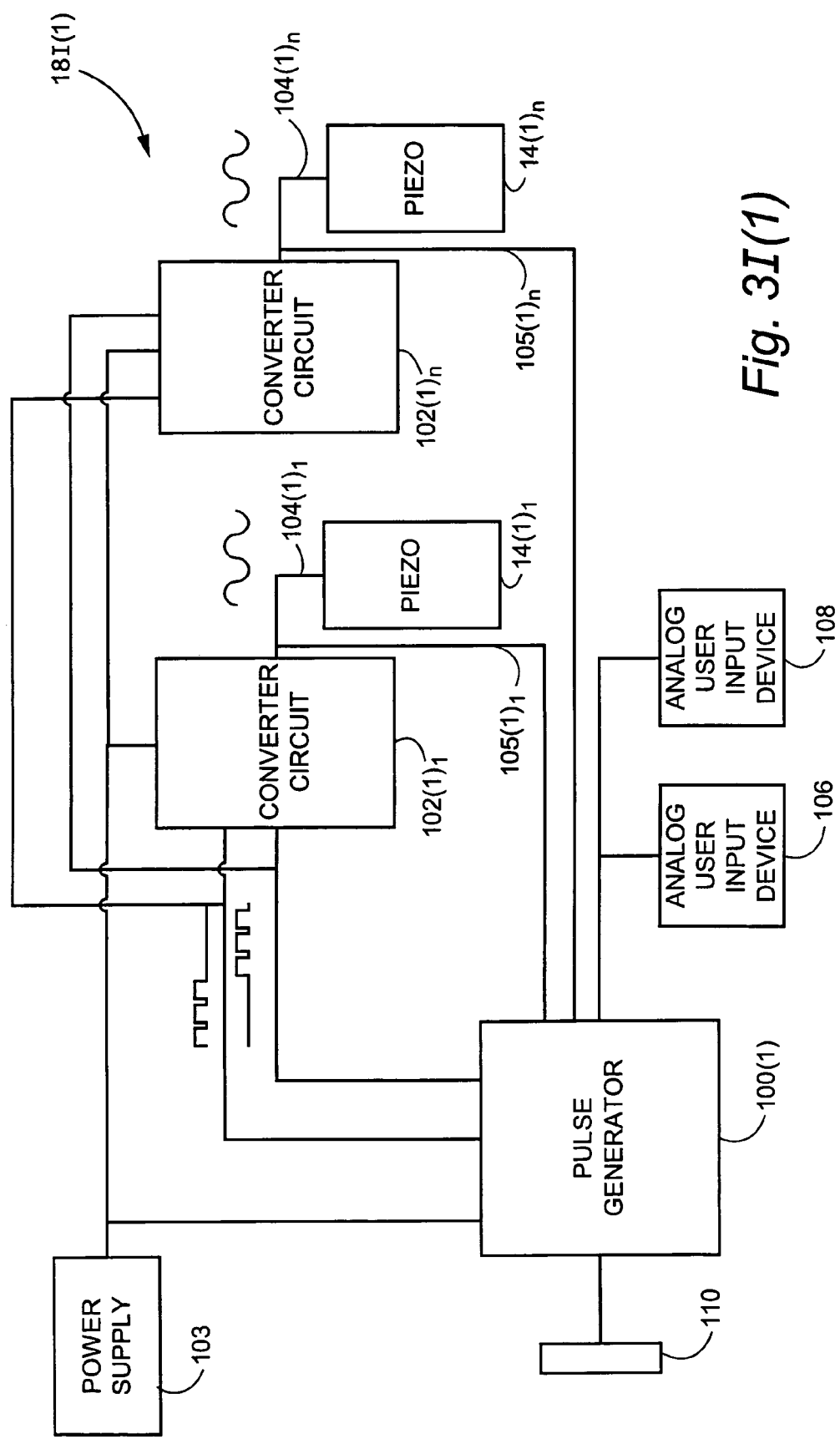
Fig. 3I(1)

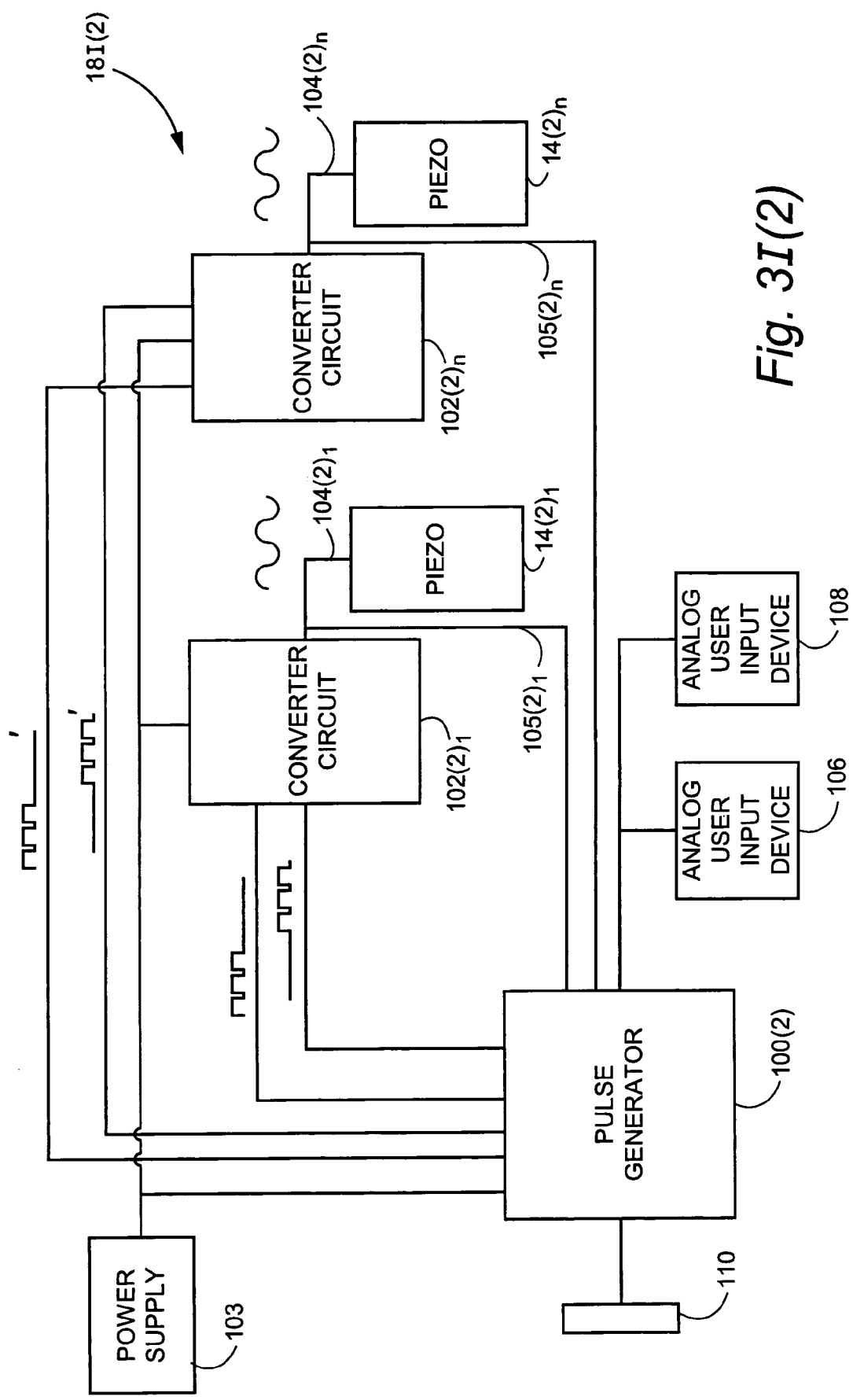
Fig. 3I(2)

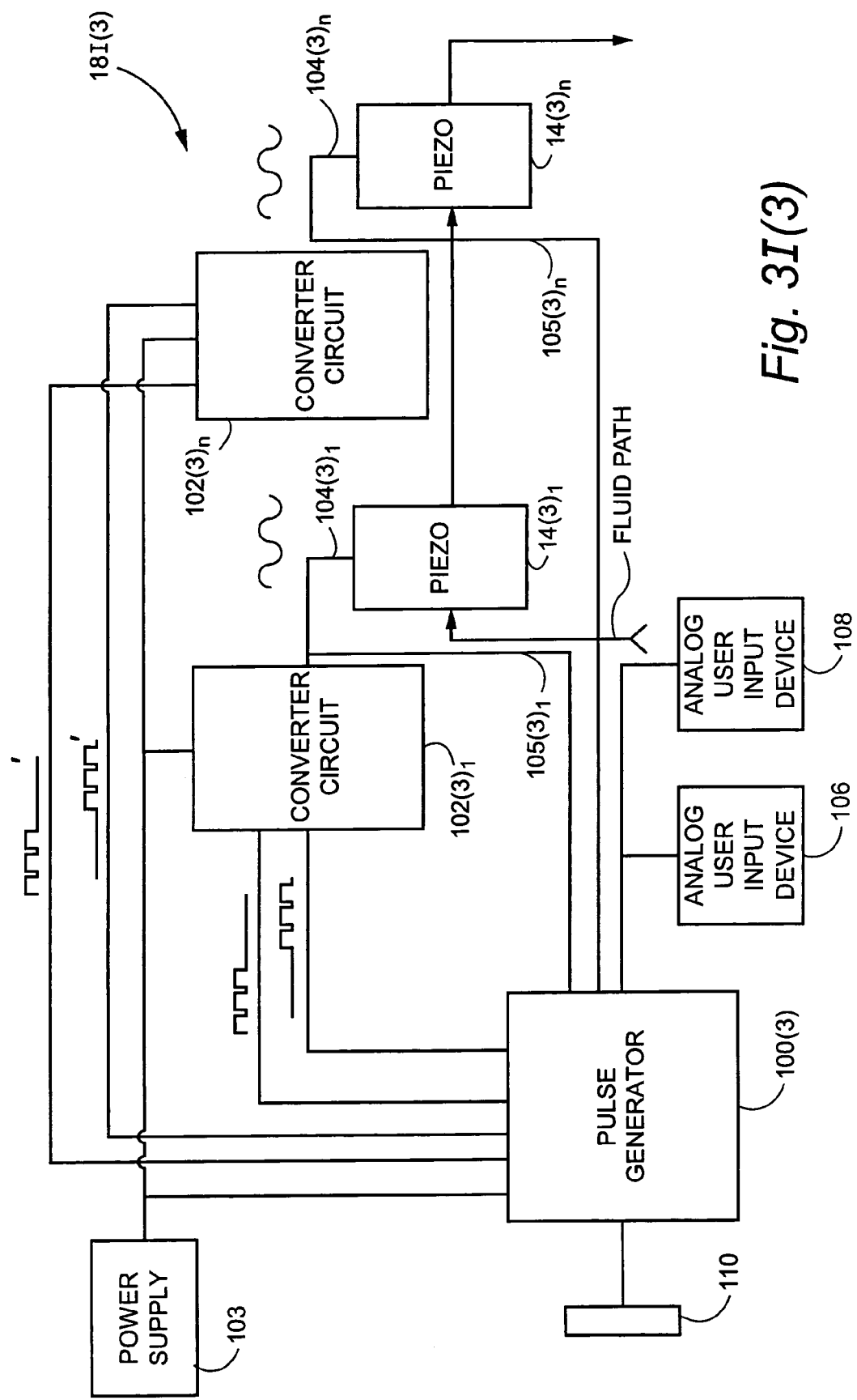
Fig. 3I(3)

Fig. 18A

OPTIMIZED WAVEFORM TABLE (140-18A)

| WAVEFORM POINTS | AMPLITUDE (SOLUTION OF WAVEFORM EQUATION AT POINT) |
|---|---|
| $X_1$ | $V_{X1}$ |
| $X_2$ | $V_{X2}$ |
| ... | ... |
| $X_J$ | $V_{XJ}$ |

Fig. 18B

OPTIMIZED WAVEFORM TABLE (140-18B)

| WAVEFORM POINTS | AMPITUDE (SOLUTION OF WAVEFORM EQUATION AT POINT) | PULSE WIDTH MODULATION VALUE FOR POINT |
|---|---|---|
| $X_1$ | $V_{X1}$ | $PWM_{X1}$ |
| $X_2$ | $V_{X2}$ | $PWM_{X2}$ |
| $X_J$ | $V_{XJ}$ | $PWM_{XJ}$ |

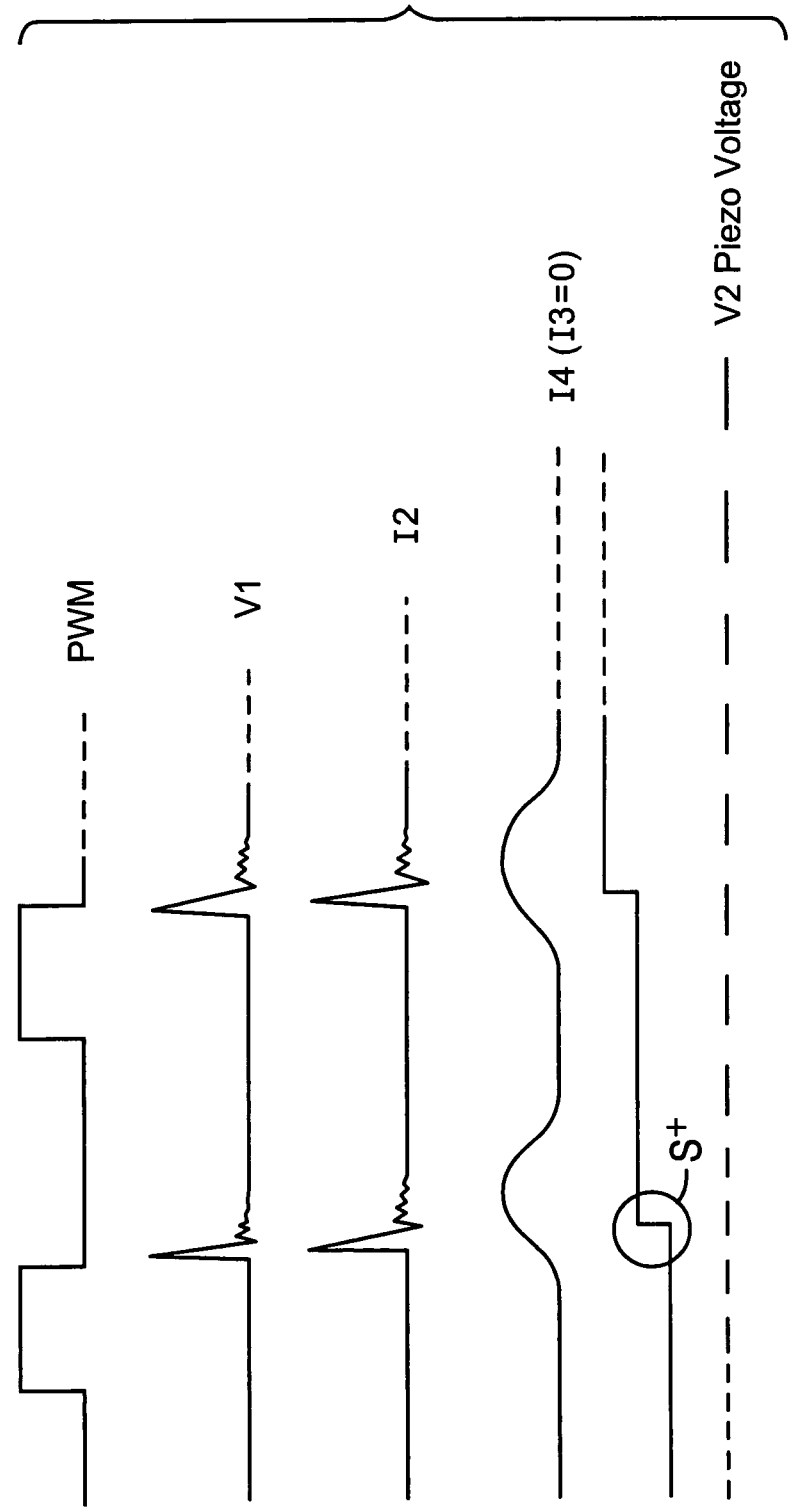

PIEZOELECTRIC DEVICES AND METHODS AND CIRCUITS FOR DRIVING SAME

This application is related to the following simultaneously-filed United States patent applications: U.S. patent application Ser. No. 10/816,000 entitled "Piezoelectric Devices And Methods And Circuits For Driving Same"; U.S. patent application Ser. No. 10/815,999 entitled "Piezoelectric Devices And Methods And Circuits For Driving Same"; and, U.S. patent application Ser. No. 10/815,978 entitled "Piezoelectric Devices And Methods And Circuits For Driving Same"; all of which are incorporated by reference herein in their entirety.

BACKGROUND

1. Field of the Invention

This invention pertains to piezoelectric elements, and particularly to circuits and methods for driving piezoelectric elements utilized in such devices such as pumps, for example.

2. Related Art and Other Considerations

A piezoelectric element is a crystalline material which produces an electric voltage when subjected to mechanical pressure. In view of their various properties, piezoelectric elements have been used as actuators in diaphragm displacement pumps. In general, piezoelectric actuators of the type used in pumps require excitation by a regularly reversing high-voltage field. Depending on the application, the excitation voltage may be anywhere from 25 to 1000 volts or more and the frequency of field reversal may be anywhere from a fraction of a cycle per second to thousands of cycles per second. Typically, this excitation signal must be derived from a relatively low-voltage source of 1.5–25 volts. It is desirable that this derivation or conversion be very energy efficient and that the associated components be inexpensive.

In addition, given that both the piezoelectric actuators and the devices that employ them often have many resonant characteristics, it is desirable for the field reversal to be monotonic—e.g., a sine wave.

An example of a reasonably effective drive circuit for driving piezoelectric elements used as pump actuators is disclosed in U.S. patent application Ser. No. 10/380,547 and U.S. patent application Ser. No. 10/380,589 (both filed Mar. 17, 2003, both entitled "Piezoelectric Actuator and Pump Using Same", and both incorporated by reference herein in their entirety). That drive circuit comprises a EL lamp driver circuit which was originally designed to drive electroluminescent (EL) lamps, but which has now ingeniously been employed in the referenced documents for driving piezoelectric pumps. The EL lamp driver circuit is a high-powered, switch-mode integrated circuit (IC) inverter intended for backlighting color LCDs and automotive applications. The specially designed EL lamp driver IC and a few components such as a discharge circuit comprise a complete EL lamp driving circuit.

Described in more detail, the EL lamp driver circuit uses a relatively high frequency oscillator or state-machine to drive a flyback circuit to produce high-voltage charges that are stored in a storage capacitor. The storage capacitor is then treated as a high-voltage source of direct current which is applied to a bridge-type switching circuit that is driven by either a second oscillator or state-machine or a signal derived from the flyback oscillator to produce a reversing field effect.

These EL lamp driver circuits have been widely employed in the electroluminescent lighting industry and consequently many of the circuit elements have been integrated into "one-chip" solutions. This EL lamp driver technology/circuitry has evolved to drive the displays of handheld electronic devices such as cell phones, Personal Digital Assistants (PDAs) and electronic games. The circuits can operate at low frequency and current draw, and at relatively high frequencies, making them very attractive for portable applications. Moreover, equipped with a discharge circuit design, the EL circuit minimizes EL lamp system noise, i.e., noise that would affect the operation of other IC's or chips.

Despite its overall ingenious and overall beneficial utilization in piezoelectric pumps, some aspects of using a EL lamp driver circuit are problematic. Several example problems are now briefly described.

As a first example problem, the EL lamp driver is limited in that it operates only at a fixed frequency once installed. The oscillators and/or state machines used in EL lamp drivers are fixed. Therefore, the EL lamp driver circuits are "Mona Lisa's"—each circuit having a fixed flyback frequency. As a result, when used in a piezoelectric pump, the EL lamp driver circuit provides a fixed piezoelectric drive frequency and a fixed output voltage to input voltage/load ratio. When used in a piezoelectric pump, the EL lamp driver circuits are "tuned" to a specific piezoelectric application by varying component values at the time of manufacture.

As a second example problem, the output wave form of the EL lamp driver circuit is a modified sawtooth which creates audible noise in the piezo even under load (due to the sharp peak on the waveform output by the EL lamp driver circuit). This is due, in part, to the architecture of the EL lamp driver circuit which employs a crude, somewhat direct current source. This current source is digitally switched by a bridge circuit to produce the reversing field, so that the resulting drive waveform is far from pure. Square waves and sawtooths are common with ragged, time-varying frequency content signals being typical. But in non-audio applications piezoelectric actuators and the devices that employ them typically need to operate at pure frequencies for maximum efficiency and to produce the least amount of audible noise. So when a drive waveform is applied that has frequency content outside of the targeted fundamental drive frequency, that extraneous frequency content adds little to the work output of the piezoelectric element but greatly increases undesirable actuator audible noise.

As a third example problem, the only variable user input to the EL lamp driver circuit is the voltage input (Vin). The EL lamp driver architecture employs a unipolar voltage source to drive the piezoelectric actuator in bipolar fashion. Given this fact, it is unavoidable that both "sides" of the piezoelectric actuator are subjected to voltage potentials other than system ground. In applications such as a pump which pumps a conductive liquid, it is highly desirable that the fluid side of the actuator always remain at system ground. This cannot be achieved using the EL lamp driver circuitry.

The current drive approach does not have a means of accepting external control inputs or monitoring local actuator related parameters. Capabilities such as resonance detection, pressure feedback, temperature feedback, external modulation, etc. are not even considered. The lack of capability to vary the frequency or voltage on the board once installed severely limits the capability of the circuit when trying to optimize the frequency or voltage to address back pressures, temperatures and other operating conditions.

BRIEF SUMMARY

A drive circuit senses a parameter of a piezoelectric actuator operating in a device and adjusts a drive signal of the piezoelectric actuator in accordance with the parameter. The drive circuit comprises a controller which controls a drive signal applied to the piezoelectric actuator; a feedback monitor which obtains a feedback signal from the piezoelectric actuator while the piezoelectric actuator works; and, a processor or other means which uses the feedback signal to determine the parameter of the piezoelectric actuator.

In one example mode, the parameter of the piezoelectric actuator which is determined by the piezoelectric actuator drive circuit is the capacitance or dielectric constant of the piezoelectric actuator. The controller controls the drive signal so that an ascertainable electrical charge is applied to the piezoelectric actuator. As the charge is applied to the piezoelectric actuator, the feedback monitor obtains a voltage value from the feedback signal. The electrical charge and the voltage value from the feedback signal is used to determine capacitance of the piezoelectric actuator.

In one example implementation of the capacitance determination mode, the drive circuit derives the drive signal from a pulse width modulated signal. The controller controls pulse widths of the pulse width modulated signal so that the ascertainable electrical charge is applied to the piezoelectric actuator. After the capacitance of the piezoelectric actuator has been determined, the controller subsequently uses the capacitance of the piezoelectric actuator as a factor in controlling the drive signal to the piezoelectric actuator. Controlling the drive signal in this way can involve controlling pulse widths of the pulse width modulated signal from which the drive signal is derived.

In other example modes, the parameter of the piezoelectric actuator which is determined by the piezoelectric actuator drive circuit is impedance or resonant frequency of the piezoelectric actuator. Using a impedance measurement technique, the drive signal is varied through a range of excitation frequencies. An voltage value is obtained from the feedback signal for each of the excitation frequencies. The resonant frequency of the piezoelectric actuator is determined as corresponding to a frequency in the range that had a minimum voltage value from the feedback signal.

Using a impulse response technique, the drive signal is varied while an "echo" is sought in the feedback signal. The resonant frequency of the piezoelectric actuator is determined as an inverse of a period of the echo.

BRIEF DESCRIPTION OF THE DRAWINGS

The foregoing and other objects, features, and advantages will be apparent from the following more particular description of preferred embodiments as illustrated in the accompanying drawings in which reference characters refer to the same parts throughout the various views. The drawings are not necessarily to scale, emphasis instead being placed upon illustrating the principles of the invention.

FIG. 6 and FIG. 6A–FIG. 6G are flowcharts showing basic steps performed upon execution of various routines by a pulse generator in accordance with an example, non-limiting embodiment.

FIG. 18A is a diagrammatic view of an optimized waveform table according to one example embodiment.

FIG. 18B is a diagrammatic view of an optimized waveform table according to another example embodiment.

FIG. 20A shows signal diagrams for a first mode of operating the piezoelectric actuator drive circuit of FIG. 5C.

DETAILED DESCRIPTION OF THE DRAWINGS

In the following description, for purposes of explanation and not limitation, specific details are set forth such as particular architectures, interfaces, techniques, etc. in order to provide a thorough understanding of the present invention. However, it will be apparent to those skilled in the art that the present invention may be practiced in other embodiments that depart from these specific details. In other instances, detailed descriptions of well-known devices, circuits, and methods are omitted so as not to obscure the description of the present invention with unnecessary detail. Moreover, individual function blocks are shown in some of the figures. Those skilled in the art will appreciate that the functions may be implemented using individual hardware circuits, using software functioning in conjunction with a suitably programmed digital microprocessor or general purpose computer, using an application specific integrated circuit (ASIC), and/or using one or more digital signal processors (DSPs). Captions or textual headings appearing in this detailed description do not define or limit the invention(s) described herein in anyway, but are merely inserted for possible convenience of the reader.

1.0 Representative Piezoelectric Pump Structure

Figure 1:
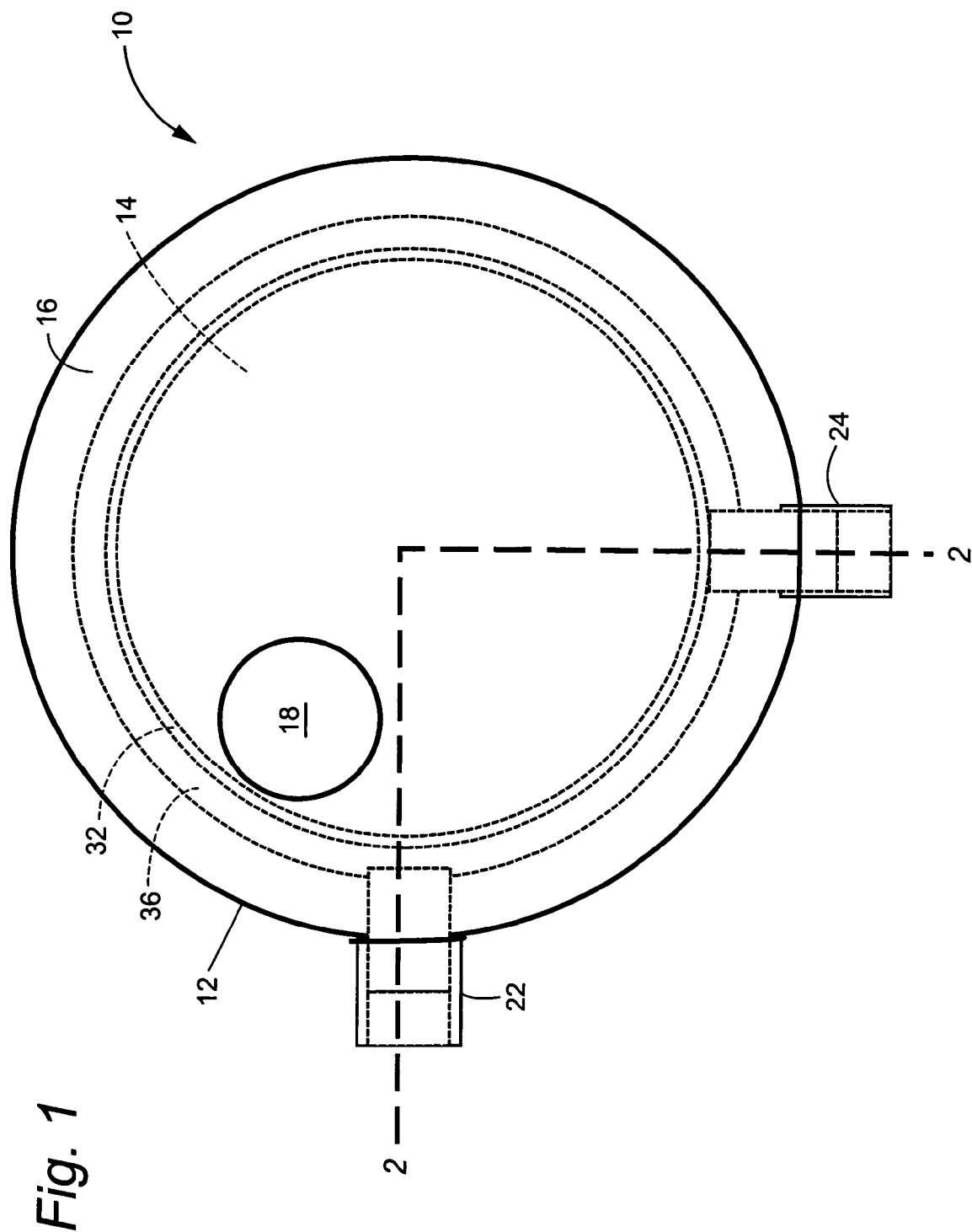
FIG. 1 is a top view of an example piezoelectric pump.
Figure 2:
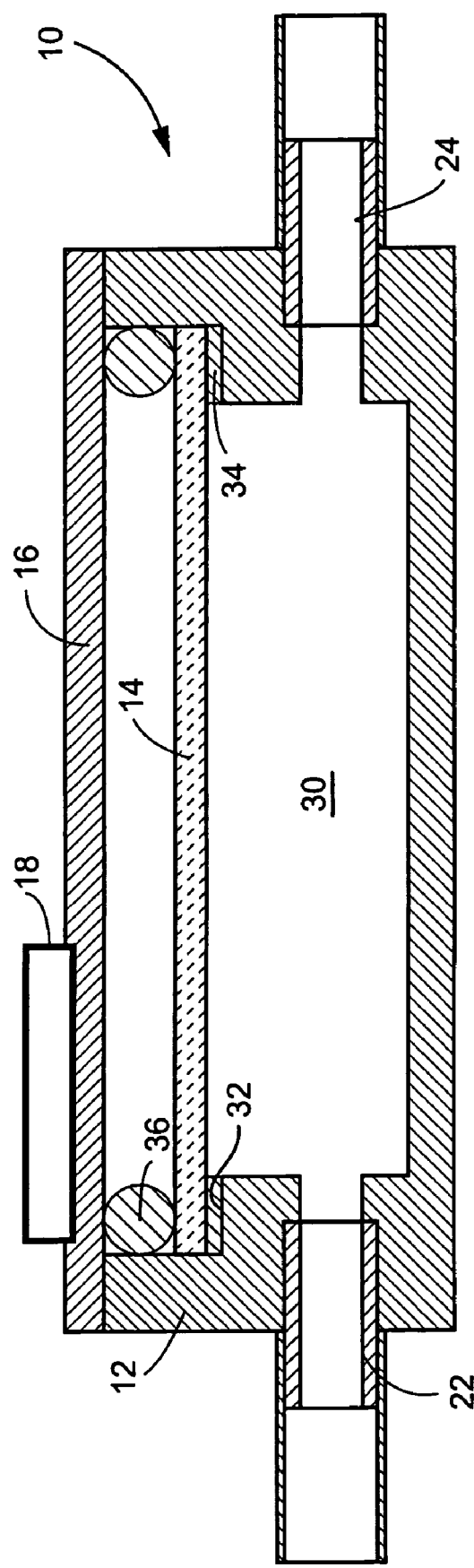
FIG. 2 is a side sectioned view of the pump of FIG. 1 taken along line 2—2.

FIG. 1 and FIG. 2 show a representative piezoelectric pump 10 which serves merely as a non-limiting example for illustrating a drive circuit and an example utilization device which hosts a piezoelectric actuator which is driven by the drive circuit. Other than having an actuator which is at least partially comprised of a piezoelectric element, the illustrated physical structure of pump 10 is not critical. Indeed, the drive method and drive circuit disclosed herein can be used with many types of utilization devices, including but not limited to different types of which have variations of some or all of the structural components of pump 10.

The example pump 10 of FIG. 1 and FIG. 2 is generally in the form of a circular thin cylinder. Pump 10 includes pump body 12; piezoelectric actuator 14; pump cover 16; and, piezoelectric actuator drive circuit 18. The pump body 12 has inlet 22 and outlet 24, either or both of which may be part of the pump body 12 or separate pieces otherwise fastened to pump body 12. Pump cover 16 may be fastened to the pump body 12 by any suitable means. The piezoelectric actuator drive circuit 18 may be externally positioned on the pump body as shown in FIG. 1. Alternatively, the pump cover may partially or entirely comprise a circuit board (e.g., printed circuit board, printed wiring board) with circuit elements which comprise the piezoelectric actuator drive circuit 18. In this alternative, the circuit board serves an additional function of a mechanical or structural part for the pump. Further locations of piezoelectric actuator drive circuit 18 are also possible, it being understood that the piezoelectric actuator drive circuit 18 has appropriate electrical leads and/or connections, including an electrical lead/connection to piezoelectric actuator 14.

A pump chamber 30 is formed in the center of the pump body 12, for example by molding or machining. The dimensions of pump 10, and hence the dimensions of pump chamber 30, depend on the particular application. A seat 32 is provided in pump body 12 at the top of the pump chamber 30. As shown in FIG. 2 the piezoelectric actuator 14 is mounted on the seat 32 to form a diaphragm in the top of the pump chamber 30. A sealing washer 34 having essentially the same outer diameter as the piezoelectric actuator 14 resides on seat 32. An O-ring seal 36 is situated on top of the piezoelectric actuator 14 to hold the piezoelectric actuator 14 in place.

In one illustrated embodiment, piezoelectric actuator 14 can take the form of a piezoelectric wafer laminated to/between one or more ruggedizing layers (e.g., metal layers). An example such piezoelectric actuator is illustrated in U.S. patent application Ser. No. 10/380,547 and U.S. patent application Ser. No. 10/380,589 (both filed Mar. 17, 2003, both entitled "Piezoelectric Actuator and Pump Using Same", and both incorporated by reference herein in their entirety). However, the drive method and drive circuit disclosed herein is not confined to any particular type of piezoelectric actuator.

As mentioned above, structural aspects of the example pump as illustrated in FIG. 1 and FIG. 2 are not constraining. For example, the geometry, size, composition, and internal configuration of the pump body can vary in other embodiments or applications. Moreover, the manner of seating or sealing or positioning of piezoelectric actuator 14 in a pump body is not critical. Further, the position, number, orientation, and structure of the inlet(s) and outlet(s) are not critical, nor is the existence or type of any particular valve which may reside in or near such one or more of such inlet(s) and/or outlet(s).

The piezoelectric actuator drive circuit 18 is preferably but not necessarily embodied in an electronic printed circuit board (PCB). The piezoelectric actuator drive circuit 18 can take many distinct forms or embodiments and have many distinct modes of operation, with some of the embodiments and modes being implemented in conjunction with other embodiments and modes (e.g., some embodiments/modes can be combined to realize yet other embodiments and modes).

2.0 Example Embodiments of Drive Circuits

Figure 3:
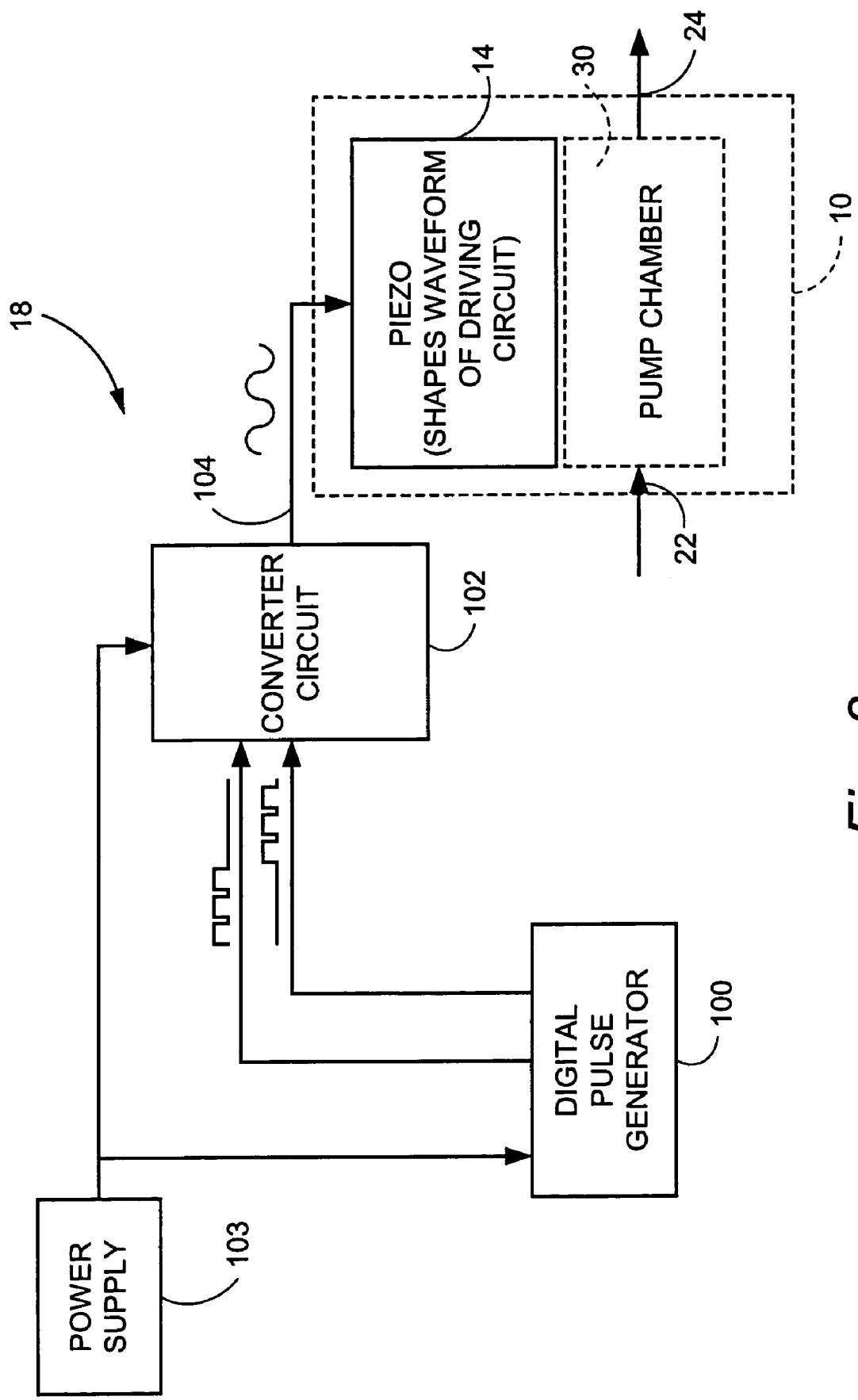
FIG. 3, FIG. 3A, FIG. 3B, FIG. 3C, FIG. 3D, FIG. 3E(1), FIG. 3E(2), FIG. 3F, FIG. 3G, FIG. 3H(1), FIG. 3H(2), FIG. 3I(1), FIG. 3I(2), FIG. 3I(3), and FIG. 3J are schematic views of differing embodiments of example piezoelectric actuator drive circuits.
Figure 3A:
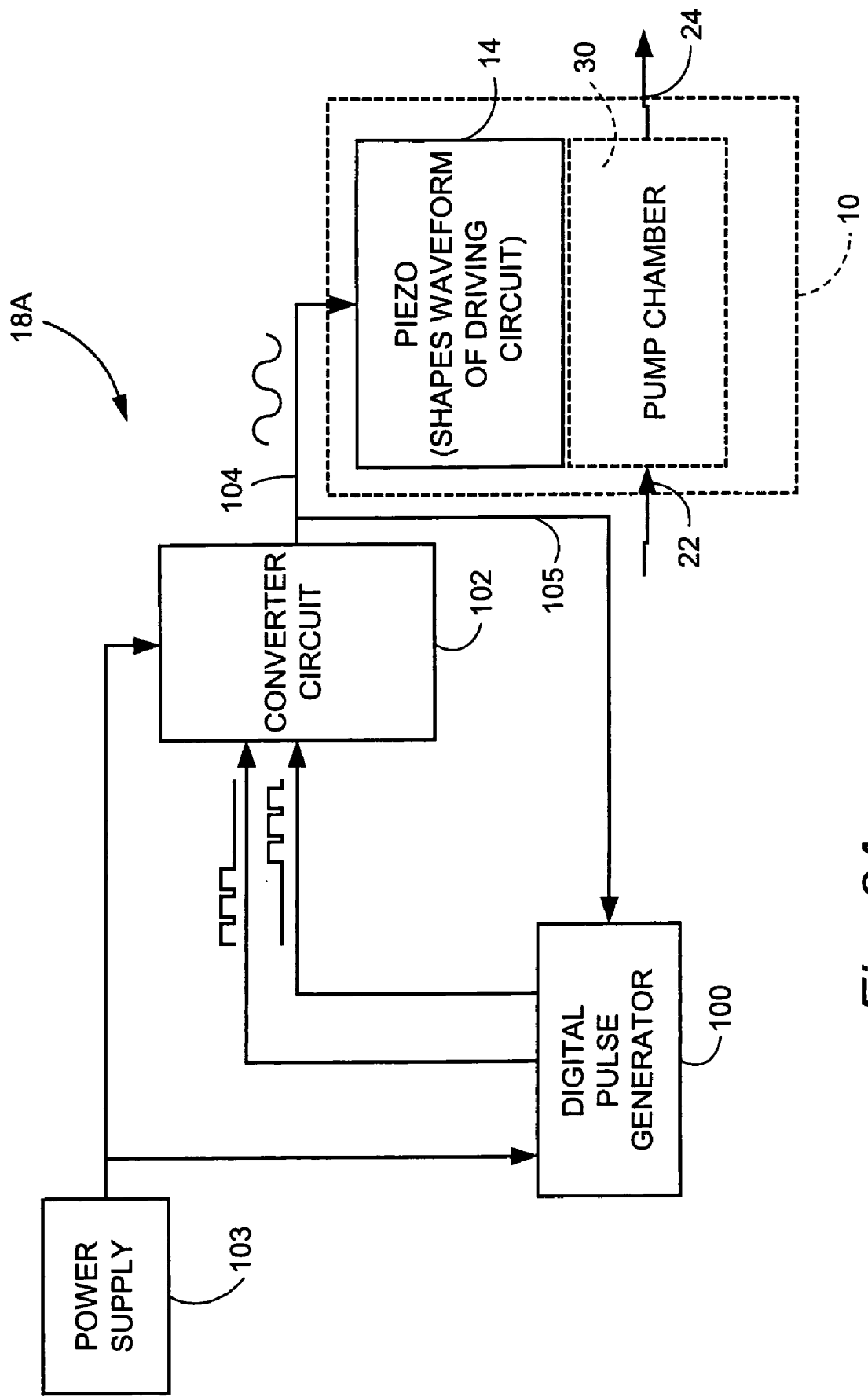
Figure 3B:
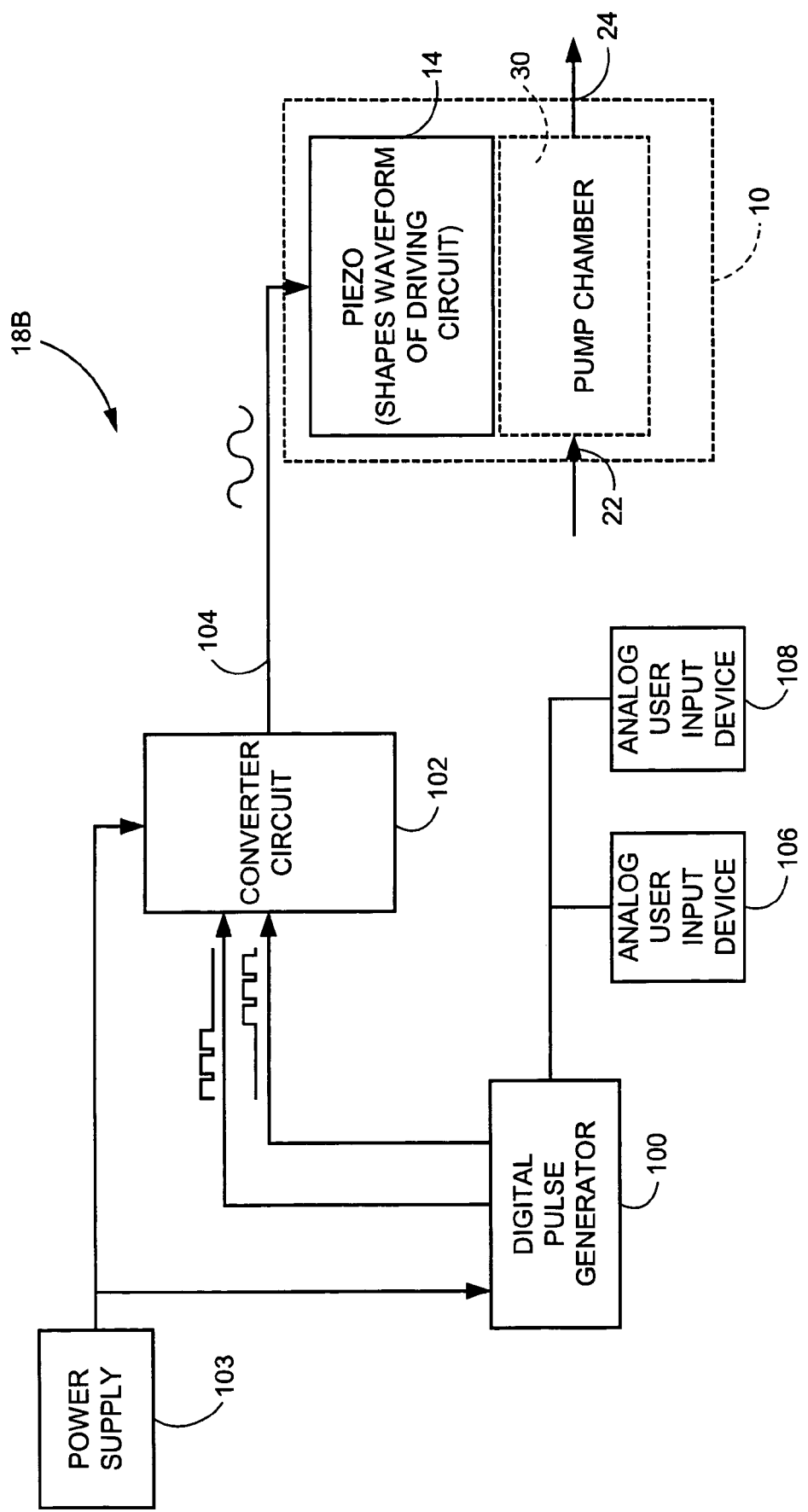
Figure 3D:
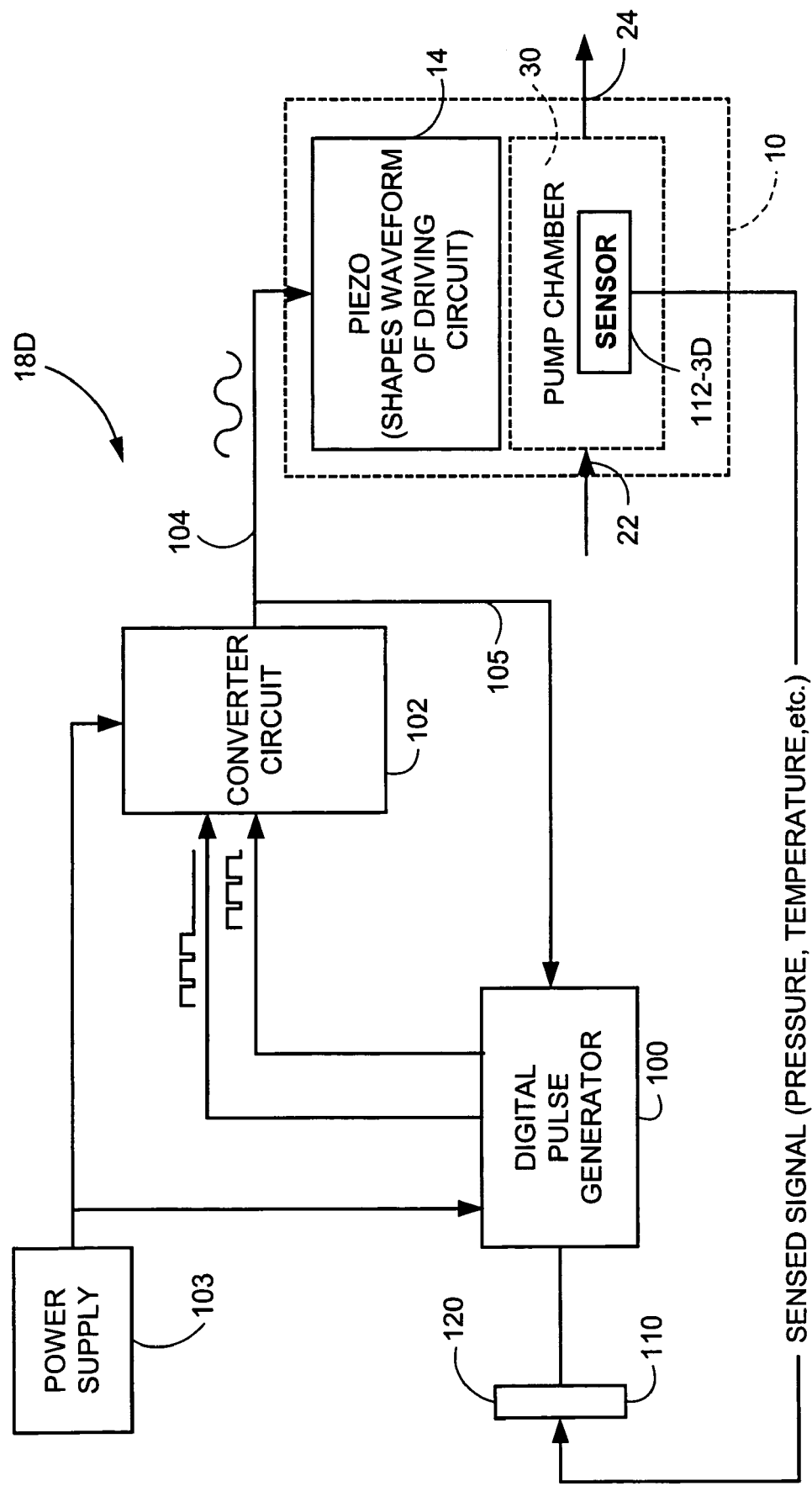
Figure 3F:
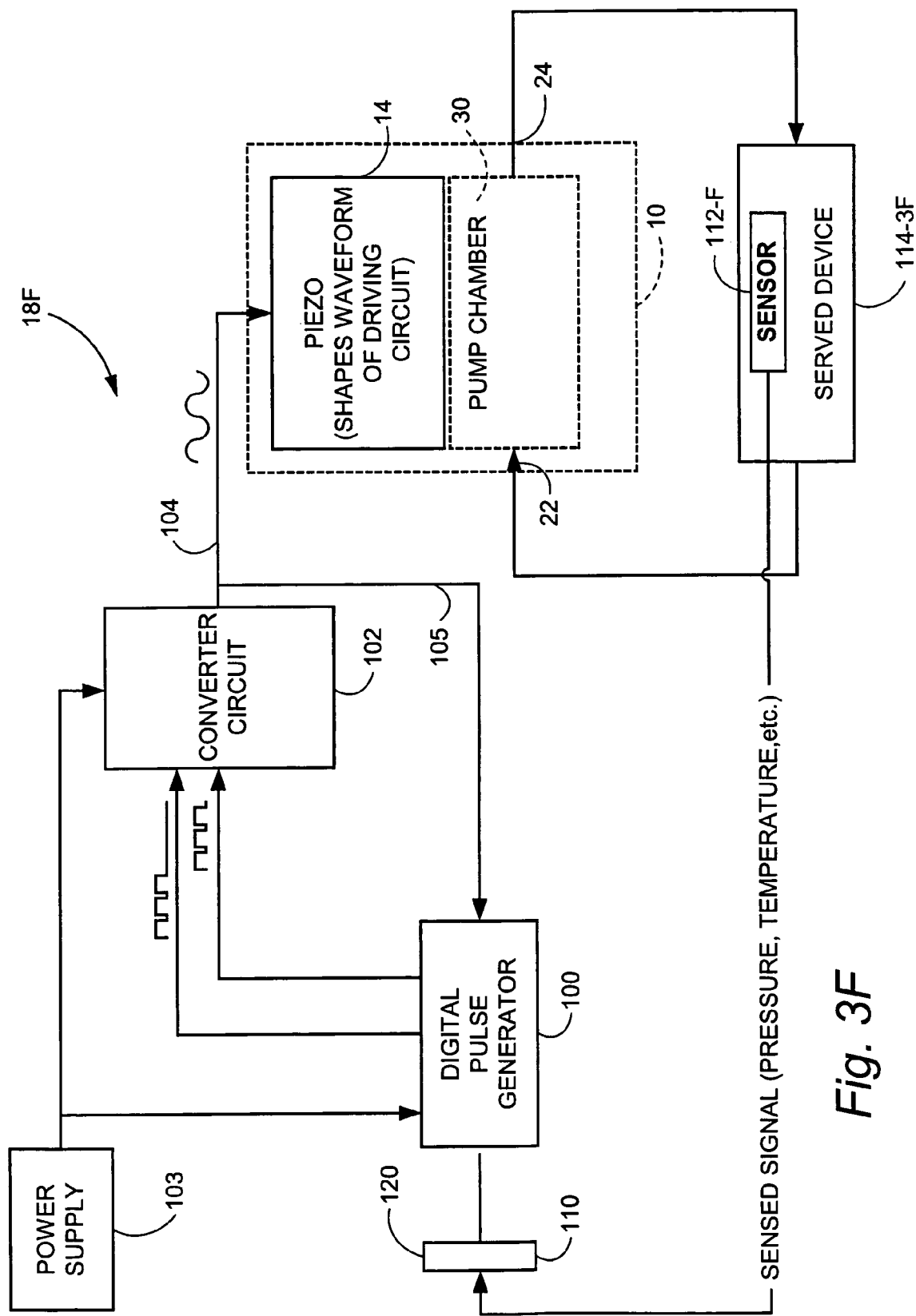
Figure 3G:
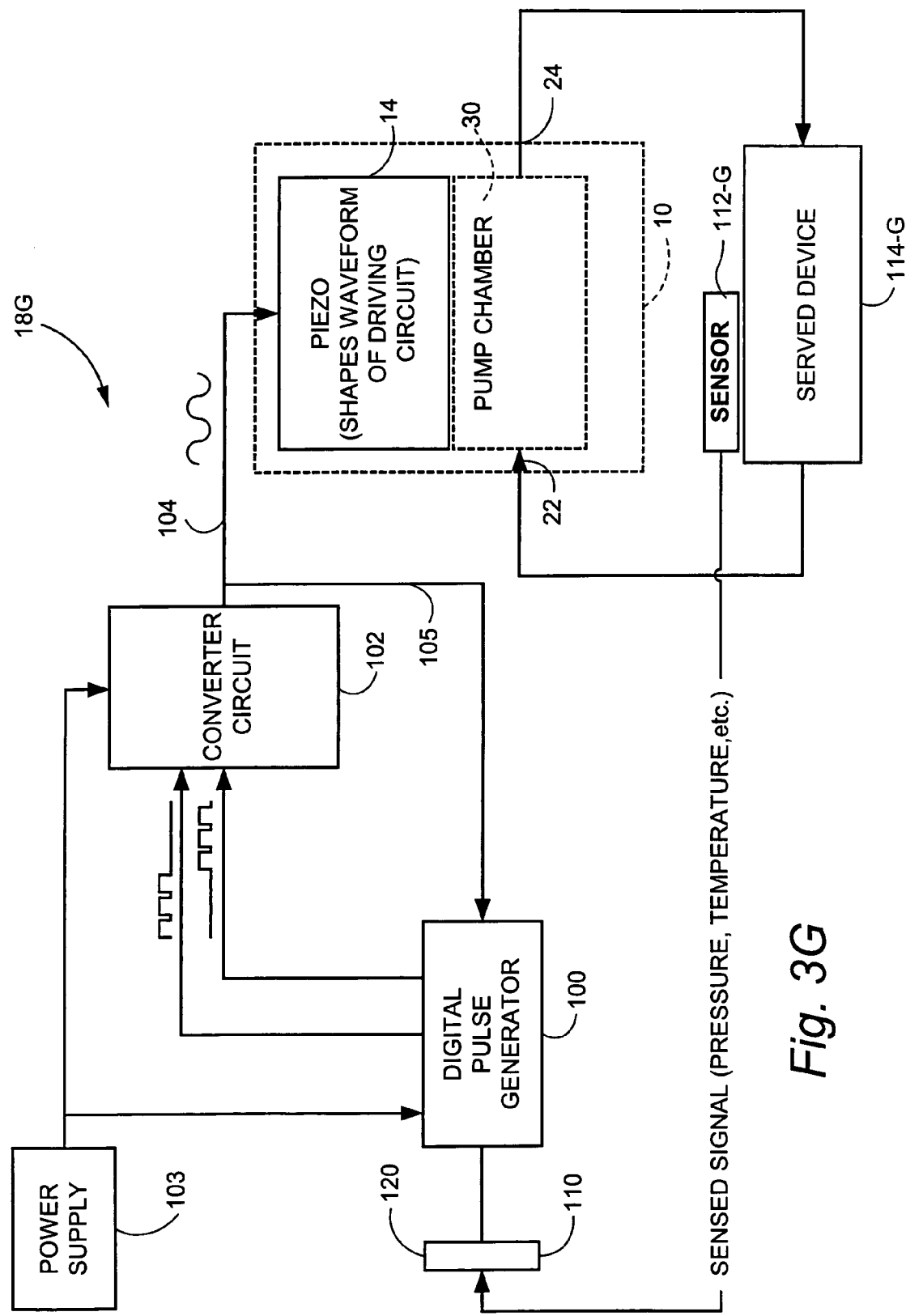
Figure 3J:
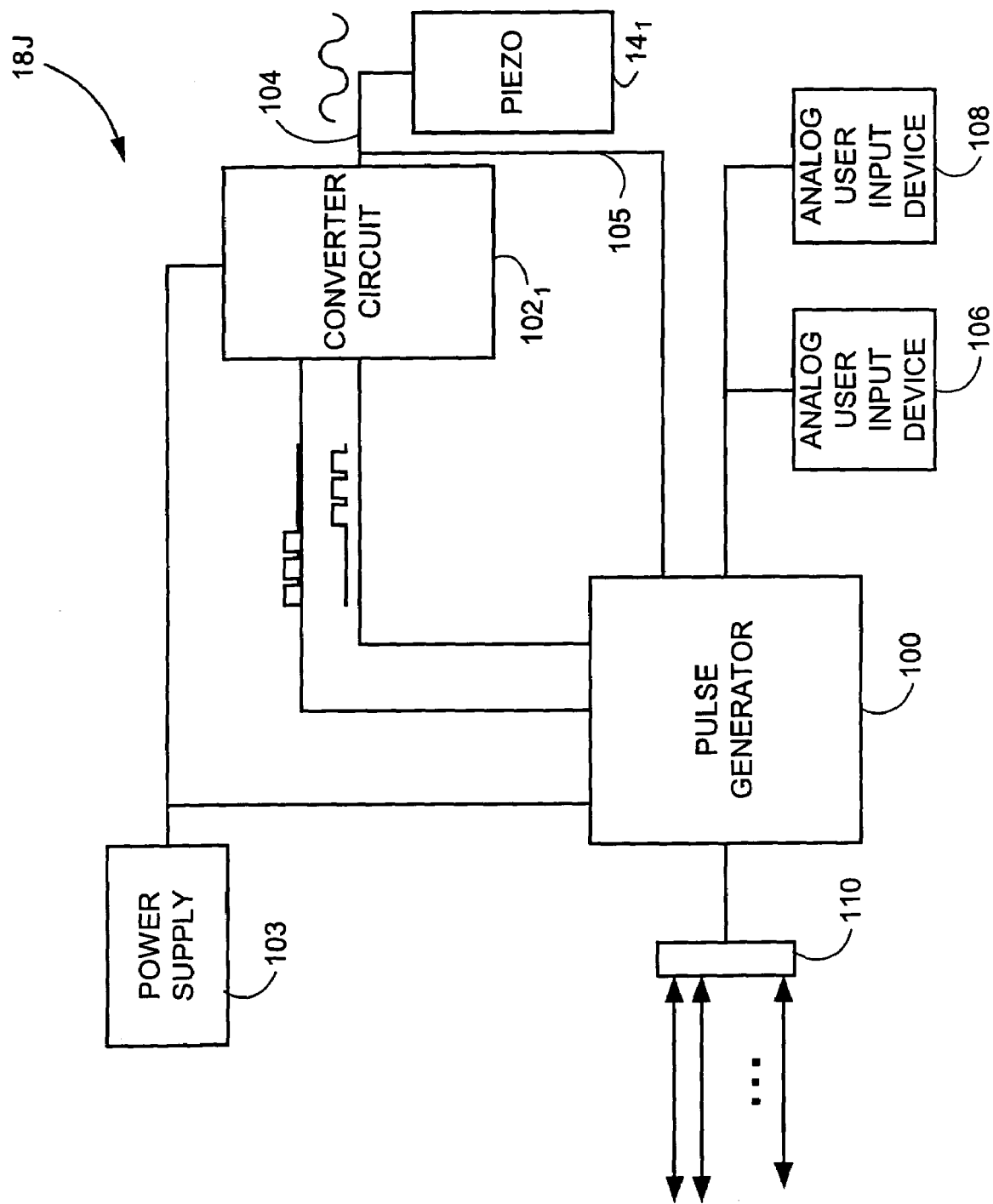

General non-limiting examples of the piezoelectric actuator drive circuit 18 are illustrated in FIG. 3 and FIG. 3A, FIG. 3B, FIG. 3C, FIG. 3D, FIG. 3E(1), FIG. 3E(2), FIG. 3F, FIG. 3G, FIG. 3H(1), FIG. 3H(2), FIG. 3I(1), FIG. 3I(2), FIG. 3I(3), and FIG. 3J. In each of the example embodiments and modes the piezoelectric actuator drive circuit 18 applies a series of low power, long period digital pulses to the converter circuit 102, so that converter circuit 102 can apply packet charges which are integrated by the piezoelectric actuator 14. In each of these embodiment, the piezoelectric actuator drive circuit 18 applies a drive signal to the piezoelectric actuator 14, with the piezoelectric actuator 14 comprising or being adjacent or proximate to a utilization device. The particular utilization device which uses or incorporates the piezoelectric actuator 14 depends upon the application and/or environment. One example, non-limiting utilization device discussed herein is a piezoelectric pump.

2.1 Drive Circuit Providing Digital Pulses

As shown in simplified form in FIG. 3, piezoelectric actuator drive circuit 18 comprises digital pulse generator 100 and converter circuit 102. A power supply 103 provides power both to pulse generator 100 and converter circuit 102. The pulse generator 100 provides low voltage, long period digital pulses to converter circuit 102. The converter circuit 102 outputs a stream of high voltage, short period pulses (charge packets) on line 104 to piezoelectric actuator 14. Thus, as one of its aspects, the piezoelectric actuator drive circuit 18 of FIG. 3 (and of all other embodiments of drive circuits described herein) outputs a digital pulse stream (e.g., series of charge packets) which are integrated by the piezoelectric actuator 14.

2.2 Drive Circuit Receiving Feedback Signal

As an aspect of its operation, the piezoelectric actuator 14 actually serves as part of piezoelectric actuator drive circuit 18. By virtue e.g., of its capacitance, piezoelectric actuator 14 integrates the short period pulses (charge packets) which are output by converter circuit 102 as the drive signal on line 104. In view of the integration of drive signal on line 104, the drive signal on line 104 actually acquires the general shape of a sine wave. Thus, piezoelectric actuator 14 contributes to shaping the waveform (e.g., drive signal applied on line 104) of the piezoelectric actuator drive circuit 18.

Figure 4A:
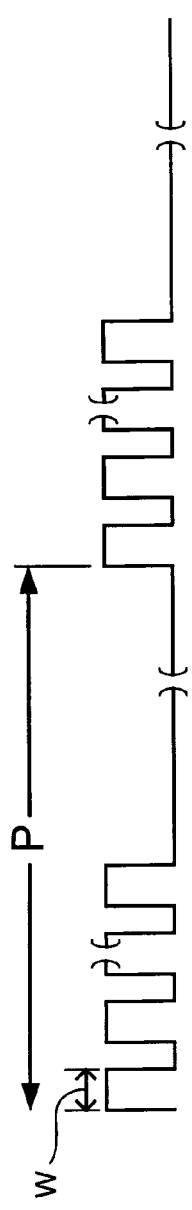
FIG. 4A–FIG. 4D are diagrammatic views of signals occurring in an example piezoelectric actuator drive circuit.

The converter circuit 102 receives digital pulses from the pulse generator 100 and generates a stream of high voltage, short period pulses (charge packets) on line 104. In an illustrated example embodiment, the digital pulses applied to converter circuit 102 from pulse generator 100 have a pulse width modulation and a period or cycle which affects the amplitude and the period of the sine wave waveform which results as the drive signal on line 104. For sake of basic illustration, FIG. 4A shows a series of the digital pulses which are pulse width modulated. The signal of FIG. 4A has a period P, with the digital pulses having a pulse width W. As explained subsequently, the positive pulse having the width W corresponds to a portion of the period P in which inductance(s) in converter circuit 102 are charged for subsequent delivery of charge as the drive signal on line 104.

FIG. 3A shows an embodiment/mode of piezoelectric actuator drive circuit 18A in which the pulse generator 100 receives a feedback signal on line 105. The feedback signal on line 105 is preferably a voltage feedback signal which can be utilized for various purposes, and in such case is an analog signal. For example, the voltage feedback signal on line 105 can be utilized to determine the resonance or capacitance of piezoelectric actuator 14. Using the voltage feedback signal on line 105, the piezoelectric actuator drive circuit 18 can build any desired waveform for application to piezoelectric actuator 14. Thus, as another of its aspects, the piezoelectric actuator drive circuit can utilize a feedback signal to shape the waveform of the drive signal for piezoelectric actuator 14.

2.3 Drive Circuit Receiving Analog Input Signal

FIG. 3B shows an embodiment/mode of piezoelectric actuator drive circuit 18B in which the drive signal on line 104 is generated in accordance with or influenced by an analog input signal to the drive circuit. The analog input signal is obtained from a user input device, two of which happen to be shown in FIG. 3B as user input device 106 and user input device 108 shown in FIG. 3B. It should be understood that a fewer or greater number of user input devices can be utilized. The user input devices 106 and 108 can be, for example, variable potentiometers or trimpots or any other device which generates or applies an analog signal in accordance with a user-selected number. In an example embodiment, user input device 106 can be used to set the period of the drive signal on line 104 by setting the period P of the pulse width modulated digital pulses applied by pulse generator 100 to converter circuit 102 (see FIG. 4). User input device 108 can be used to set a voltage/amplitude of the drive signal on line 104 by setting the pulse width W of the pulse width modulated digital pulses applied by pulse generator 100 to converter circuit 102 (see FIG. 4). The user input device 106 and user input device 108 are adjusted by the user to generate voltages that are somewhere between ground and an A/D reference level (e.g., of a microcontroller which can comprise pulse generator 100). As one aspect of operation, these signals can be converted in software to control signals for frequency and pump peak-to-peak drive voltage. Typically, a user might set the pots to (for example) a 60 Hz frequency and 350 volts peak-to-peak drive. Thus, as another of its aspects, the piezoelectric actuator drive circuit can utilize an analog input signal to influence a drive signal that is applied as digital pulses to a piezoelectric actuator.

2.4 Drive Circuit Receiving Digital Input Signal

FIG. 3C shows an embodiment/mode of piezoelectric actuator drive circuit 18C in which the drive signal on line 104 is generated in accordance with or influenced by a digital signal which is inputted through a graphical user interface (GUI) or the like. In the particular illustration of FIG. 3C, the graphical user interface (GUI) resides at a computer 109 (which can be a desktop as pictured, or laptop, or other computer-like terminal) and can take the form of keyboard, pointer (e.g. mouse), touch screen, or other suitable input device. The digital signal from computer 109 can be applied via connector 110 to pulse generator 100. Thus, as another of its aspects, the piezoelectric actuator drive circuit can utilize a digital input signal(s) to influence a drive signal that is applied to a piezoelectric actuator.

2.5 Drive Circuit Receiving Input Signal from Sensor in Utilization Device

FIG. 3D shows an embodiment/mode of piezoelectric actuator drive circuit 18D in which the drive signal on line 104 is generated in accordance with or influenced by a digital signal which is generated by a sensor 112-3D which is located in an interior of the utilization device, e.g., in pump chamber 30 of pump 10. In the illustrated embodiment, sensor 112-3D is immersed in or at least partially in contact with fluid in pump chamber 30. The sensor 112-3D can be mounted flush on a internal wall of the pump chamber 30 or otherwise situated within pump chamber 30. The sensor 112-3D can sense any appropriate parameter of fluid in pump chamber 30 which is germane to operation of piezoelectric actuator 14 and pump 10, such as temperature, viscosity, pressure, or deflection of piezoelectric actuator 14, for example. Use of the sensor 112-3D is an example of a mode in which the drive circuit facilitates changing (e.g., dynamically) the drive signal in dependence upon a sensed operational parameter of the pump.

2.6 Drive Circuit Receiving Input Signal from Sensor Elsewhere in/on Utilization Device Whereas FIG. 3D a sensor which is located inside a utilization device, FIG. 3E(1) and FIG. 3E(2) show embodiments/modes of piezoelectric actuator drive circuit 18E(1) and 18E(2) in which the drive signal on line 104 is generated in accordance with or influenced by a digital signal which is generated by respective sensors 112-3E(1) and 112-3E(2) which are located elsewhere about the utilization device, e.g., about pump 10. In FIG. 3-E(1), sensor 112-3E(1) is situated in a back portion of the pump and is shown as abutting piezoelectric actuator 14. The sensor 112-3E(1) can be used, e.g., to sense displacement of piezoelectric actuator 14 and is not exposed to fluid in pump chamber 30. The sensor 112-3E(2) of FIG. 3E(2) is positioned in an outlet 24, and can also sense any appropriate parameter germane to operation of pump 10, such as temperature, viscosity, flowrate, or pressure, for example.

2.7 Drive Circuit Receiving Input Signal from Sensor Internal to Served Device

FIG. 3F shows an embodiment/mode of piezoelectric actuator drive circuit 18F in which the drive signal on line 104 is generated in accordance with or influenced by a digital signal which is generated by a sensor 112-3F which is located within a served device 114-3F. The device 114-3F is referenced as a served device in the sense that fluid pumped by pump 10 is directed or circulated around, through, or near the served device. The served device 114-3F can be, for example, electronics (e.g., a processor or other heat dissipating electrical device that invites cooling), a heat exchanger (which is cooled by pumped fluid), or medical apparatus. As such, a path of fluid flow is illustrated from outlet 24 of pump 10 to served device 114-3F and back from served device 114-3F to inlet 22 of pump 10.

2.8 Drive Circuit Receiving Input Signal from Sensor Proximate Served Device

FIG. 3G shows an embodiment/mode of piezoelectric actuator drive circuit 18G in which the drive signal on line 104 is generated in accordance with or influenced by a digital signal which is generated by a sensor 112-3G which is located on or near a served device 114-3G. The identity and nature of the served device 114-3G depends on the application and use of pump 10, and includes but is not limited to applications in the electronics and medical fields such as those described above.

2.10 Drive Circuit Operating in Conjunction with Delivery Scheduler

FIG. 3H(1) shows an embodiment/mode of piezoelectric actuator drive circuit 18G which works in conjunction with a delivery scheduler 160. By receiving input from the delivery scheduler 160, the piezoelectric actuator drive circuit 18G controls non-continuous operation of the piezoelectric actuator 14. For example, the delivery scheduler 160 may either control or supply piezoelectric actuator drive circuit 18G with information for the timing of application of a drive signal on line 104 to piezoelectric actuator 14. The delivery scheduler 160 can but does not have to be utilized in embodiments which receive feedback on line 105, for which reason line 105 is shown as a broken line in FIG. 3H(1).

The logic and operation of delivery scheduler 160 can be varied from application to application. For example, delivery scheduler 160 may direct piezoelectric actuator drive circuit 18G to supply a drive signal for one or more finite time periods (e.g., in response to external stimuli or signal to delivery scheduler 160 or to piezoelectric actuator drive circuit 18G). One example scenario for such finite delivery involves driving piezoelectric actuator 14 in a pump for delivering or dosing fluid (e.g., medication) in accordance with a prescribed flow and/or volume amount.

Alternatively, delivery scheduler 160 may apprise piezoelectric actuator drive circuit 18H of certain sensed conditions which are to be monitored either to initiate or to terminate the drive signal on line 104 to piezoelectric actuator 14. For example, through delivery scheduler 160 the piezoelectric actuator drive circuit 18H may be instructed to apply the drive signal to piezoelectric actuator 14 and thus turn on the utilization device incorporating the same when a temperature (e.g., of a fluid) is detected to be outside a predefined temperature range.

The delivery scheduler 160 can be implemented in various ways. For example, logic for the delivery scheduler 160 can be included in a microprocessor of the digital pulse generator and accessed through a graphical user interface or other input device. Alternatively, the delivery scheduler 160 may be a separate processor or computer as understood with reference to FIG. 3C.

In yet further embodiments/modes, generically illustrated by FIG. 3H(2), the delivery scheduler 160 may include a remote unit 162 which is connected to digital pulse generator 100 through an appropriate communication channel 164. For example, the communication channel 164 may be a wireless network, in which case both the delivery scheduler 160 and the remote unit 162 include a wireless station (e.g., laptop with mobile termination, cell phone, Bluetooth unit, etc.) so that a user may send programming information (e.g., drive signal start and/or stop times) to delivery scheduler 160 over an air interface (e.g., radio frequency or other electromagnetic spectra).

As another example, the remote unit may be a browser and the communication channel 164 can comprise a packet network such as the Internet, for example. In such example, either the piezoelectric actuator drive circuit 18H or the utilization device itself may have its own internet or network address.

Using either of these or other implementations, through the remote unit a user can input data to delivery scheduler 160 so that the delivery scheduler 160 can control the timing of application and cessation of the drive signal to the piezoelectric actuator 14.

2.11 Drive Circuit Driving Plural Actuators

FIG. 3I(1)–FIG. 3I(3) show embodiments/modes of piezoelectric actuator drive circuits 18I(1)–18I(3) which serve plural piezoelectric actuators. Distinctive elements of FIG. 3I(x) bear a corresponding "x" parenthetical suffix, and for each FIG. 3I(x) the piezoelectric actuator drive circuit 18I(x) serves plural piezoelectric actuators $14(x)_y$, where y ranges from 1 to n. For each embodiment, the plural piezoelectric actuators $14(x)_y$ may be incorporated in respective plural utilization devices (e.g., plural pumps 10), or even plural types of utilization devices. For example, piezoelectric actuator $14(x)_1$ may be included in a pump; piezoelectric actuator $14(x)_2$ may be included in a fan or other type (non-pump) of utilization device. Alternatively, in other embodiments the plural piezoelectric actuators may be may be utilized in a single device or system. Preferably but not necessarily the piezoelectric actuator drive circuits 18I(x) comprise a separate converter circuit $102(x)_y$ for each of the plural piezoelectric actuators $14(x)_y$.

In the embodiment/mode of FIG. 3I(1) the same PWM-A and PWM-B digital pulses generated by pulse generator 100 are applied to the converter circuits $102(1)_1$ and $102(1)_n$ associated with the separate piezoelectric actuators $14(1)_1$ and $14(1)_n$, respectively. The embodiment/mode of FIG. 3I(1) is particularly suitable when the plural piezoelectric actuators $14(x)_y$ function in parallel and/or in time synchronization.

In the embodiment/mode of FIG. 3I(2), the pulse generator 100(2) produces different PWM-A and PWM-B digital pulses for at least two of the converter circuits $102(2)_y$, so that the plural piezoelectric actuators $14(2)_y$ are driven differently. The embodiment/mode of FIG. 3I(2) is particularly beneficial when the feedback signals on line $105(2)_y$ or other input signals (e.g., sensor input signals as described, e.g., with reference to FIG. 3D, FIG. 3E(1), and FIG. 3E(2)) require or invite different PWM-A and PWM-B digital pulses. The different PWM-A and PWM-B digital pulses may be needed either to synchronize or time the plural and uniquely functioning/sensed piezoelectric actuators $14(2)_y$, or otherwise to uniquely drive each piezoelectric actuator $14(2)_y$. For example, two piezoelectric actuators $14(2)_y$ which are driven in parallel may nevertheless require different PWM-A and PWM-B digital pulses in view of such differing factors as fluid properties, length of tube, tube composition, etc. FIG. 3I(3) shows a variation of the embodiment of FIG. 3I(2) in which one or more of the piezoelectric actuators $14(3)_y$ are situated in series with respect to fluid handling.

If desired, input signals for the piezoelectric actuator drive circuits 18I(x) can be obtained from one or more analog input devices or one or more digital input devices (e.g., sensors) as understood from the preceding discussion, so that (in addition to serving plural piezoelectric actuators $14(x)_y$) the piezoelectric actuator drive circuits $18I(x)$ can take on attributes of any of the previously described embodiments.

2.12 Drive Circuit Receiving Analog and Digital Input Signals

FIG. 3J shows an embodiment/mode of piezoelectric actuator drive circuit 18J in which the drive signal on line 104 is generated in accordance with or influenced by a both one or more analog input signals and one or more digital signals. In the non-limiting example shown, two analog signals are received from user input device 106 and user input device 108. The one or more digital signals are received by pulse generator 100 through connector 110, and can be originated by user input devices or sensors such as those illustrated by way of example in the preceding embodiments.

3.0 Example Drive Circuit Implementation

Subsequent generic reference herein to a drive circuit, or to a piezoelectric actuator drive circuit (such as piezoelectric actuator drive circuit 18), can refer to one or more types of piezoelectric actuator drive circuits, such as those types of drive circuits which have been generally described above. Reference to a drive circuit, or to a piezoelectric actuator drive circuit (such as piezoelectric actuator drive circuit 18), is not constrained or limited by the examples herein provided.

FIG. 5A, FIG. 5B, FIG. 5C, and FIG. 5D show, in more detail, illustrative example (non-limiting) implementations piezoelectric actuator drive circuits 18 (which could be utilized, e.g., for one or more of the piezoelectric actuator drive circuits 18 described above). As in the foregoing, the piezoelectric actuator drive circuits 18 herein described produce a drive signal for a pump having a piezoelectric actuator, with the piezoelectric actuator forming a part of the drive circuit and serving to shape a waveform of the drive signal for the piezoelectric actuator.

3.1 First Example Drive Circuit: Structure

Figure 5A:
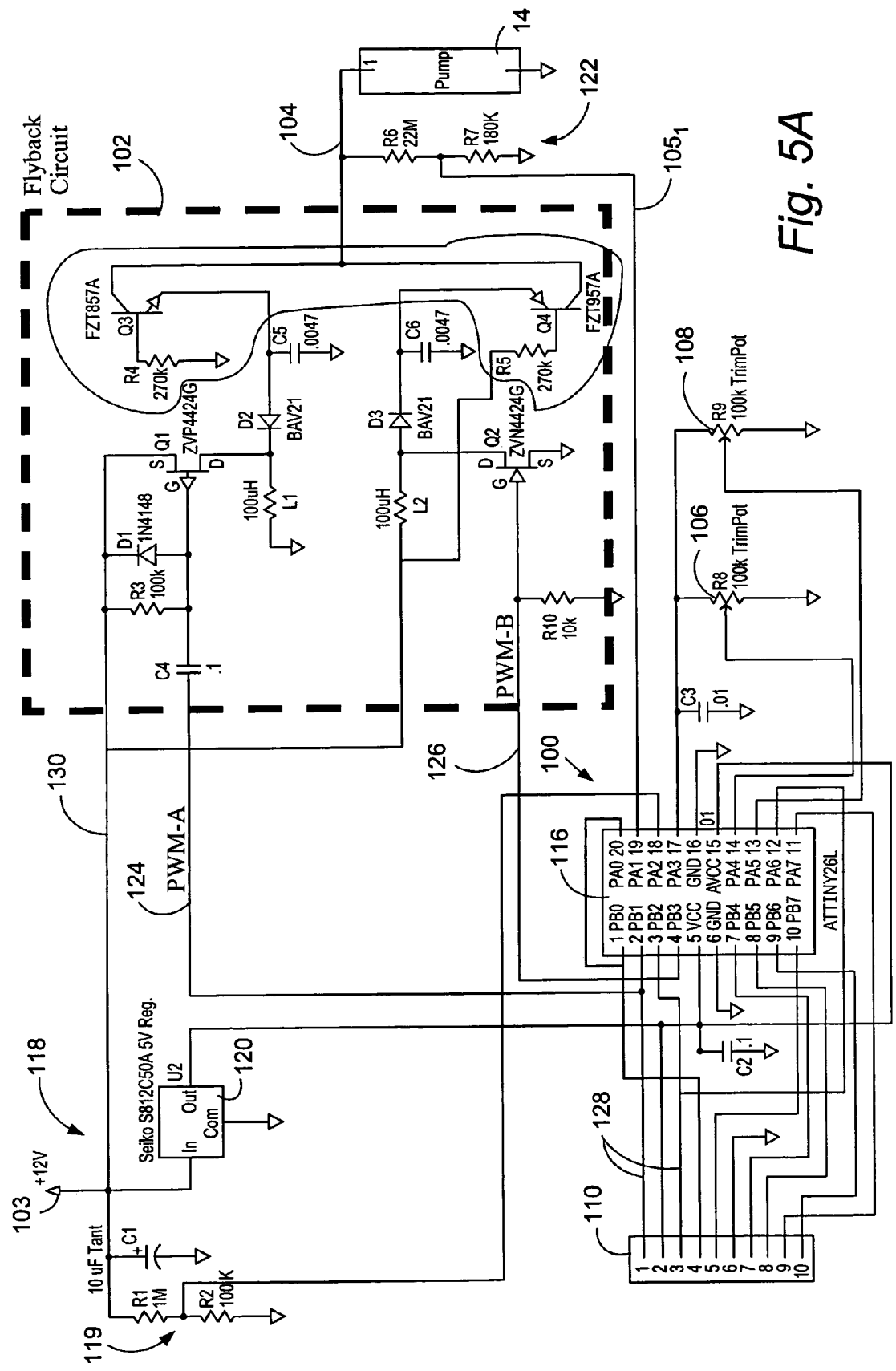
FIG. 5A is a detailed schematic view of an example, non-limiting piezoelectric actuator drive circuit.

In the example embodiment of FIG. 5A, piezoelectric actuator drive circuit 18 comprises pulse generator 100; converter circuit 102; and piezoelectric actuator 14. The converter circuit 102 uses the digital pulses produced by pulse generator 100 to produce high voltage, short period pulses (charge packets). As explained hereinafter, piezoelectric actuator 14, by its capacitive nature, integrates the charge packets to yield a drive field that preferably approximates a sine wave. While the capacitance of the piezoelectric actuator is essentially fixed, by controlling the generator digital pulses (e.g., varying a pulse width modulation duty cycle) on a pulse by pulse basis, waveforms of arbitrary complexity can be produced.

In the non-limiting example embodiment of FIG. 5A, the pulse generator 100 comprises a microcontroller-based pulsed width modulator (PWM) circuit (with one or more microcontrollers 116) and the converter circuit 102 comprises a flyback circuit. The flyback circuit 102 produces potentials that are bipolar with respect to an electrical ground. Preferably the frequency of the charge packets produced by the flyback circuit 102 is greater than of the ability of the piezoelectric actuator 14 to mechanically respond so that the pulses produced by flyback circuit 102 do not contribute to one of mechanical inefficiency and noise in piezoelectric actuator 14. Advantageously, in the embodiment of FIG. 5A neither a bridge converter circuit nor a charge storage circuit need be connected between the flyback circuit 102 and piezoelectric actuator 14.

In an illustrated, non-limiting embodiment, pulse generator 100 is shown as including a microcontroller 116. It should be understood that pulse generator 100 may comprise one or more microcontrollers or processors and/or other circuits. In addition, certain operations or functionalities herein ascribed to microcontroller 116 can also be considered to be performed by one or more processors, including but not limited to a microprocessor which comprises microcontroller 116. In this regard, for example, in the embodiments/modes of FIG. 3I(2) and FIG. 3I(3), the pulse generators 100(2) and 100(3) may include plural or even y number of microcontrollers for controlling the respective y number of piezoelectric actuators $14(x)_y$. Alternatively, the pulse generators 100(2) and 100(3) for the embodiments/modes of FIG. 3I(2) and FIG. 3I(3) may include a suitable microcontroller with multitasking capability and differing output pin arrangement for driving the y number of piezoelectric actuators $14(x)_y$.

The piezoelectric actuator drive circuit 18 is connected to a power supply 103. The piezoelectric actuator drive circuit 18 comprises a power supply monitor 118. The power supply monitor 118 includes an input voltage divider network 119 (which comprises resistors R1 and R2 connected in series between power supply 103 and ground); input capacitance C1 connected between power supply 103 and ground; and, voltage input regulator 120. The voltage divider network formed by resistors R1, R2 serves to generate an analog input to microcontroller 116 (applied at pin 18) for monitoring the input supply voltage. This allows microcontroller 116 to make adjustments via software to maximize the overall circuit performance for varying supplies. Capacitor C1 filters the main supply from power supply 103. The voltage input regulator 120 has an input terminal connected to pulse generator 100, and an output terminal connected to pin 15 of microcontroller 116.

Advantageously, the piezoelectric actuator drive circuit 18 can receive inputs including user input and external sensor input. To this end, two example user input devices 106 and 108 in the form of respective potentiometers (trimpots) R8 and R9 are connected between pins 17 of microcontroller 116 and ground. A greater or lesser number of user input devices can be provided. A connector 110 has leads connected to certain pins of microcontroller 116. As explained above, some of the pins in connector 110 may be connected to a source (such as a computer or one or more sensors) which produces signals which may be utilized by microcontroller 116 in shaping the waveform of the drive signal applied on line 104. The number of such external sensors can be variable in accordance with user desire and/or application or environment of use of pump 10.

An output monitor 122 in the form of a feedback voltage division network (which comprises resistors R6 and R7) is connected between the drive signal applied on line 104 and ground. A node of the feedback voltage division network between resistors R6 and R7 is connected to pin 19 of microcontroller 116.

As understood from the foregoing, the pulse generator 100 can be a microcontroller. Yet the pulse generator 100 can also be any ASIC or any other device or circuit which generates pulses suitable for use by flyback circuit 102 and piezoelectric actuator 14 for the general purposes herein described. In the illustrated, non-limited example embodiment, the pulse generator 100 is a microcontroller 116 such as an ATTINY26L microcontroller.

Pin connections for the microcontroller 116 of the illustrated embodiment are now briefly described. Pins 1, 2, 3 and 4 serve double duty as in-circuit programming pins and the functions described below. For example, pins 2 & 4 are the outputs of a software-controlled pulse width modulator embodied in microcontroller 116 and are used to drive flyback circuit 102. In particular, a signal PWM-A is output from pin 2 on line 124 to flyback circuit 102; a signal PWM-B is output from pin 4 on line 126 to flyback circuit 102. The pulse width-modulated signal PWM-A comprises positive digital pulses such as those shown in FIG. 4A as having period P and (positive) pulse width W. The pulse width-modulated signal PWM-B comprises negative digital pulses such as those shown in FIG. 4B as also having period P and (negative) pulse width W.

Pins 2 & 3 provide for a 2-wire serial interface buss 128 to microcontroller 116 for communications with other systems (for example, via buss 128 an array of pumps can be remotely controlled by another system such as a desktop computer). Pin 5 is connected to an output terminal of voltage input regulator 120 and to a filter "bypass" capacitor C2. Pins 7, 8, 9, 11, 12, and 20 are general purpose input/output pins that provide for external analog and/or digital communications so that various things such as temperature or pressure sensors can be attached to the pump to control its operation. Pins 13 & 14 are the input signals from user input device 108 and user input device 106, respectively. Pin 17 provides access (e.g., for user input device 106 and user input device 108) to the analog reference bandpass reference voltage of microcontroller 116. Capacitor C3 connected between pin 17 and ground is a bypass capacitor for the analog reference voltage for the analog to digital converter of microcontroller 116. Pin 18 is the analog input from power supply monitor 103, and is connected to a node between resistor R1 and resistor R2 of input voltage divider network 119. Pin 19 is the analog input for the output monitor 122 and is connected to a node between resistor R6 and resistor R8 of the voltage division network which comprises output monitor 122.

The flyback circuit 102 comprises transistor Q1, transistor Q2, transistor Q3, and transistor Q4. In the illustrated embodiment, the transistors are metal oxide semiconductor field effect transistors (MOSFET). The pulse width modulated signal PWM-A output from pin 2 of microcontroller 116 is applied on line 124 and via capacitor C4 to the gate of transistor Q1; the pulse width modulated signal PWM-B output from pin 4 of microcontroller 116 is applied on line 126 to the gate of transistor Q2. A resistor R10 connected between line 126 and ground serves as a pull down to increase noise immunity.

The source of transistor Q1 is connected by line 130 to power supply 103. The drain of transistor Q2 is connected by line 132 and through inductor L2 to power supply 103. The source of transistor Q2 is connected to ground.

Resistor R3 and diode D1 are connected between lines 124 and 130. Capacitor C4, resistor R3, and diode D1 serve to bias the output of microcontroller 116 up to one microcontroller output voltage level below the main supply voltage so that microcontroller 116 can turn transistor Q1 on and off even when the main supply voltage greatly exceeds the supply voltage of microcontroller 116.

The drain of transistor Q1 is connected to ground through inductance L1 and to an cathode of diode D2. The cathode of diode D2 is connected both to ground through snubber capacitor C5 and to the emitter of transistor Q3. The drain of transistor Q3 is connected through resistor R4 to ground. The collector of transistor Q3 is connected to the piezoelectric actuator 14 via line 104.

The emitter of transistor Q4 is connected by line 132 and through inductor L2 and diode D3 to power supply 103. The anode of diode D3 is connected to inductor L2 and to the drain of transistor Q2. The cathode of diode D3 is connected to ground through snubber capacitor C6 and to the emitter of transistor Q4. The gate of transistor Q4 is connected through resistor R5 to line 132. The collector of transistor Q3 is connected to piezoelectric actuator 14 via line 104.

Transistor Q1, transistor Q2, inductor L1, inductor L2, diode D2, and diode D3 are the primary components for generating the positive and negative high voltage flyback pulses as described above. The capacitors C5 and C6 are "snubber" capacitors which bring the fundamental frequency component of the flyback pulses within the frequency response capability of control transistors Q3 & Q4.

Transistor Q3, transistor Q4, resistor R4, and resistor R5 form a steering circuit for the flyback voltage, preventing charge cross-conduction that would otherwise render the circuit dysfunctional.

Resistors R6 and R7 form a voltage divider for output monitor 122, and serve to allow microcontroller 116 to monitor the output voltage and thus regulate the drive voltage. Regulation of the drive voltage is accomplished by microcontroller 116 varying the pulse widths W of the pulse bursts applied as PWM-A on line 124 and as PWM-B applied on line 126 (see FIG. 4B). The actual drive signal applied on line 104 is in essence derived from the pulse width modulated signals applied to converter circuit 102, e.g., signal PWM-A applied on line 124 and signal PWM-B applied on line 126.

3.2 First Example Drive Circuit: Operation

In operation, the pulse generator 100 (e.g., microcontroller 116) of piezoelectric actuator drive circuit 18 generates output pulses. Specifically, in the embodiment illustrated in FIG. 3, during a first half or positive half of a pulse cycle (e.g., first half cycle) the microcontroller 116 generates a pulse width modulation signal PWM-A on line 124 such as that shown in FIG. 4A. Then, during a second half or negative half of the cycle (e.g., second half cycle) the microcontroller 116 generates a corresponding pulse width modulation signal PWM-B on line 126 such as that shown in FIG. 4B. The entire cycle corresponds to a frequency or period P or PumpRate which, in one example embodiment, can be a user input value.

Figure 4B:
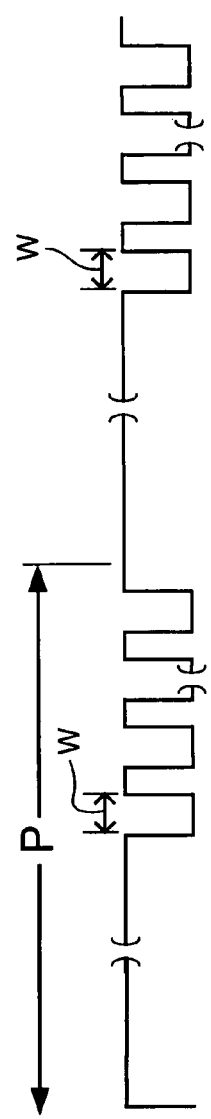

The flyback circuit 102 is driven by the signals PWM-A and PWM-B which are generated by microcontroller 116. In the illustrated embodiment, the signals PWM-A and PWM-B are variable frequency pulse trains at a frequency of 125 KHz. In typical operation of a pump being driven at say 60 Hz, for the first half cycle a burst of pulses lasting approximately 1/120 of a second would be sent on line 124 as PWM-A while the signal for PWM-B on line 126 is held at ground (turning transistor Q2 "off"). Examples of the series of digital pulses applied as PWM-A on line 124 are shown in FIG. 4A. Conversely, for the second half cycle the PWM-A signal on lie 124 is held high (turning transistor Q1 off) and an identical series of drive pulses is sent to transistor Q2 as signal PWM-B on line 126. Examples of the series of digital pulses applied as PWM-B online 126 are shown in FIG. 4B.

As explained herein after, the pulse width of the digital pulses applied as signal PWM-A on line 124 and as signal PWM-B on line 126 can be controlled by microcontroller 116 in accordance with one or more factors. For example, the excitation voltage and the reversal frequency can be dynamically manipulated based on either external control signals or on parameters being monitored locally such as actuator load, actuator resonance, pump pressure, temperature, etc. In addition, in one example mode, the period P of the signals PWM-A and PWM-B can be adjusted if desired as hereinafter discussed.

The PWM-A digital pulses applied from microcontroller 116 on line 124 to flyback circuit 102 cause transistor Q1 to switch on and off. When on, transistor Q1 causes magnetic flux to be stored in inductor L1. Immediately after transistor Q1 turns off, the stored flux causes a negative "flyback" voltage to be generated which is captured by diode D2 and capacitor C5, forcing transistor Q3 into conduction and thus the captured charge is further distributed to pump 10 and to piezoelectric actuator 14 in particular.

At the end of the first half cycle, e.g., at the end of the 1/120 second period, the signal PWM-A on line 124 is held high (turning transistor Q1 off) and an identical series of drive pulses is sent as signal PWM-B on line 126 to transistor Q2, generating a series of positive flyback pulses from inductor L2. These flyback pulses are fed to pump 10 via diode D3, capacitor C6, and transistor Q4. These positive pulses first serve to discharge the negative charge in the pump in a controlled fashion and then build a positive charge in the pump.

Thus, the pulse generator 100 applies digital pulses to flyback circuit 102. Flyback circuit 102 receives the digital pulses and produces charge packets (e.g., 35). The charge packets output by converter circuit 102 on line 104 appear essentially in a manner comparable to those illustrated in FIG. 4C, having a frequency F and an amplitude. The amplitude of the charge packets is related to the pulse width W of the PWM pulses applied on lines 124 and 126 to converter circuit 102.

The repeating flyback or charge packets applied on line 104 build a charge in the pump's capacitance, i.e., in piezoelectric actuator 14, resulting in the signal on line 104 taking the form of a voltage curve approximating a sine wave. In other words, the piezoelectric actuator is used to integrate the positive charge packets and the negative charge packets to shape a waveform of the drive signal. The aforedescribed period is repeated over and over, with the result that pump 10 "sees" a drive signal on line 104 that approximates a 60 Hz sine wave in the manner shown in FIG. 4D. The feedback signal from output monitor 122 applied to pin 19 of microcontroller 116 is the integrated voltage. The 125 KHz pulse frequency is completely filtered out by the pump because of its vastly slower-than-125 KHz response time.

Thus, the flyback circuit 102 applies charge pulses, e.g., charge packets, to piezoelectric actuator 14 which are integrated by piezoelectric actuator 14 into an electric field. The piezoelectric actuator 14 converts the charge packets into a lower frequency excitation signal. In other words, by building electrical charge in piezoelectric actuator 14 (e.g., by adding more or less charge), the piezoelectric actuator 14 participates in building the waveform in the piezoelectric actuator 14. By such integration the piezoelectric actuator 14 essentially serves as a charge storage device for power supply 103. In essence, the piezoelectric actuator 14 acts much like a filter capacitance in a power supply.

The charge generating components transistor Q1, inductor L1, transistor Q2, & inductor L2 are always being driven digitally (either on or off) and are thus operating at maximum efficiency (switching power supply theory). Yet pump 10 "sees" a sine wave drive waveform. This is achieved with an absolute minimum number of parts by using the piezoelectric actuator 14 itself as the primary charge storage device in this pseudo switching power supply design.

The fastest components of the flyback signal are "snubbed" out by capacitor C5 and capacitor C6. The majority of the flyback high frequencies are filtered by the pump itself. The PWM/flyback frequency of 125 KHz is at least two orders of magnitude above the pump's ability to mechanically respond.

Thus, the piezoelectric actuator drive circuit 18 uses the pump capacitance itself, e.g., the capacitance of piezoelectric actuator 14, as an integral part of a switching-type drive supply circuit.

In an aspect of an embodiment thus far described, piezoelectric actuator drive circuit 18 can be a microcontroller-based pulsed width modulator (PWM) circuit which is used to drive a flyback circuit that very uniquely has the ability to produce potentials that are bipolar with respect to system ground. Neither a bridge switching circuit nor a charge storage circuit are employed. Instead, the flyback circuit switches between producing positive pulses and negative pulses at a rate that equals the desired drive frequency of the actuator. For circuit efficiency and EMI reduction, some of the higher frequency components of the pulses are capacitively filtered. The pulses are then passed directly to the piezoelectric actuator and are integrated by the capacitive nature of the piezoelectric actuator to yield a drive field that very nearly approximates a sine wave. The frequency of the flyback pulses is designed to be greater than the ability of the actuator to mechanically respond so that the flyback pulses do not contribute to mechanical inefficiency or noise in the actuator.

FIG. 3I shows a variation of the piezoelectric actuator drive circuit 18. In particular, piezoelectric actuator drive circuit 18(3A) of FIG. 3I drives several piezoelectric elements at one time at the same voltage and frequency. As basically illustrated in FIG. 3I, microcontroller 116 supplies the signal PWM-A on line 124 and the signal PWM-B on line 126 to plural flyback circuits $102_1$ through $102_n$. Each of the plural flyback circuits $102_1$ through $102_n$ applies the drive signal on respective lines $104_1$ through $104_n$ to corresponding piezoelectric actuators $14_1$ through $14_n$. The piezoelectric actuator drive circuit 18 insures that the piezoelectric actuators of the plural pumps are phased properly for multiple diaphragm pump applications. Either phasing can be achieved by reversing the PWM signals.

3.3 Second Example Drive Circuit: Structure

Figure 5B:
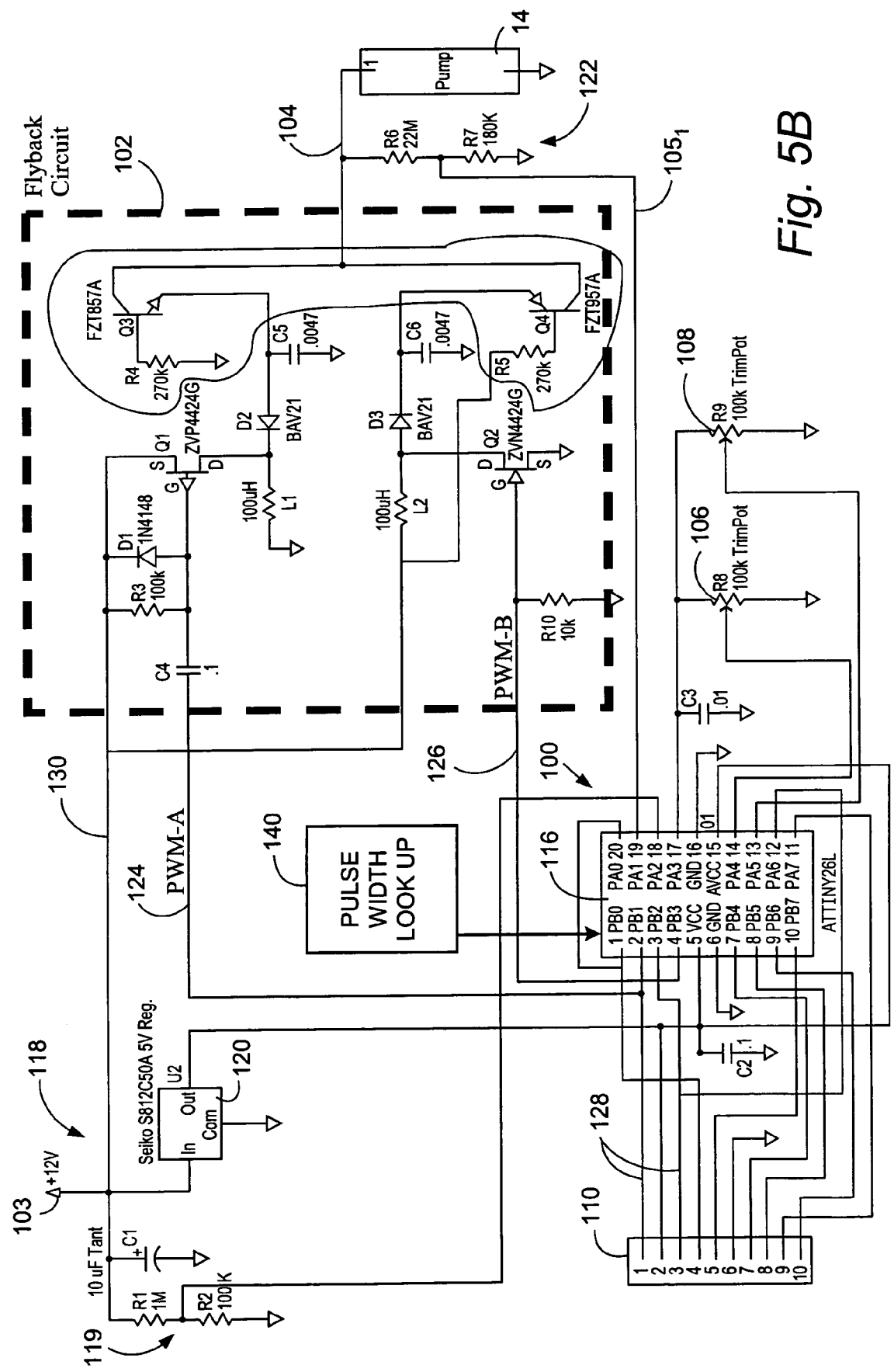
FIG. 5B is a detailed schematic view of an example, non-limiting piezoelectric actuator drive circuit showing inclusion of a PWM lookup table.
Figure 5C:
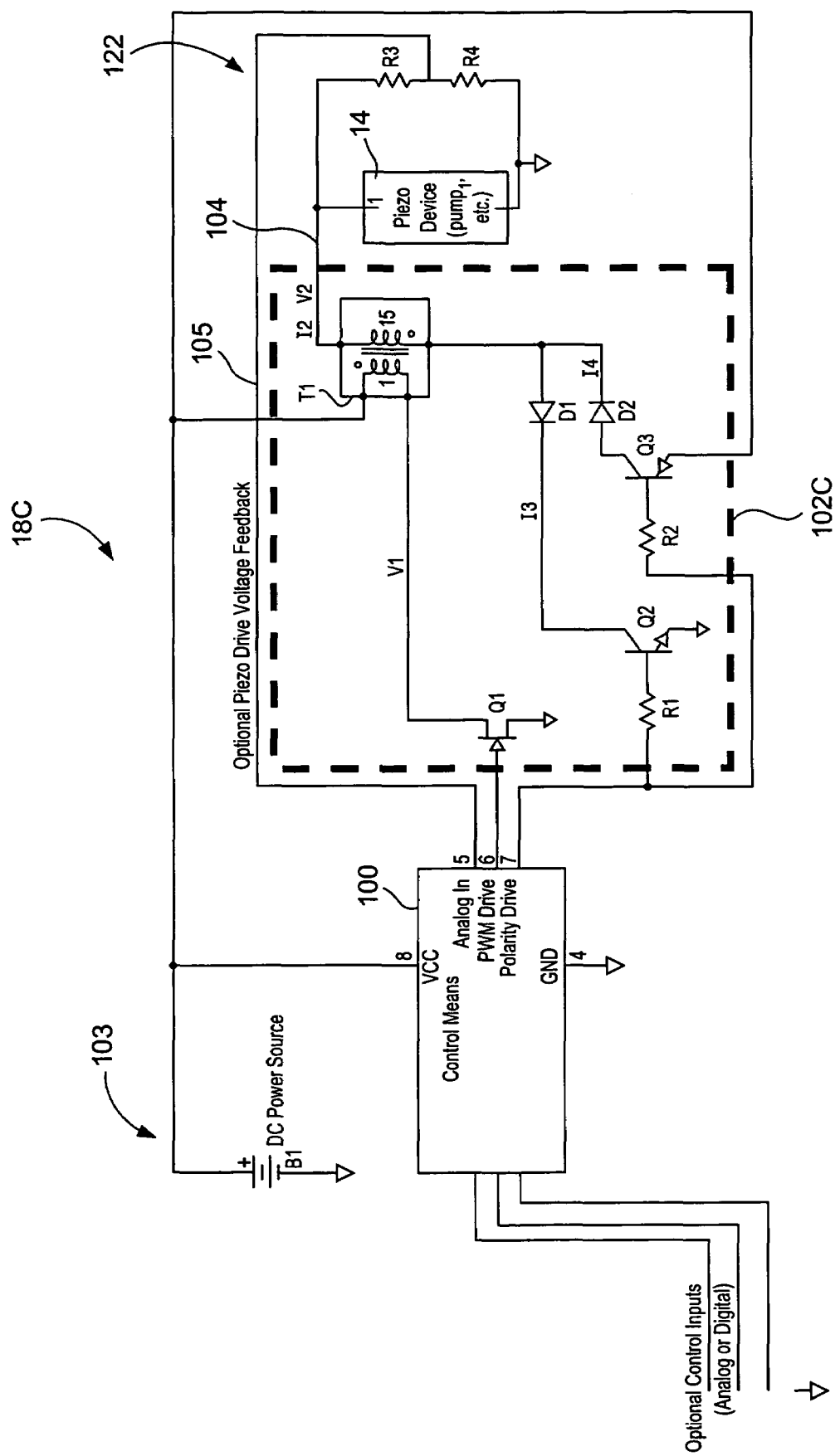
FIG. 5C is a detailed schematic view of another example, non-limiting piezoelectric actuator drive circuit.
Figure 5D:
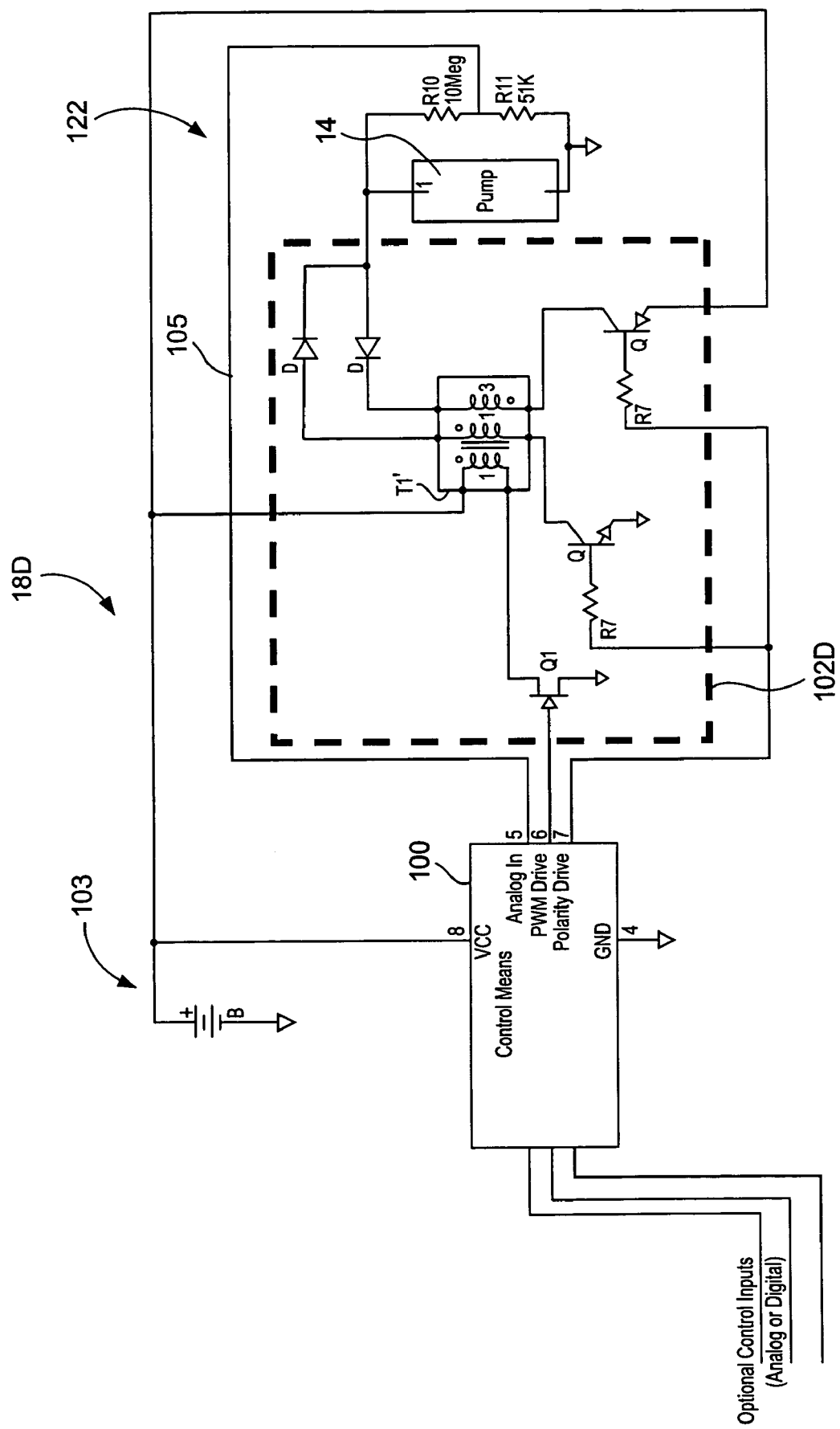
FIG. 5D is a detailed schematic view of an example variation of the piezoelectric actuator drive circuit of FIG. 5C.

FIG. 5C shows another implementation of a drive circuit 18C which also can be utilized with all embodiments of FIG. 3 and FIG. 3A, FIG. 3B, FIG. 3C, FIG. 3D, FIG. 3E(1), FIG. 3E(2), FIG. 3F, FIG. 3G, FIG. 3H(1), FIG. 3H(2), FIG. 3I(1), FIG. 3I(2), FIG. 3I(3), and FIG. 3J. As shown in FIG. 5C, piezoelectric actuator drive circuit 18C comprises pulse generator 100; converter circuit 102C; and piezoelectric actuator 14. The converter circuit 102C uses the digital pulses produced by pulse generator 100 to produce high voltage, short period pulses (charge packets). In similar manner as previously described, piezoelectric actuator 14, by its capacitive nature, integrates the charge packets to shape the waveform of the drive signal on line 104. Preferably, the piezoelectric 14 actuator integrates the charge packets to yield a drive field that generally approximates a sine wave.

In the non-limiting example embodiment of FIG. 5C, the pulse generator 100 comprises a microcontroller-based pulsed width modulator (PWM) circuit. As previously explained, it should be understood that pulse generator 100 may comprise one or more microcontrollers or processors and/or other circuits. In addition, certain operations or functionalities herein ascribed to microcontroller can also be considered to be performed by one or more processors, including but not limited to a microprocessor. Rather than a microcontroller or the like, pulse generator 100 can also be any ASIC or any other device or circuit which generates pulses suitable for use by converter circuit 102 and piezoelectric actuator 14 for the general purposes herein described.

The drive circuit 18C can be utilized with all embodiments, including those which drive single piezoelectric actuators as well as those driving plural piezeo electric actuators. Again with regard, for example, to the embodiments/modes of FIG. 3I(2) and FIG. 3I(3), the pulse generators 100(2) and 100(3) may include plural or even y number of microcontrollers for controlling the respective y number of piezoelectric actuators $14(x)_y$. Alternatively, the pulse generators 100(2) and 100(3) for the embodiments/modes of FIG. 3I(2) and FIG. 3I(3) may include a suitable microcontroller with multitasking capability and differing output pin arrangement for driving the y number of piezoelectric actuators $14(x)_y$.

The piezoelectric actuator drive circuit 18C is connected to a power supply 103. A power supply monitor, understood with reference to the previous embodiment, can also be included.

Advantageously, the piezoelectric actuator drive circuit 18C can receive inputs including user input and external sensor input. The potential inputs received by piezoelectric actuator drive circuit 18C include all those previously described in conjunction with FIG. 3 and FIG. 3A, FIG. 3B, FIG. 3C, FIG. 3D, FIG. 3E(1), FIG. 3E(2), FIG. 3F, FIG. 3G, FIG. 3H(1), FIG. 3H(2), FIG. 3I(1), FIG. 3I(2), FIG. 3I(3), and FIG. 3J. Included but not limited to these inputs are input from user input devices 106 and 108, other signal sources, external sensors, and the like. In addition, the piezoelectric actuator drive circuit 18C can optionally have the output monitor 122 with a voltage feedback signal provided on line 105 to pulse generator 100.

The pulse generator of the piezoelectric actuator drive circuit 18C generates a single PWM pulse train, rather than the dual PWM pulse trains of the piezoelectric actuator drive circuit 18A of FIG. 5A, for example. While much of the discussion herein references PWM digital pulses PWM-A and PWM-B of the FIG. 5A embodiment, it should be understood that any such reference equally applies to the single PWM pulse train output by the pulse generator of the piezoelectric actuator drive circuit 18C of FIG. 5C.

The piezoelectric actuator drive circuit 18C generates a bipolar drive signal on line 104 for application to a piezoelectric actuator 14 or other capacitive load. A typical but non-limiting application of piezoelectric actuator drive circuit 18C is to drive a piezoelectric pump from a 5 volt DC power source, generating an excitation voltage on the piezoelectric actuator that is roughly a 60 Hz sine wave swinging from +300 volts to −100 volts.

The piezoelectric actuator drive circuit 18C uses a unipolar power source. The converter circuit 102C comprises a modest-voltage, power switching element Q1 and a transformer T1 that has only one secondary with no taps and yet it generates a high voltage bipolar output. The converter circuit 102C functions in conjunction with a single unipolar pulse source and a single unipolar polarity control signal are required for operation. In the illustrated implementation, the pulse generator 100 serves both as the unipolar pulse source and the source of the unipolar polarity control signal. In addition, the pulse generator receives the feedback signal from piezoelectric actuator 14 on line 105.

The converter circuit 102C further comprises transistors Q2 and Q3. The gates of transistors Q2 and Q3 are connected via resistors R1 and R2, respectively, to the source of the polarity drive signal. The emitter of transistor Q3 is connected to power source 103, the collector of transistor Q3 is connected via diode D2 to the secondary of transformer T1. In FIG. 5C, current I4 depicts the current between the secondary of transformer T1 and diode D2. The collector of transistor Q2 is connected via diode D1 to the secondary of transformer T1. In FIG. 5C, current I3 depicts the current between the collector of transistor Q2 and diode D2.

In piezoelectric actuator drive circuit 18C, polarity switching is achieved by current (as opposed to voltage) control on the "slow side" of the transformer T1 secondary. This permits the use of very low-cost, slow, high-voltage transistors that are mass produced. Furthermore, only a single, low potential, low frequency, unipolar steering signal is required for operation. Such simplicity is in contrast to more expensive SCRs or MOSFETS or transistors with possibly multiple, more complex, higher voltage drive and biasing requirements.

Bipolar voltage generation is achieved in the piezoelectric actuator drive circuit 18C by catching the "resonant bounce" electromotive force (emf) of transformer T1 on the half cycle that is generated by the parasitic capacitance of the transformer windings. Paradoxically, parasitic capacitance in transformers is generally considered to be a design impediment that reduces the efficiency of tranformers and their associated circuits. Yet the piezoelectric actuator drive circuit 18C ingeniously and uniquely uses the parasitic capacitance of the transformer T1 to generate an opposing emf. Advantageously, this allows the transformer T1 to be fabricated at very low cost. Alternatively, a 2 secondary transformer (or tapped secondary) transformer such as that shown as T1' in piezoelectric actuator drive circuit 18D of FIG. 5D can be utilized. Elements of piezoelectric actuator drive circuit 18D of FIG. 5D which are common to those of piezoelectric actuator drive circuit 18C of FIG. 5C are comparably numbered. While usage of the transformer T1 of FIG. 5C is preferable, the piezoelectric actuator drive circuit 18D of FIG. 5D with its transformer T1' is nevertheless quite useful, especially in view of the polarity switching considerations which are common to both piezoelectric actuator drive circuit 18C and piezoelectric actuator drive circuit 18D.

3.4 Second Example Drive Circuit: Operation

The piezoelectric actuator drive circuit 18C of FIG. 5C operates in two modes, the mode being determined by the logic level of the polarity drive signal applied to converter circuit 102C. The relation of the polarity drive signal to the output polarity is determined by the winding sense of the transformer primary to secondary. The physics of some example piezoelectric actuators require that the actuator be driven with a higher positive than negative potential (e.g. +300, −100). The parasitic/resonant bounce technique afforded by the piezoelectric actuator drive circuit 18C naturally produces a higher potential when catching the primary flyback emf than when catching the "bounce". Therefore, for efficiency and convenience, the transformers utilized herein are wound such that the drive circuit operates as described below. Other configurations are certainly possible and within the purview of the embodiments described herein.

Figure 20B:
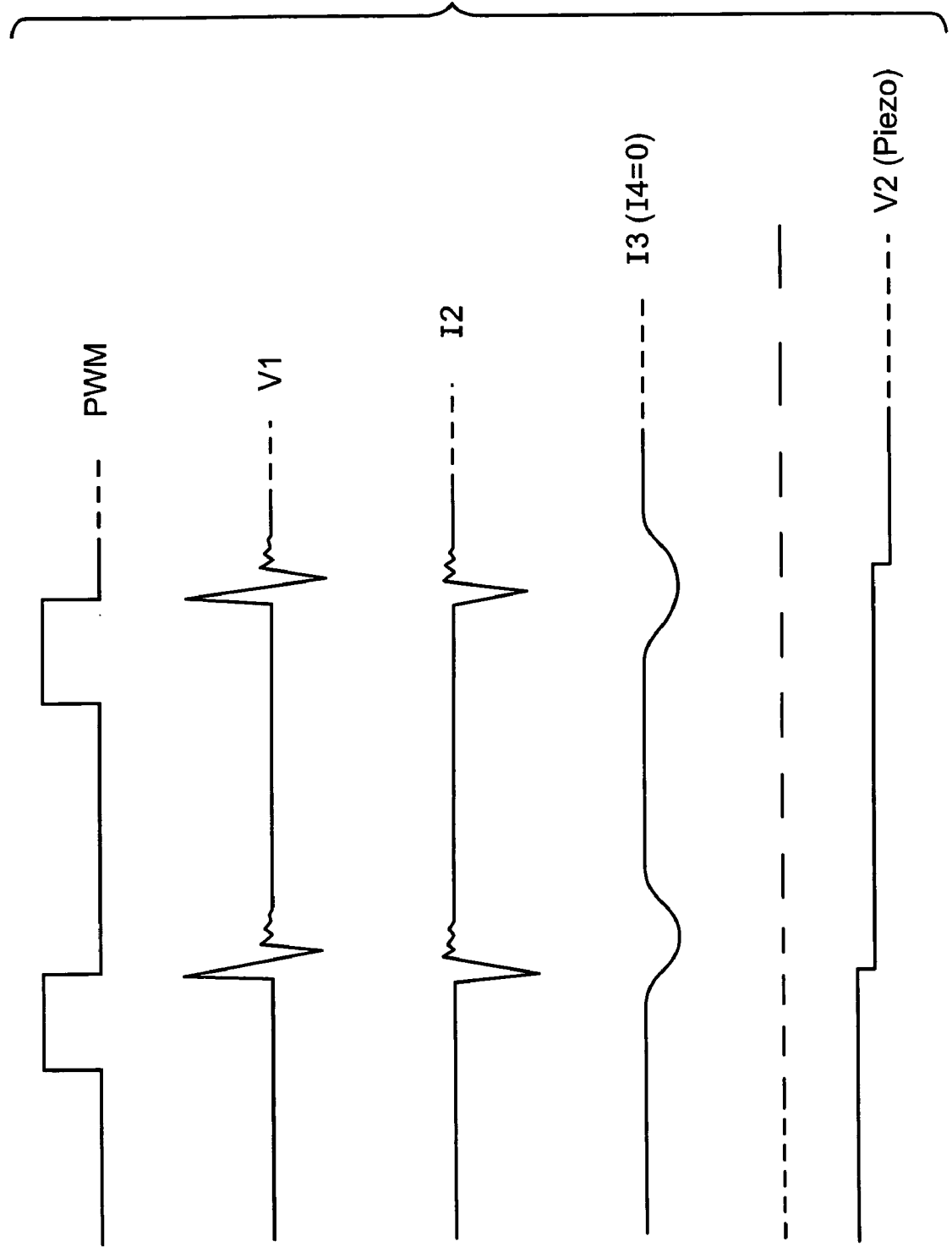
FIG. 20B shows signal diagrams for a second mode of operating the piezoelectric actuator drive circuit of FIG. 5C.

FIG. 20A shows signal diagrams for a first mode of operating the piezoelectric actuator drive circuit 18C of FIG. 5C. In the first mode, the polarity drive signal is low, resulting in a positive going piezo drive wave. FIG. 20B shows signal diagrams for a second mode of operating the piezoelectric actuator drive circuit 18C of FIG. 5C. In the second mode, the polarity drive signal is high, resulting in a negative going piezo drive wave. It will be understood that the piezoelectric actuator drive circuit 18D of FIG. 5D can be similarly operated.

In the first mode of operation illustrated in FIG. 20A, pulse generator 100 generates an input level (e.g. 5 volts) pulse train whose pulse width my be optionally modulated at "PWM Drive". Such a pulse train is shown by the signal PWM in FIG. 20A. The polarity drive signal is low, so that transistor Q3 is "on" and thus current may flow in diode D2 as needed. When the PWM drive pulse is high, transistor Q1 is "on" and current flows in the primary of transformer T1, storing magnetic flux in the transformer core.

At the end of each high pulse of the signal PWM, transistor Q1 turns "off" and the primary of transformer T1 reacts by generating a "flyback" positive charge pulse on the primary (V1) and secondary (V2) (v=di/dt). In the illustrated, example embodiment, the secondary is wound in a 15:1 ratio to the primary so that the induced voltage at V2 is 15 times greater than V1. Because transistor Q3 is forward biased, current is able to flow out of I2 (on line 104) to the piezoelectric actuator 104, and a positive step (S+) in the potential on the piezoelectric actuator results. In an example implementation, the PWM drive pulses occur at about 100 KHz. The individual pulse widths of these PWM pulses can be modulated such that any positive direction amplitude/wave shape can be induced on the piezoelectric actuator 14.

Figures 10A, 10B:
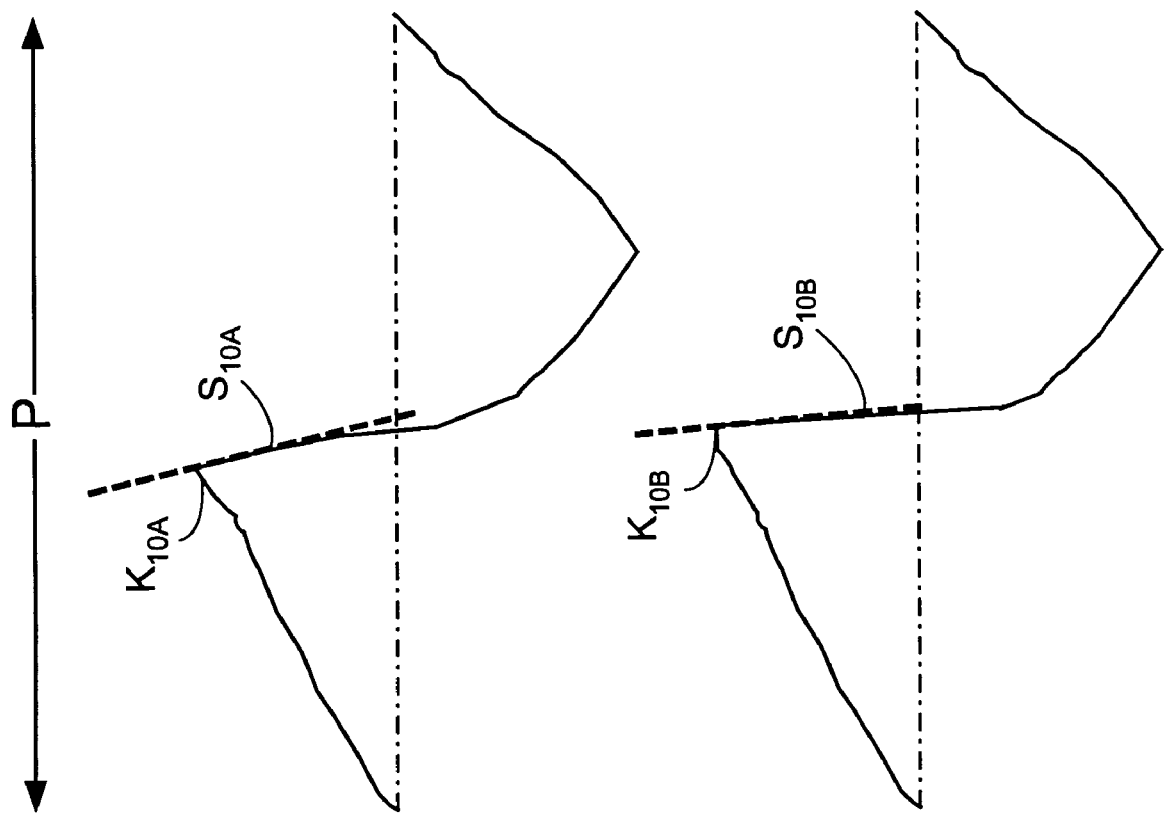
FIG. 10A and FIG. 10B are diagrammatic views of two waveforms which illustrate principles involved in determination of capacitance of a piezoelectric actuator.

In the second mode of operation illustrated in FIG. 10B, pulse generator 100 generates an input level (e.g. 5 volts) pulse train whose pulse width my be optionally modulated at "PWM Drive". This is in like manner as the first mode, but the PWM pulse widths may be different. In the second mode, the polarity drive signal is high, so transistor Q2 is "on" and thus current may flow in diode D1 as needed. When the PWM Drive pulse is high, transistor Q1 is "on" and current flows in the primary of transformer T1, storing magnetic flux in the transformer core.

At the end of each high pulse, transistor Q1 turns "off" and the primary of transformer T1 reacts by generating a "flyback" positive charge pulse on the primary (V1) and secondary (V2) (v=di/dt), as in the first mode. However, in the second mode transistor Q3 is "off", and thus current cannot flow in diode D2, nor will it flow in diode D1 due to its direction. This causes the flyback potential to be "trapped" in the transformer T1 and partially dissipated in transformer resistive losses, with the rest being stored in the parasitic capacitance of transformer T1. The parasitic capacitance and the transformer inductance form an LC resonant circuit which shortly thereafter responds by producing a "bounce" charge at V2 which is opposite in polarity. Because of its new polarity, current can now flow out of the piezoelectric actuator 14 and through diode D1 and transistor Q2, inducing a negative direction step in the potential on the piezoelectric actuator 14. The individual pulse widths of the PWM drive pulses can be modulated such that any negative direction amplitude/wave shape can be induced on the piezoelectric actuator 14.

Thus, by appropriately modulating the duty cycle and/or frequency of PWM drive and polarity drive signal, using the piezoelectric actuator drive circuit 18C (or piezoelectric actuator drive circuit 18D) virtually any desired bipolar waveform can be induced on a piezoelectric or other capacitive load.

4.0 Example: Drive Circuit Receiving Analog Input

In an embodiment such as that illustrated in FIG. 3B, for example, the piezoelectric actuator drive circuit 18 receives user input through user input device 106 and user input device 108. In a particularly illustrated implementation, the user input device 106 is a trimpot which can be used to set a period/frequency of the drive signal applied on line 104, and user input device 108 is a trimpot which can be used to set a voltage/amplitude of the drive signal applied on line 104. Analog signals from user input device 106 and user input device 108 are applied to pins 14 and 13, respectively, of microcontroller 116, and ultimately affect the voltage and frequency of the drive signal applied on line 104. The drive signal applied on line 104 to piezoelectric actuator 14 is based on the digital PWM-A and PWM-B signals output from microcontroller 116, so that the drive signal applied on line 104 is itself digital. Thus, the signals produced by user input device 106 and user input device 108 and applied to microcontroller 116 are two examples of analog input signals in accordance with which the microcontroller 116 generates a digital drive signal. The analog input signals are applied to an internal (multichannel) analog to digital converter (ADC) of the microcontroller 116. It will be appreciated that comparable user input devices can be utilized to supply parameters or criteria other than frequency/period and amplitude/voltage to piezoelectric actuator drive circuit 18.

5.0 Drive Signal: Fixed PWM Mode

As mentioned above, in one illustrated embodiment the drive signal applied on line 104 to piezoelectric actuator 14 is based on the digital PWM-A and PWM-B signals output from microcontroller 116. In a PWM servo mode of operation described hereinafter, the pulse widths of the pulse width modulation signals PWM-A and PWM-B applied to converter circuit 102 can be changed, even dynamically changed in real time operation of pump 10, in order to change the waveform of the drive signal applied to piezoelectric actuator 14. But in another embodiment known as the fixed PWM mode, the logic (e.g., software) executed by pulse generator 100 is configured so that the pulse widths of the signals PWM-A signal PWM-B are uniform.

The fixed PWM mode may be selectively entered and exited during operation of piezoelectric actuator drive circuit 18, as in the case of determining the resonance of piezoelectric actuator 14. On the other hand, in certain "fixed" applications in which the pulse width of the signals PWM-A and PWM-B are expected never to change, the operating parameters for the piezoelectric actuator 14 (e.g., pulse width, frequency of the drive signal) may be stored in non-volatile storage. For example, the operating parameters necessary for the fixed PWM mode may be "burned in" to microcontroller 116 at manufacturing time, at application time, or for that matter, at any time. Thus, microcontroller 116 can be configured to work in essentially any application.

6.0 Drive Signal: Optimized Waveform Mode

Figure 12:
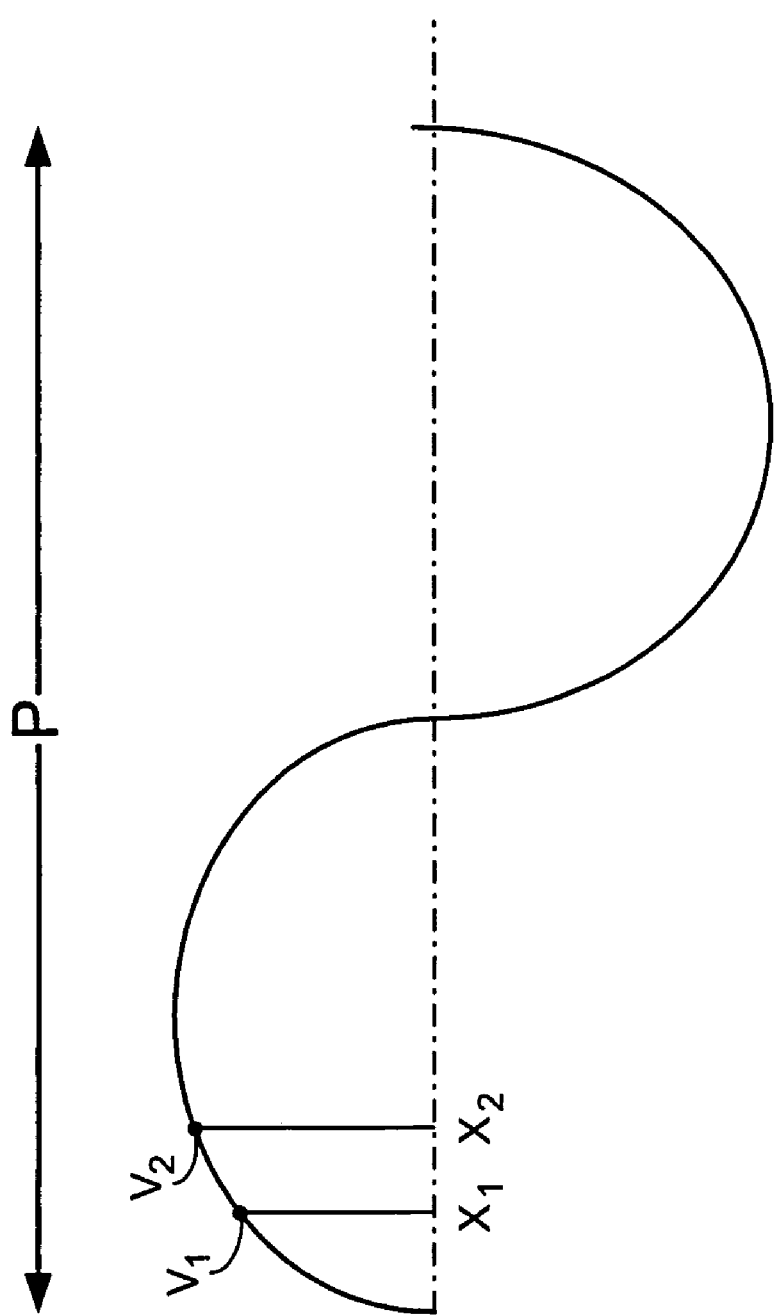
FIG. 12 is a diagrammatic view of an optimized waveform for a drive signal for a piezoelectric pump.

The piezoelectric actuator drive circuit can also operate in an optimized waveform mode. In the optimized waveform mode, the piezoelectric actuator drive circuit 18 uses pre-stored values to maintain an essentially constant waveform shape. The example sinusoidal waveform shown in FIG. 12 serves to illustrate a 360 degree period waveform having points $X_1, X_2, \ldots$, etc., with each point corresponding to a degree or a fraction of a degree of one period. At each point X the waveform has a corresponding (voltage) amplitude V. For example, at point $X_1$ the waveform of FIG. 12 has an amplitude $V_1$.

In the optimized waveform mode, certain values utilized to generate the drive signal having the optimized waveform are prepared and pre-stored in a table (such as lookup table 140 of FIG. 5B) for use by pulse generator 100 in generating the drive signal for the piezoelectric actuator 14. In one implementation representatively illustrated by table 140-

18A of FIG. 18A, the pre-stored values which yield the optimized waveform are the amplitude values themselves (e.g., values $V_1$, $V_2$, etc., associated with corresponding points $X_1$, $X_2$, etc.).

In another implementation representatively illustrated by table 140-18B of FIG. 18B, the pre-stored values which yield the optimized waveform are or include the pulse width modulation values for each of the points $X_1$, $X_2$, etc., which yield the desired respective amplitudes and hence the desired overall waveform. In other words, in the second implementation of the optimized waveform mode, the lookup table 140-18B is utilized to determine the pulse width to be utilized for the signals PWM-A and PWM-B on line 124 and 126 at selected intervals or points along the waveform through its period P. This implementation version of the optimized waveform mode thus resembles the fixed PWM mode in that the pulse widths of the signals PWM-A and PWM-B on line 124 and 126, respectively, are pre-stored at least for initial use. These pre-stored PWM values either may or may not be dynamically adjusted subsequently on the basis of an input signal (e.g., not on the basis of a sensor input signal or a user input signal).

As an example of the foregoing, at a point $X_1$=P/20 a first value from PWM lookup table 140 is utilized for the pulse width of the PWM-A signal, at a point $X_2$=2*P/20 a second value from PWM lookup table 140 is utilized for the pulse width of the PWM-A signal, and so forth. At the half way point, e.g., point 10*P/20 in this example, the signal PWM-B is utilized rather than the PWM-A signal, in which case an appropriate value for PWM-B is garnered from PWM lookup table 140, followed at point 11*P/20 with another corresponding value for PWM lookup table 140, and so forth.

The lookup table 140 thus comprises a pairing of waveform points and appropriate pulse width values (any particular pulse width value being either for the PWM-A signal or the PWM-B signal, as discussed above). As discussed further herein, the pulse width values stored in PWM lookup table 140 can be predetermined or "optimized" in accordance with the particular pump with which the piezoelectric actuator is being utilized, in accordance with a particular environment in which the pump is utilized, in accordance with one or more criteria (e.g., sensor input values), and/or one or more of the foregoing.

The lookup table 140 is preferably stored in non-volatile memory. Typically the lookup table 140 is stored in microcontroller 116. Alternatively, for some applications lookup table 140 may also be external to microcontroller 116. The illustration of lookup table 140 in FIG. 5B is intended to encompass any manner of providing lookup table 140 for piezoelectric actuator drive circuit. While the optimization described herein is in context of one particular example of a pump as a utilization device, optimization of waveforms for other piezoelectric-utilizing devices is also encompassed and implementation evident herein.

7.0 Drive Signal Control Program: Overview

Basic example steps of one example mode of logic implemented by microcontroller 116 in handling the input signals such as the analog input signals received from user input device 106 and user input device 108, as well as the fixed PWM mode and the PWM servo modes of operation, are understood in conjunction with FIG. 6 and FIG. 6A–FIG. 6G. The logic implemented by microcontroller 116 can be in the form of programmable instructions (e.g., a drive signal control program 150) which are executed by microcontroller 116. Alternatively, comparable instructions can be performed with microcontroller 116 taking the form of a general purpose computer, using an application specific integrated circuit (ASIC), and/or using one or more digital signal processors (DSPs). It should be understood that the steps of the drive signal control program 150 described herein, as well as steps of any constituent routine or other routine, are merely for sake of example and can be implemented or accomplished using various other logic and/or programming techniques.

As mentioned before, in the illustrated example the user input device 106 is a trimpot which can be used to set a period/frequency of the drive signal applied on line 104, and user input device 108 is a trimpot which can be used to set a voltage/amplitude of the drive signal applied on line 104. By "period" or "frequency" is meant a period such as that illustrated as P in FIG. 4A, e.g., the period consisting of an activation of the signal PWM-A followed by an activation of the signal PWM-B. In the logic of FIG. 6, the value input by user input device 106 is referred to as CheckRateInput, since the user input period also corresponds to the rate at which the pump is to operate. By "amplitude" or "voltage" is meant the amplitude or voltage A as shown in FIG. 4D which relates to (e.g., is derived from) the pulse width W of the signals PWM-A and PWM-B applied on lines 124 and 126, respectively, and which is also related to the duration that the flyback circuit 102 actually charges the inductor L1 (see FIG. 5A). In the logic of FIG. 6, the value input by user input device 108 to set the amplitude or voltage is referred to as SetVoltsInput.

7.1 Drive Signal Control Program: Main Routine

Figure 6A:
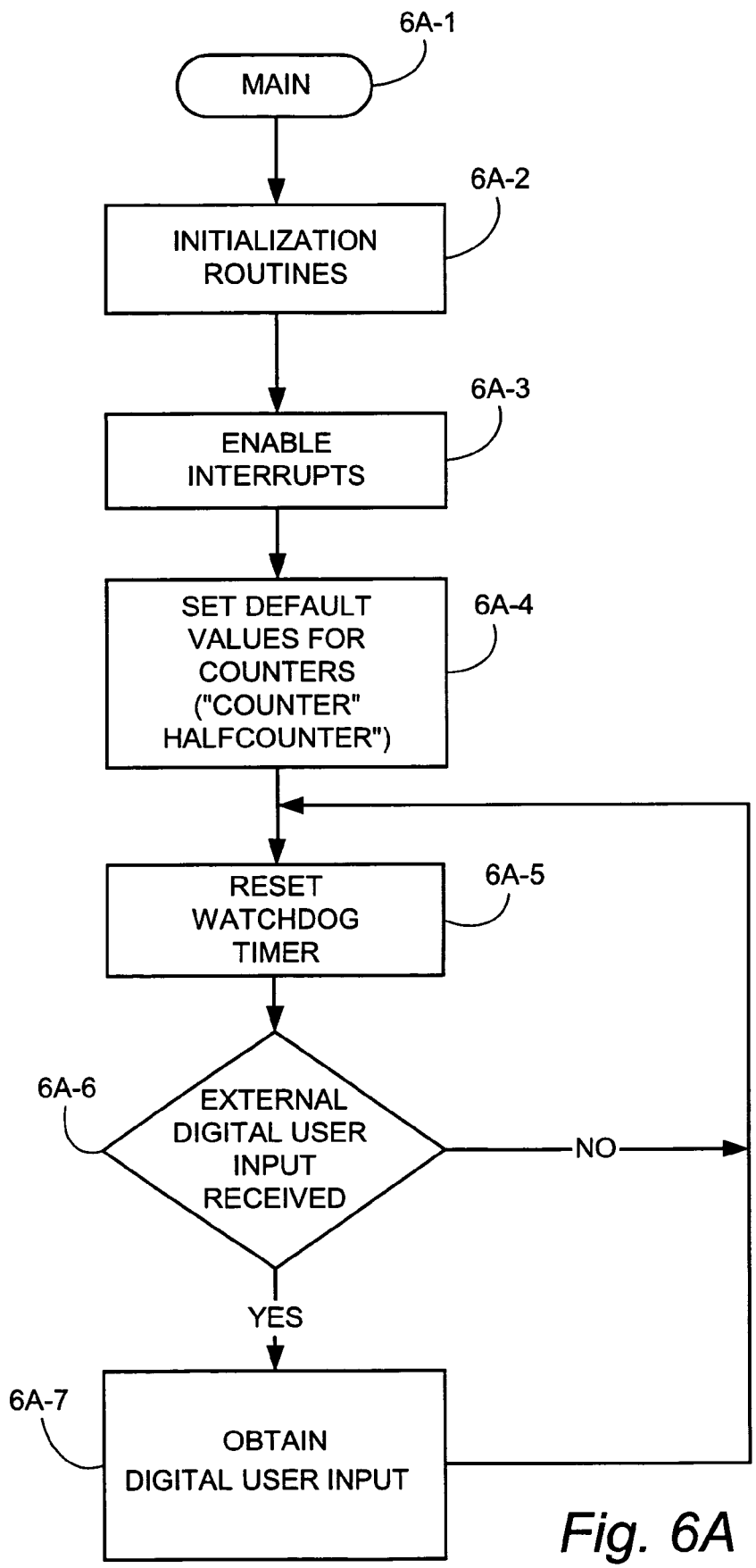

FIG. 6A shows selected basic steps involved in a main routine of drive signal control program 150. The main routine of FIG. 6A, entered at step 6A-1, basically concerns initialization and user interface monitoring. Step 6A-2 of the main routine generally depicts the main routine calling certain other initialization routines to initialize such things as ports, memory, timers (including an interrupt timer), channel selection of the on-board analog to digital converter (ADC), and certain PWM values. As step 6A-3 the main routine enables certain interrupts including an interrupt for an interrupt service routine hereinafter described with reference to FIG. 6B. In step 6A-4, the main routine sets default values for a period counter ("Counter") and half-period counter ("CounterHalf"). At step 6A-5 the main routine resets a watchdog timer so that the processor does not go into a reset stage.

At step 6A-6, the main routine checks to determine if an external user digital input has been received which affects operation of pump 10. Checking whether an external user digital input has been received can involve checking whether a start bit has been set on serial interface buss (Universal Serial Interface (USI) buss) 128. If external user digital input has been received, at step 6A-7 a routine is called to handle receipt of the external user digital input (a USI handler). If the determination at step 6A-6 is negative, and after execution of step 6A-7, execution returns to step 6A-6.

7.2 Drive Signal Control Program: Interrupt Service Routine

Figure 6B:
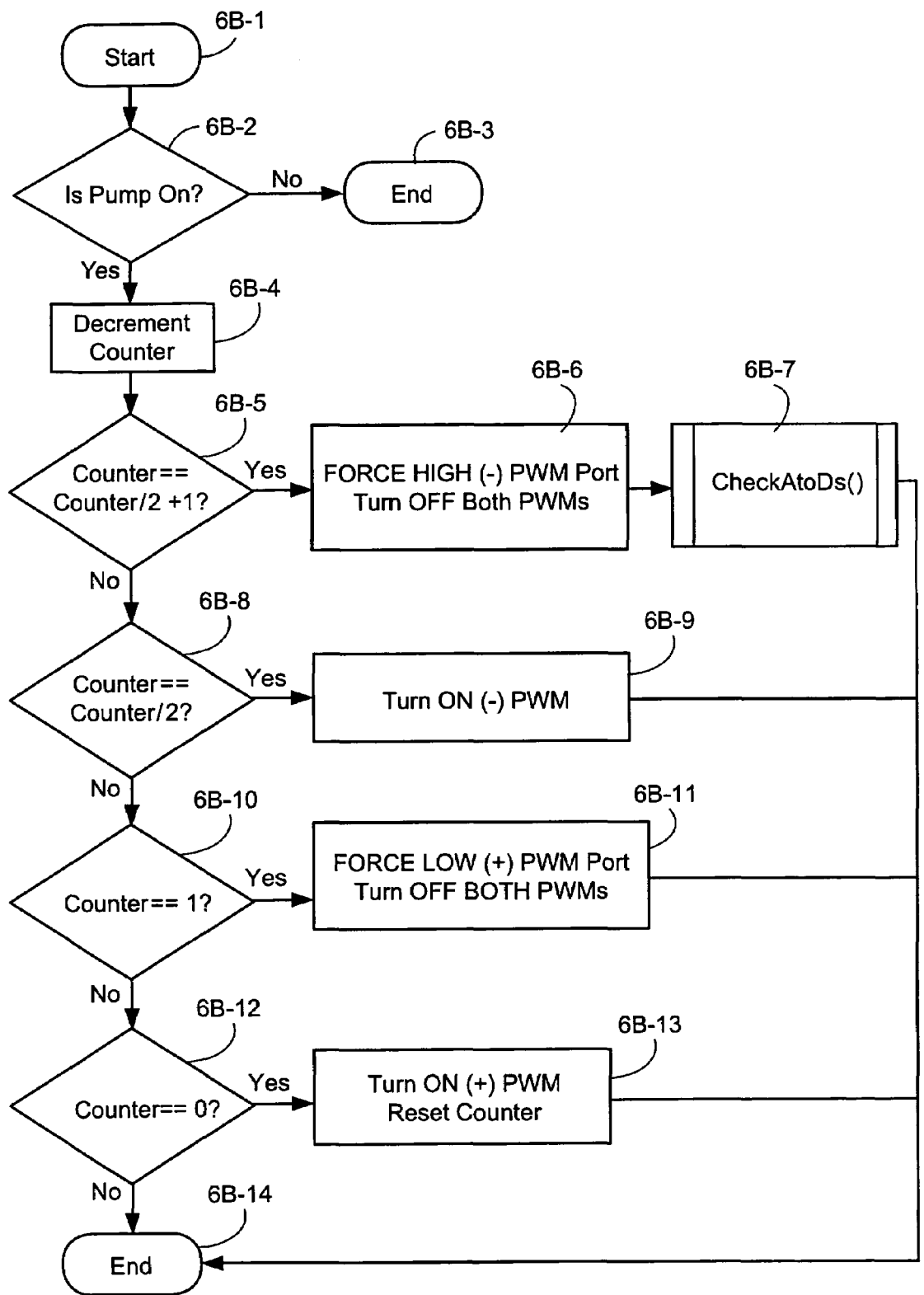

FIG. 6B shows basic steps involved in the interrupt service routine which has also been nicknamed as Timer 0 ISR. The interrupt service routine of FIG. 6B is executed 3906 times per second, and is entered at step 6B-1. The interrupt service routine of FIG. 6B is called every time an overflow occurs for the timer (Timer 0). In other words, in the illustrated embodiment, this overflow and thus invocation of interrupt service routine of FIG. 6B occurs at a rate of 3906 Hz.

Since operation of pump 10 can be terminated or shut off by software, a check occurs at step 6B-2 whether there has been a software termination of pump 10. In case of software termination, the interrupt service routine of FIG. 6B is also terminated as indicated at step 6B-3.

The interrupt service routine of FIG. 6B utilizes variables Counter and CounterHalf. Default values for variables Counter and CounterHalf are set at step 6A-4 of the main routine. Thereafter values for the variable Counter are reset (in accordance with user input, e.g. at user input device 108) by a CheckRateInput routine illustrated in FIG. 6G. Execution of the CheckRateInput routine illustrated of FIG. 6G obtains or computes a value CounterReset, which is used to reset the variable Counter. The value CounterReset is computed by dividing 3906 (the value timer T0) by the user-input value PumpRate which is acquired from user input device 106. Thus, Counter is reset as CounterReset=3906/PumpRate. After the variable Counter has been reset, the variable CounterHalf is reset as Counter/2.

The value of variable Counter affects the period or frequency of the drive signal (see FIG. 4A–FIG. 4D). In the present illustration the value of variable Counter depends on the value set by the user at user input device 106. As explained below, the counter Counter keeps track of frequency and actually tracks the waveform through construction of the charge packets of FIG. 4C.

When it is determined at step 6B-2 that operation of the pump is not to be terminated, the counter Counter is decremented at step 6B-4. Step 6B-5 involves checking whether the (just decremented) value of counter Counter corresponds to a point just shy of half of the waveform (e.g., whether Counter has reached the value CounterHalf+1).

If an affirmative determination occurs at step 6B-5, as step 6B-6 the interrupt service routine of FIG. 6B turns off both the signal PWM-A and the signal PWM-B on lines 124 and 126. It will be recalled that the signal PWM-A drives the piezoelectric actuator 14 in the positive direction, the signal PWM-B drives the piezoelectric actuator 14 in the negative direction. So as the midpoint of waveform of FIG. 4D is approached, both signal PWM-A and signal PWM-B are turned off.

The signal PWM-A and signal PWM-B are turned off just shy of midpoint of the waveform in order to prepare for ensuing step 6B-7. Step 6B-7 involves checking voltage obtained from the multichannel analog to digital converter ADC) of microcontroller 116. The PWM signals PWM-A and PWM-B are turned off in case they generate noise that might interfere with the voltage determinations from the ADC.

So as soon as the signal PWM-A and signal PWM-B are turned off at step 6B-6, a measurement of voltage is taken as quickly as possible at step 6B-7. The ADC reading of step 6B-7 is a reading of voltage applied to pump 10. This reading is taken to ensure that the pump is being driven at the desired set value of the amplitude. In other words, the reading at step 6B-7 is a reading of amplitude A of the drive signal of FIG. 4D as applied to pump 10. As previously explained, the voltage at output to the pump is obtained from voltage monitor 122, e.g. at midpoint of voltage divider which comprises R6 and R7 (see, e.g., FIG. 5A). The actual voltage applied to pump 10 (which could be as high as or in the vicinity of 400 volts or so) may not be readable on the ADC of microcontroller 116, for which reason the voltage divider of output monitor 122 brings the voltage down to a lower voltage (e.g., below 2.68 volts) for sake of microcontroller 106.

Thus, when an affirmative determination is made at step 6B-5 that a point just shy of mid-waveform has been reached, the signals PWM-A and PWM-B are turned off, and a sample taken of voltage to the pump 10 before exiting the interrupt service routine of FIG. 6B at step 6B-14. The sample of voltage is thus taken at the highest point on the waveform (closest to the peak as possible).

A negative determination at step 6B-5 means that the waveform is not at the sampling point (not just shy of the mid waveform point). When a negative determination is made at step 6B-5, a check is performed at step 6B-8 whether the value of decremented Counter is exactly equal to CounterHalf (meaning that the waveform has reached its exact midpoint). If the check at step 6B-8 is affirmative, as step 6B-9 the interrupt service routine of FIG. 6B prompts microcontroller 116 to turn on signal PWM-B (the negative PWM signal applied on line 126 to converter circuit 102) so that the negative series of charge packets of FIG. 4C can be formed. Thereafter the interrupt service routine of FIG. 6B is exited (step 6B-14).

If the check at step 6B-8 is negative (which means that waveform formation is past its midpoint), a check is made at step 6B-10 whether the value of Counter has reached 1. The Counter reaching 1 means that the negative pulse formation is essentially completed. Therefore, if the determination at step 6B-10 is negative, at step 6B-11 the interrupt service routine of FIG. 6B instructs microcontroller 116 to turn off both signal PWM-A on line 124 and signal PWM-B on line 126, at which point the interrupt service routine of FIG. 6B is exited (step 6B-14).

If the check at step 6B-10 is negative, a further check is made at step 6B-12 whether the decremented value of the Counter has reached zero. If so, it is time to start formation of a new waveform, and accordingly at step 6B-13 the interrupt service routine of FIG. 6B prompts microcontroller 116 to turn on the signal PWM-A for application on line 124 to start the positive portion of the new pulse (the new waveform will be formed during successive iterations of interrupt service routine of FIG. 6B). Then the interrupt service routine of FIG. 6B is exited at step 6B-14.

As an optional step, after turning off both signal PWM-A and signal PWM-B at step 6B-11, the voltage at the ADC of user input device 106 could again be checked in the manner of step 6B-7.

Figure 4C:
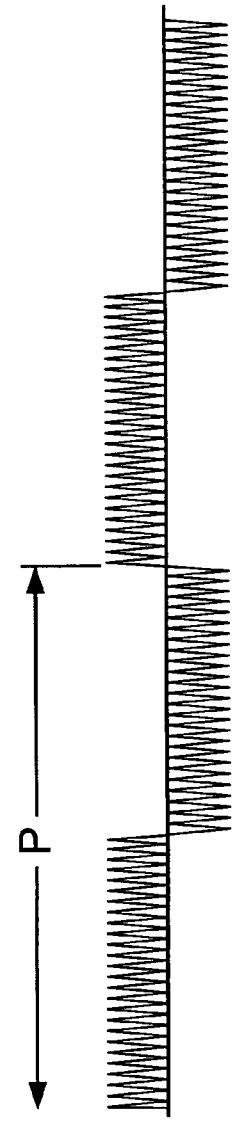
Figure 4D:
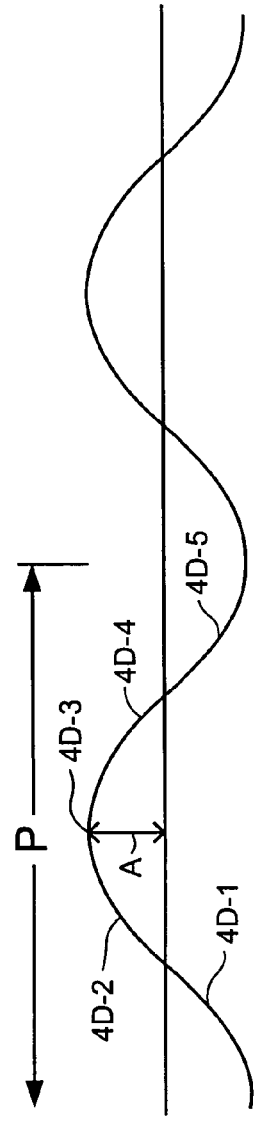

Thus, repeated performance of the interrupt service routine of FIG. 6B results in formation of the series of charge packets such as those of FIG. 4C which are applied on line drive signal applied on line 104 to piezoelectric actuator 14. The interrupt service routine of FIG. 6B controls the rate of the pump. The value of Counter is set by dividing the timer (Timer 0) frequency (e.g., 3906) by user-input value indicative of the desired rate (PumpRate). The value of Counter is decremented during each execution of interrupt service routine, and at each execution of interrupt service routine at least one of the comparisons of step 6B-5, step 6B-8, step 6B-10, and step 6B-12 are performed.

As a result of execution of interrupt service routine of FIG. 6B, one would expect that the signal applied on line 104 would appear as a series of positive charge packets, followed by a series of negative charge packets, the series being so arranged that the signal would have an overall square wave shape comparable to that of the envelope of the charge packets of FIG. 4C. In such case the charge packets shown in FIG. 4C would have an amplitude which is dependent on the user input value InputVolt and a period which depends on the user input value RateInput. But, as mentioned before, piezoelectric actuator 14 serves, e.g., to integrate the signal applied on line 104, so that, in at least one example implementation, the actual waveform on line 104 appears more like the sine waveform shown in FIG. 4D. While the waveform of the integrated signal in FIG. 4D has the same period as the signal of FIG. 4C, the integrated signal of FIG. 4D has more of a sinusoidal shape than a square shape. In particular, each cycle of pulses of the waveform of the integrated signal in FIG. 4D has a first positive sloping segment 4D-1, a second positive sloping segment 4D-2; a peak 4D-3, a first negative sloping section 4D-4, and a second negative sloping section 4D-5.

The integrated waveform shape is under the control of the drive circuit, particularly in view of the pulse width modulation (e.g., of the PWM-A and PWM-B signals on lines 124 and 126, respectively, in the circuit of FIG. 5A). While essentially sine-shaped waveforms are described herein, it is entirely possible that the drive circuit could sample the waveform after various (e.g., each and every) PWM pulse and adjust the PWM period to achieve other wave shapes, including complex waveform shapes.

7.3 Drive Signal Control Program: Checking ADC

Figure 6C:
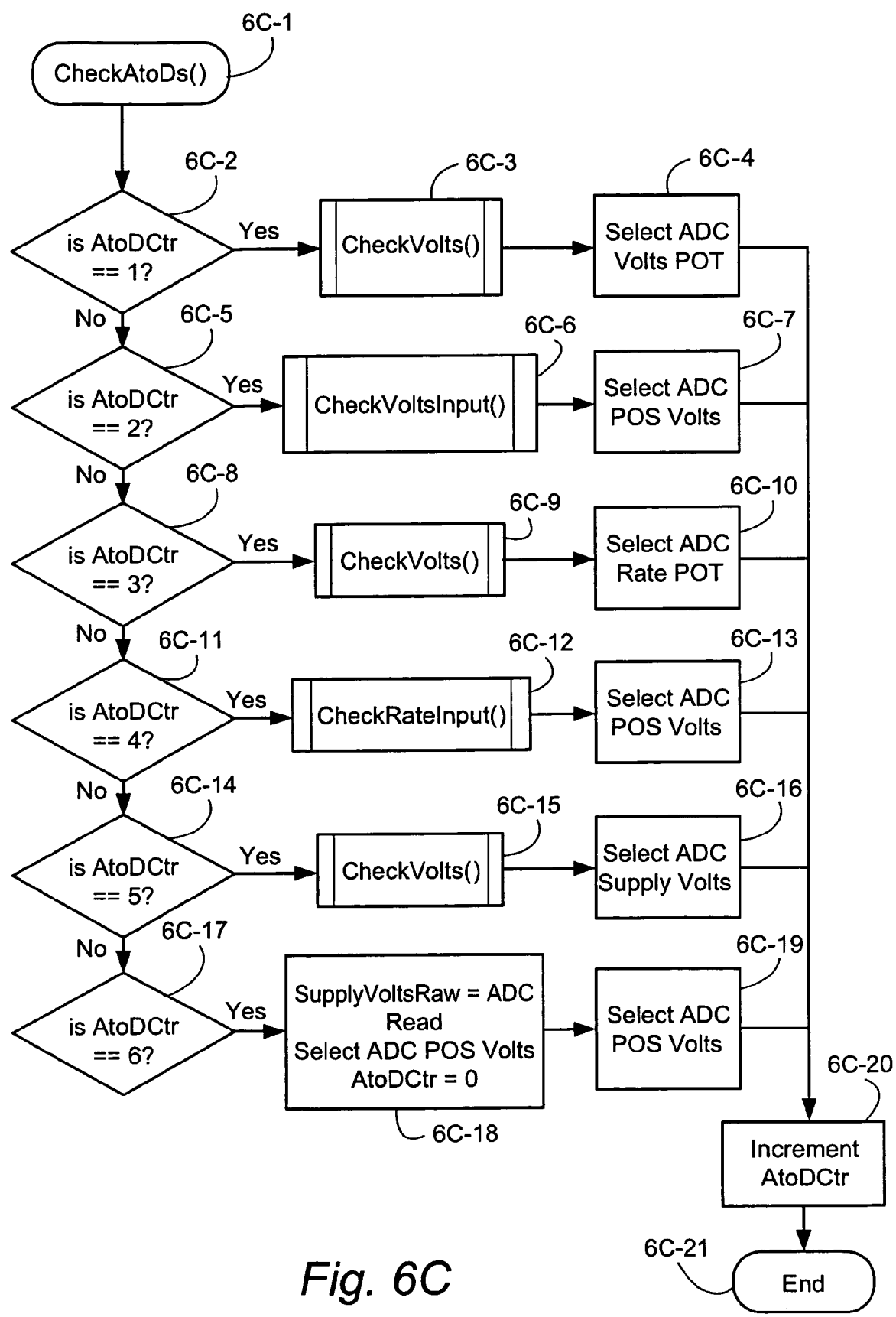

Aforedescribed step 6B-7 involved checking the analog digital converter (ADC) of microcontroller 116. Step 6B-7 essentially involves execution of a routine named CheckAtoDs. Selected basic example steps of routine CheckAtoDs are illustrated in FIG. 6C.

The routine CheckAtoDs is entered at step 6C-1. It will be recalled that the ADC of microcontroller 116 is a multichannel ADC, and as such can receive analog signals on several channels from a corresponding number of sources. For example, the multichannel ADC of microcontroller 116 receives a voltage feedback signal from output monitor 122 regarding the voltage on line 104 applied to piezoelectric actuator 14 of pump 10, and two distinct other voltage signals which are input from user input device 106 and user input device 108.

The routine CheckAtoDs is configured to check, in a predetermined sequence: a channel of its ADC which receives voltage from output monitor 122; a channel of its ADC which receives voltage from user input device 106 indicative of RateInput; a channel of its ADC which receives voltage from user input device 108 indicative of VoltInput; and, a channel of its ADC which receives a supply voltage from power supply 103. The sequencing of operation of routine CheckAtoDs is based on a counter AtoDCtr, which counts from 1 to 6 as it is incremented at step 6C-20.

At step 6C-2 of routine CheckAtoDs a check is performed whether the counter AtoDCtr currently has the value of one. If the check at step 6C-2 is affirmative, at step 6C-3 the routine CheckAtoDs processes the value previously read from a previously selected channel of the ADC of microcontroller 116. In particular, at step 6C-3 the routine CheckAtoDs calls routine CheckVolts. The routine CheckVolts actually processes the voltage feedback signal, now converted to digital by ADC of microcontroller 116, obtained from output monitor 122. The digital voltage value processed at step 6C-3 should correspond to the amplitude A of the drive signal at its peak (see FIG. 4D). If not, as hereinafter described the routine CheckVolts adjusts the pulse width of the signals PWM-A and PWM-B in order to achieve the desired amplitude for the drive signal applied on line 104. After calling routine CheckVolts to process the digitally converted feedback voltage signal, the routine CheckAtoDs prepares for its next execution by (at step 6C-4) selecting the channel of the ADC which handles user input device 108 so that at step 6C-4 the selected channel acquires the analog information applied thereto. Thereafter, routine CheckAtoDs increments the counter AtoDCtr (at step 6C-20) and is exited (step 6C-21).

If, upon entry into routine CheckAtoDs, the value of counter AtoDCtr is two (as determined at step 6C-5), the routine CheckAtoDs calls routine CheckVoltsInput in order for the channel of the ADC which handles the user input device 108 to process the analog value obtained from user input device 108 and read at the prior execution of step 6C-4. It will be recalled that the user-set value set at user input device 108 corresponds to VoltInput, and determines the pulse widths of digital pulses applied as signals PWM-A and PWM-B on lines 124 and 126, respective, and thus determines the amplitude of the drive signal on line 104. After enabling the appropriate channel of the ADC to read the analog value, at step 6C-7 the routine CheckAtoDs again selects the channel of the ADC which handles the reading of voltage from output monitor 122 (and thus the drive signal applied on line 104). The channel selection of step 6C-7 results in the selected channel reading the analog value applied thereto in preparation for the next execution of routine CheckAtoDs. Thereafter, the counter AtoDCtr is incremented (step 6C-20) and the routine CheckAtoDs is exited (step 6C-21).

If, upon entry into routine CheckAtoDs, the value of counter AtoDCtr is three (as determined at step 6C-8), at step 6C-9 the routine CheckAtoDs again calls routine CheckVolts in order to process the digitally converted feedback voltage acquired from output monitor 122 (which represents the actual amplitude of the voltage applied as the drive signal to piezoelectric actuator 14). If necessary, in its processing the routine CheckVolts adjusts the pulse width of the signals PWM-A and PWM-B in order to achieve the desired amplitude for the drive signal to piezoelectric actuator 14. Then the routine CheckAtoDs prepares for its next execution by (at step 6C-10) selecting the channel of the ADC which handles user input device 106 so that at step 6C-10 the selected channel acquires the analog information applied thereto. Thereafter, routine CheckAtoDs increments the counter AtoDCtr (at step 6C-20) and is exited (step 6C-21).

If, upon entry into routine CheckAtoDs, the value of counter AtoDCtr is four (as determined at step 6C-11), the routine CheckAtoDs calls routine CheckRateInput in order for the channel of the ADC which handles the user input device 106 to process the analog value obtained from user input device 106 and read at the prior execution of step 6C-10. It will be recalled that the user-set value set at user input device 108 corresponds to RateInput or PumpRate, and determines the frequency or period of the drive signal applied to piezoelectric actuator 14 on line 104. After enabling the appropriate channel of the ADC to read the analog value, at step 6C-13 the routine CheckAtoDs again selects the channel of the ADC which handles the reading of voltage from output monitor 122 (and thus the drive signal applied on line 104). The channel selection of step 6C-13 results in the selected channel reading the analog value applied thereto in preparation for the next execution of routine CheckAtoDs. Thereafter, the counter AtoDCtr is incremented (step 6C-20) and the routine CheckAtoDs is exited (step 6C-21).

If, upon entry into routine CheckAtoDs, the value of counter AtoDCtr is five (as determined at step 6C-14), at step 6C-15 the routine CheckAtoDs again calls routine CheckVolts in order to process the digitally converted feedback voltage acquired from output monitor 122 (which represents the actual amplitude of the voltage applied as the drive signal to piezoelectric actuator 14). If necessary, in its processing the routine CheckVolts adjusts the pulse width of the signals PWM-A and PWM-B in order to achieve the desired amplitude for the drive signal to piezoelectric actuator 14. Then the routine CheckAtoDs prepares for its next execution by (at step 6C-16) selecting the channel of the ADC which handles the supply voltage from power supply 103 so that at step 6C-16 the selected channel acquires the analog information applied thereto. Thereafter, routine CheckAtoDs increments the counter AtoDCtr (at step 6C-20) and is exited (step 6C-21).

If, upon entry into routine CheckAtoDs, the value of counter AtoDCtr is six (as determined at step 6C-17), at step 6C-18 the routine CheckAtoDs sets a variable SupplyVoltsRaw to the digitally converted value read at step 6C-16, and resets the value of counter AtoDCtr back to zero. Then, at step 6C-19, the routine CheckAtoDs again selects the channel of the ADC which handles the reading of voltage from output monitor 122 (and thus the drive signal applied on line 104). The channel selection of step 6C-19 results in the selected channel reading the analog value applied thereto in preparation for the next execution of routine CheckAtoDs. Thereafter, the counter AtoDCtr is incremented (step 6C-20) and the routine CheckAtoDs is exited (step 6C-21).

Thus, as seen from the foregoing and FIG. 6C, the routine CheckAtoDs calls the routine CheckVolts in order to assure that the drive signal to piezoelectric actuator 14 on line 104 has the proper or desired amplitude. In addition, the routine CheckAtoDs (at step 6C-6) calls the routine CheckVoltsInput to determine whether the user input voltage obtained from user input device 108 indicates that the desired amplitude of the drive signal has been changed by the user, and if so makes an adjustment in the desired amplitude. Similarly, the routine CheckAtoDs (at step 6C-12) calls the routine CheckRateInput to determine whether the user input voltage obtained from user input device 106 indicates that the desired frequency of the drive signal has been changed by the user, and if so makes an adjustment in the desired frequency.

7.4 Drive Signal Control Program: Check Volts Input Routine

Figure 6D:
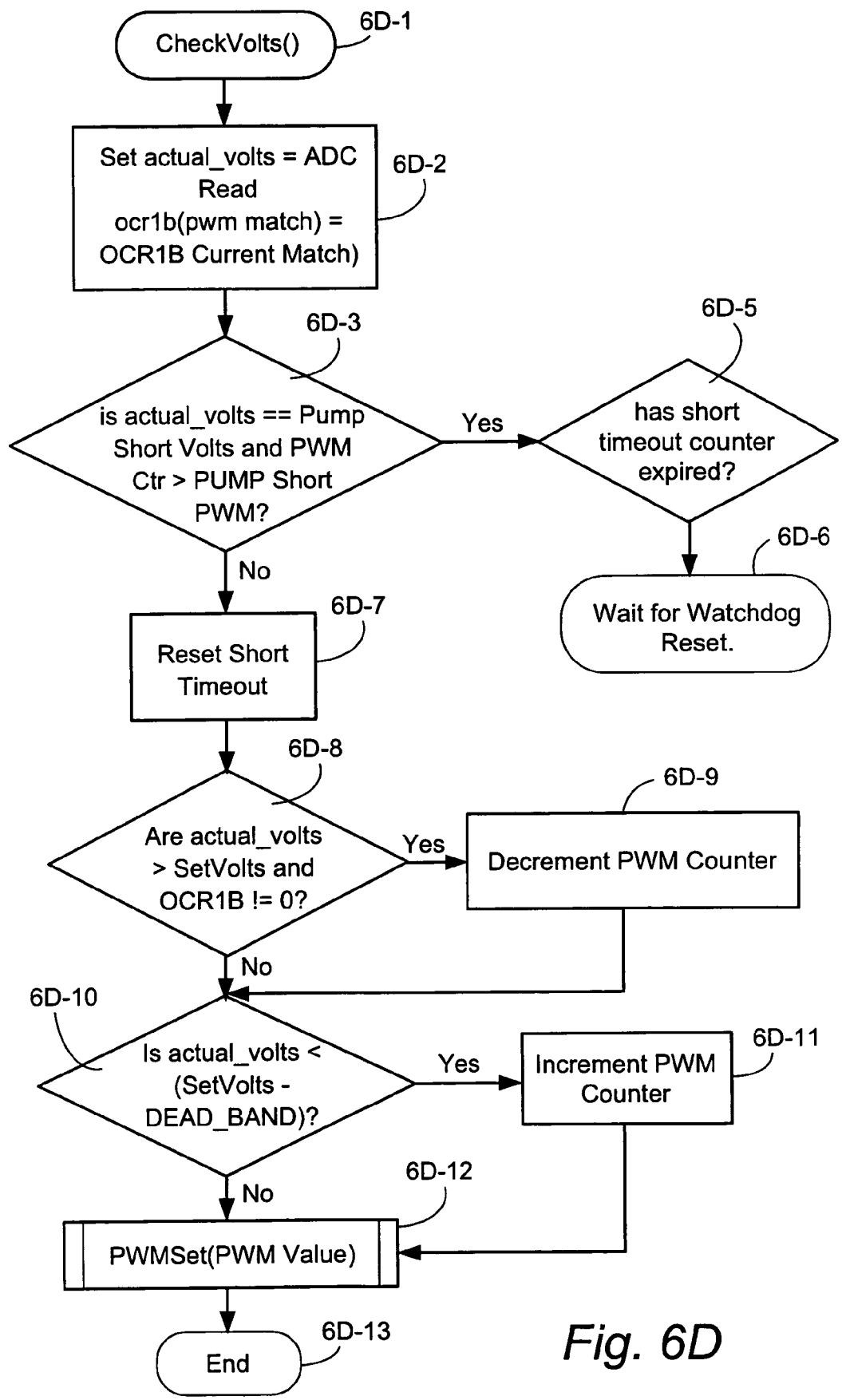

Basic steps in the routine CheckVoltsInput, called at step 6C-3, step 6C-9, and step 6C-15 of the routine CheckAtoDs, are illustrated in FIG. 6D. The routine CheckVoltsInput is entered at step 6D-1. Then, at step 6D-2, the (now digitally converted) voltage just read (at step 6C-19, step 6C-7, and step 6C-13, respectively) by the channel handling the output monitor 122 is set as the value of a variable actual_volts. A pump short circuit detection is performed at step 6D-3. If a short circuit condition is found to exist for pump 10, a reset of the watchdog timer is awaited (step 6D-6) after a short circuit timeout counter has expired (step 6D-5). If no short circuit is detected, the short circuit timer is reset at step 6D-7.

At step 6D-8 a check is made whether the value of the variable actual_volts exceeds a variable SetVolts. The value of the variable SetVolts reflects the actual desired amplitude for the drive signal for piezoelectric actuator 14 on line 104. The value of the variable SetVolts can be set by user input, e.g., either analog input such as the VoltInput provided by user input device 108, or from a GUI in the manner previously illustrated by the embodiment of FIG. 3C. In any event, if it is determined at step 6D-8 that the value of the variable actual_volts does exceed the value of the variable SetVolts, then a variable PWM counter is decremented at step 6D-9. On the other hand, if it is determined at step 6D-10 that the value of the variable actual_volts is less than or equal to the value of the variable SetVolts, then at step 6D-11 the variable PWM counter is incremented. After either decrementation (step 6D-9) or incrementation (step 6D-11) of the variable PWM counter, the value of the variable PWM counter is sent as value PWM to a routine PWM Set.

7.5 Drive Signal Control Program: PWM Setting Routine

Figure 6E:
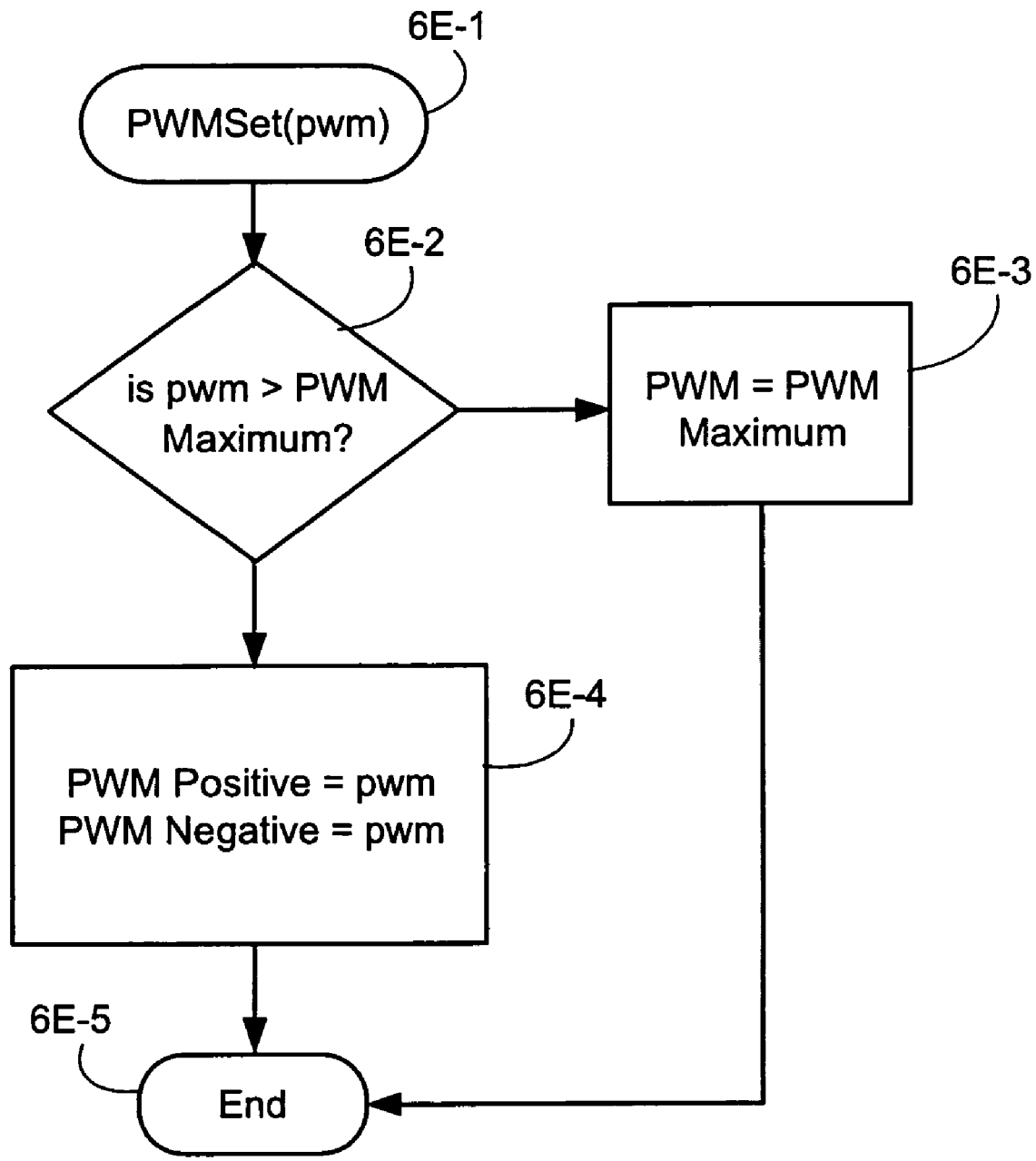

The routine PWM Set serves to adjust (either increase or decrease, as appropriate) the pulse width W of the digital pulses included in both signal PWM-A applied on line 124 and signal PWM-B applied on line 126 to converter circuit 102. It will be recalled that the pulse width W corresponds to the amount of time charge time that the inductor L1 of converter circuit 102 is being charged. Example basic steps of routine PWM Set are illustrated in FIG. 6E. The routine PWM Set is entered at step 6E-1. At step 6E-2 the routine PWM Set checks whether the variable PWM (obtained from the routine CheckVolts of FIG. 6D) has exceeded its permissible maximum (PWM maximum). If so, at step 6E-3 the variable PWM is set to PWM maximum, and the routine PWM Set thereafter exited at step 6E-6. If the variable PWM has not exceeded its permissible maximum, then at step 6E-4 the routine PWM Set sets the pulse width of both the signal PWM-A (PWM positive) and the signal PWM-B (PWM negative) to the value of PWM, so that the signals PWM-A and PWM-B will have the desired pulse width W (see FIG. 4A).

FIG. 7A–FIG. 7D illustrate how changing the pulse width of the signals PWM-A and PWM-B on lines 124 and 126 affect the drive signal of piezoelectric actuator 14 on line 104. The period P1 shown in FIG. 7A–FIG. 7D resembles the period P shown in FIG. 4A–FIG. 4D, with the digital pulses of signals PWM-A and PWM-B having the pulse width W. In the period $P_1$, the drive signal applied to piezoelectric actuator 14 has the amplitude A, which depends on the pulse width W. But if the user input value VoltInput is changed (e.g., by a change of setting implemented via user input device 108), then the routine CheckVoltsInput obtains a new control voltage to be used for the VoltInput and the routine CheckVolts increments or decrements the PWM value accordingly. For example, if the user input value of VoltInput is increased, then the PWM value is incremented (step 6D-11). FIG. 7A–FIG. 7D show such incrementation of the pulse width affecting the period $P_2$, so that in period $P_2$ the width of the digital pulses of signals PWM-A and PWM-B (shown in FIG. 7A and FIG. 7B, respectively) is increased from W to W'. As a result of the increased pulse width of the pulses of signals PWM-A and PWM-B, the amplitude of the pulse output applied on line drive signal applied on line 104, and the amplitude of the sine wave which results from the integration by piezoelectric actuator 14, is increased from A to A' during period $P_2$. In FIG. 7A–FIG. 7D, the period $P_1$ and $P_2$, although having different subscripts, are of the same duration. The differing subscripts for period P in FIG. 7A–FIG. 7D are merely for highlighting the change of pulse width from W to W' and resulting change of amplitude from A to A'. This change of pulse width, and thus the change of amplitude of the drive signal applied to piezoelectric actuator 14, is one example of dynamically changing the drive signal (e.g., the shape of the drive signal) during real time operation of the pump.

Figure 6F:
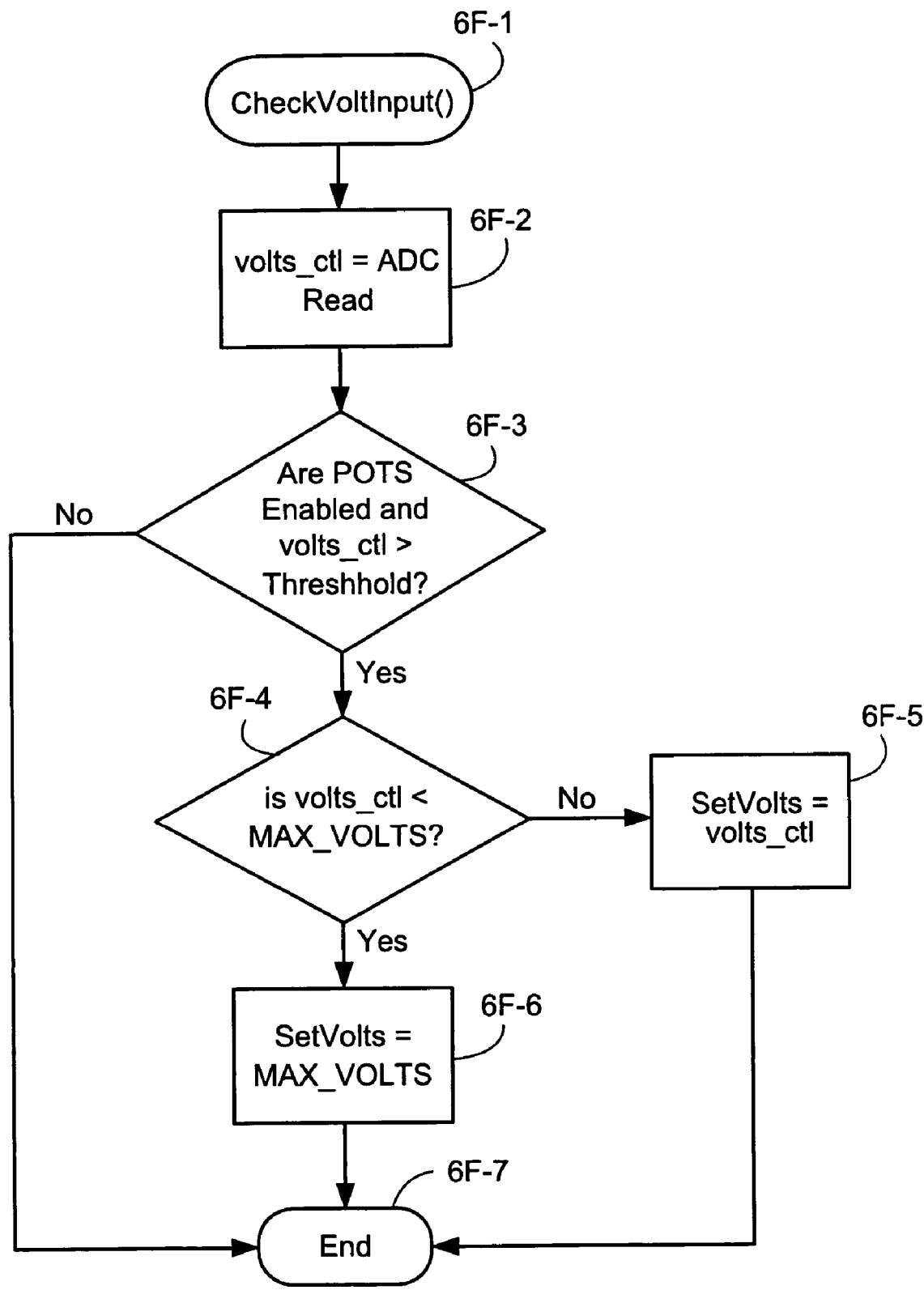

As mentioned above, the routine CheckAtoDs (at step 6C-6) calls the routine CheckVoltsInput to determine whether the user input voltage obtained from user input device 108 indicates that the desired amplitude of the drive signal has been changed by the user. If necessary, the routine CheckVoltsInput makes an adjustment in the desired amplitude. Basic steps of an example implementation of routine CheckVoltsInput are illustrated in FIG. 6F. The routine CheckVoltsInput is entered at step 6F-1. At step 6F-2, the (now digitally converted) voltage just read (at step 6C-4 of routine CheckAtoDs) by the channel handling the user input device 108 is set as the value of a variable volts_ctl. As a precaution, a check is made at step 6F-3 that both (1) the trim pots 106 and 108 have been enabled, and (2) that the value of the variable volts_ctl just acquired exceeds a threshold. Should either condition of step 6F-3 not be satisfied, the routine CheckVoltsInput is exited at step 6F-7.

At step 6F-4 a check is made whether the value of the variable volts_ctl is less than a variable MAX_VOLTS. The value of the variable MAX_VOLTS reflects a maximum permissible amplitude for the drive signal for piezoelectric actuator 14. If value of the variable volts_ctl is less than the variable MAX_VOLTS, at step 6F-5 a value of variable SetVolts is set equal to the variable volts_ctl. Otherwise, at step 6F-6 the variable volts_ctl is set to the value MAX_VOLTS. After the value of variable volts_ctl has been established (either at step 6F-5 or step 6F-6), the routine CheckVoltsInput is exited at step 6F-7.

7.6 Drive Signal Control Program: Check Rate Input Routine

Figure 6G:
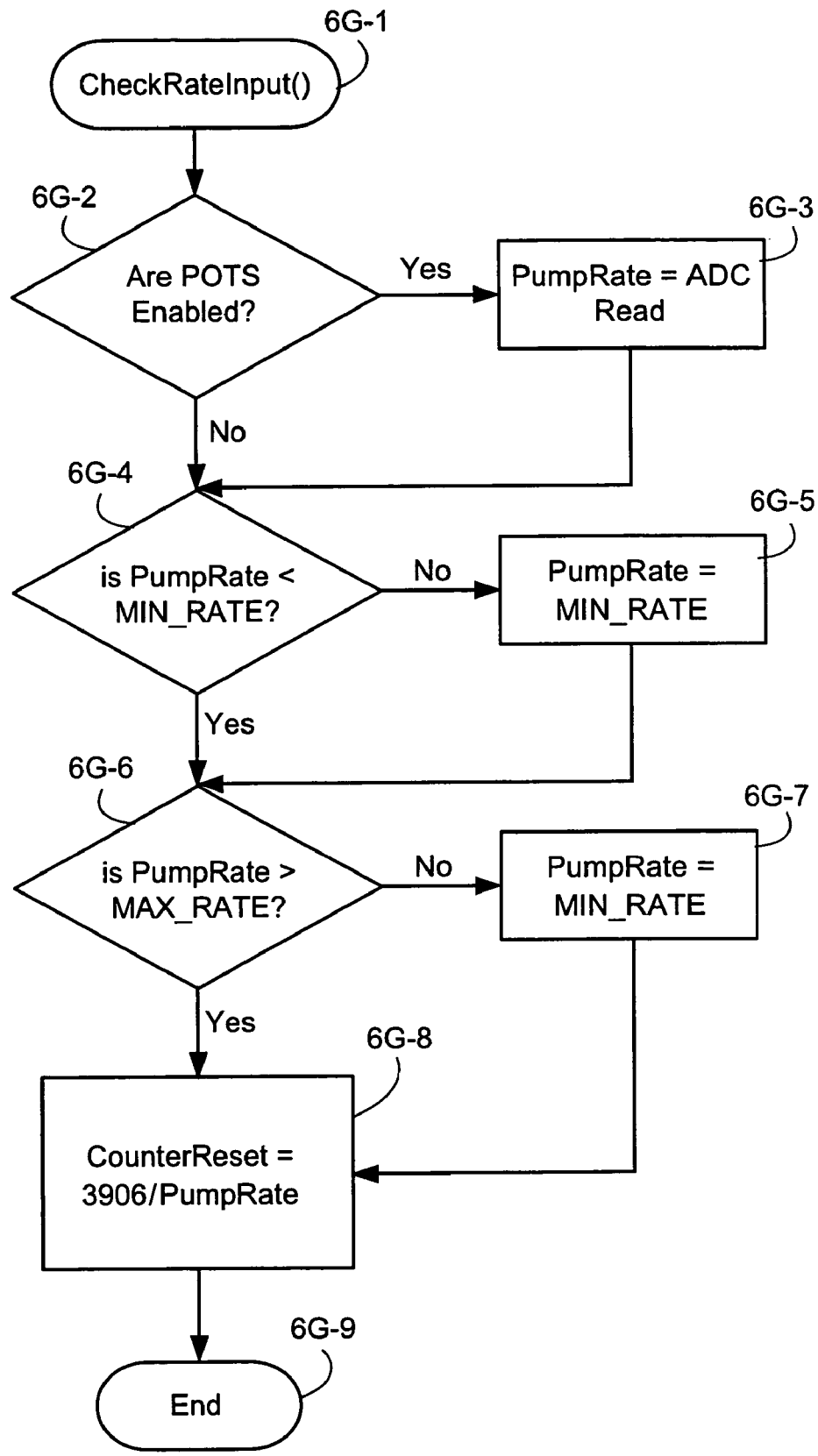
Figure 7A:
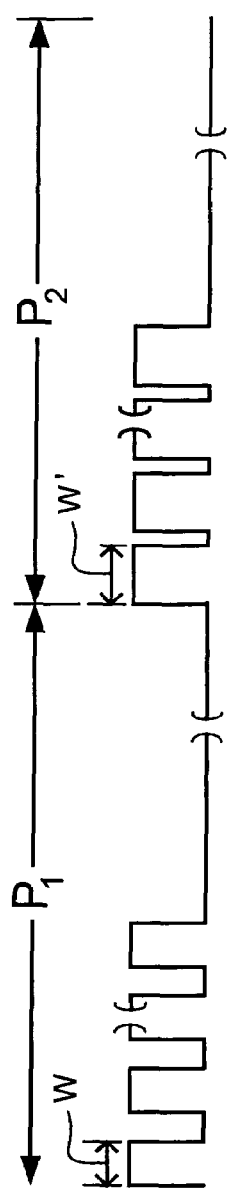
FIG. 7A–FIG. 7D are diagrammatic views of example signals for the purpose of illustrating a change of pulse width modulation and a corresponding change of amplitude of a drive signal for a piezoelectric actuator.
Figure 7B:
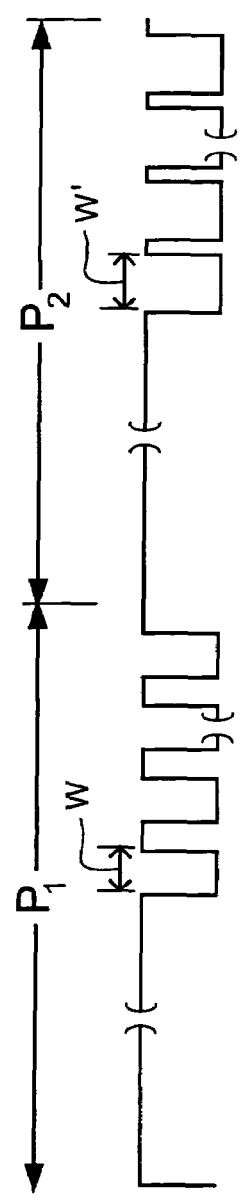
Figure 7C:
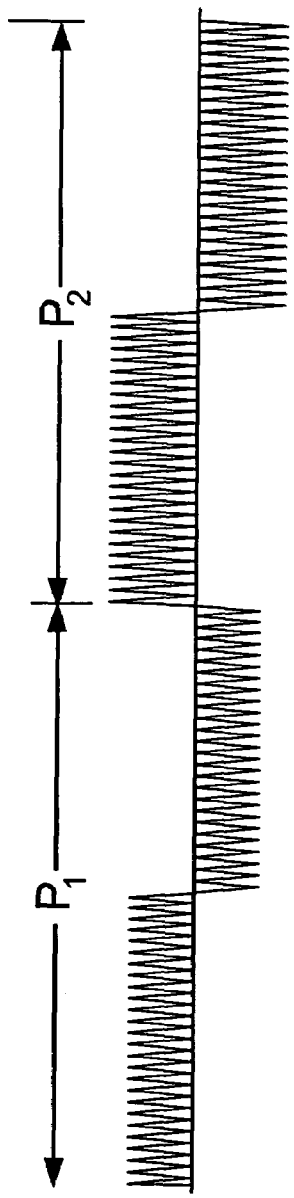
Figure 7D:
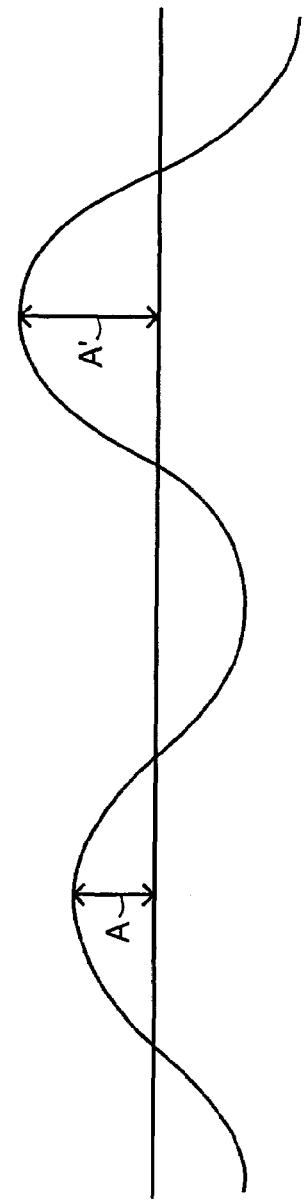
Figure 8A:
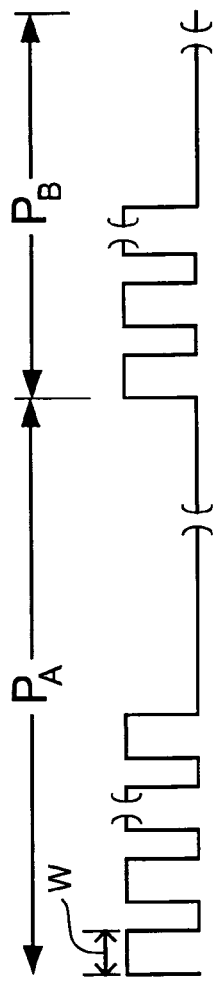
FIG. 8A–FIG. 8D are diagrammatic views of example signals for the purpose of illustrating a change of frequency or period of a drive signal for a piezoelectric actuator.
Figure 8B:
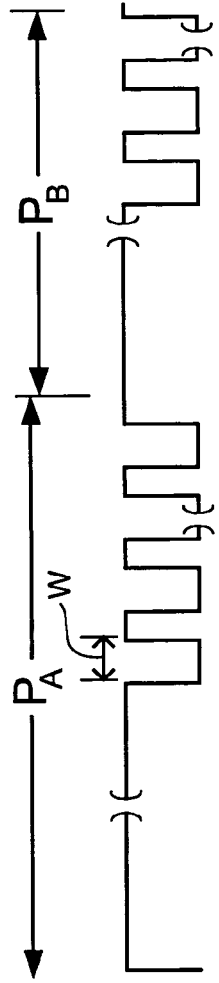
Figure 8C:
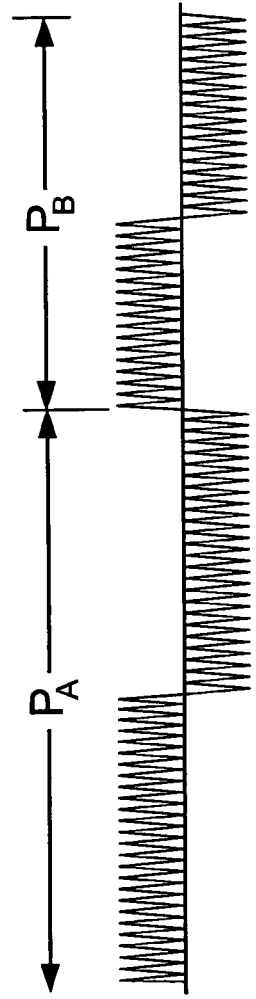
Figure 8D:
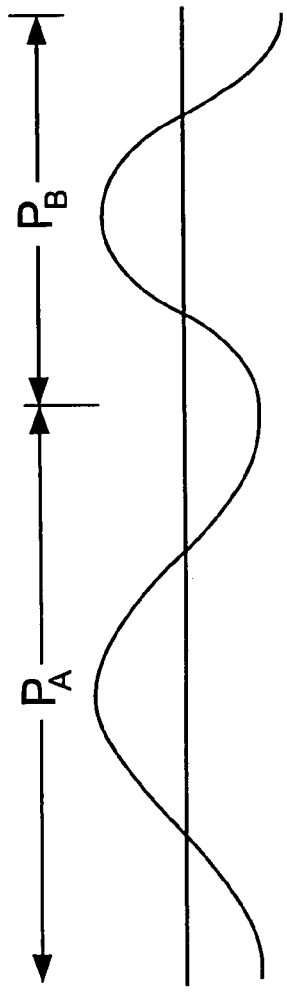

As mentioned above, the routine CheckAtoDs (at step 6C-12) calls the routine CheckRateInput to determine whether the user input voltage obtained from user input device 106 indicates that the desired frequency of the drive signal has been changed by the user. If necessary, the routine CheckRateInput makes an adjustment in the desired frequency. Basic steps of an example implementation of routine CheckRateInput are illustrated in FIG. 6G. The routine CheckRateInput is entered at step 6G-1. As a precaution, a check is made at step 6G-2 that the trim pots 106 and 108 have been enabled. If the check of step 6G-2 is affirmative, at step 6G-3 a value of variable PumpRate is set to the (now digitally converted) voltage just read (at step 6C-10 of routine CheckAtoDs) by the channel handling the user input device 106. Should the check of step 6G-2 prove negative, a check is made at step 6G-4 if the value of the variable PumpRate is less than a value MIN_RATE. If the check at step 6G-4 is affirmative, at step 6G-5 the value of the variable PumpRate is set equal to the value MIN_RATE. On the other hand, at step 6G-6 a check is made whether the value of the variable PumpRate is greater than a value MAX_RATE. If the check at step 6G-6 is affirmative, at step 6G-7 the value of the variable PumpRate is set equal to the value MAX_RATE. Before it exits at step 6G-9, at step 6G-8 the routine CheckRateInput uses the value of the variable PumpRate to determine the variable CounterReset. In particular, at step 6G-8 the routine CheckRateInput divides 3906 (the frequency at which the interrupt service routine of FIG. 6B is called) by the value of the variable PumpRate to determine the variable CounterReset. As explained previously, the value of the variable CounterReset is used to establish the value of the variable Counter. The variable Counter affects the desired setting of the period or frequency for the drive signal to piezoelectric actuator 14 on line 104, as previously explained with reference to the interrupt service routine of FIG. 6B.

FIG. 8A–FIG. 8D illustrate a change of period or frequency of the drive signal applied on line 104. In FIG. 8A–FIG. 8D, $P_A$ refers to a first period which is of comparable duration to period P in FIG. 4A–FIG. 4D. But the period $P_B$ of FIG. 8A–FIG. 8D shows how the period can be changed in accordance with a new user input value for the variable PumpRate (which may be input via user input device 106, for example). Specifically, FIG. 8A–FIG. 8D show the period $P_B$ as being shorter than the period $P_A$ in view of a new (smaller) value for the variable PumpRate. As explained above, the period for the drive signal applied on line 104 is implemented using routine CheckRateInput which has been described above with reference to FIG. 6G. This change of the period or frequency of the drive signal applied to piezoelectric actuator 14 is another example of dynamically changing the drive signal (e.g., the shape of the drive signal) during real time operation of the pump.

The pulse period of the PWM-A and PWM-B waveforms can be adjusted on a pulse by pulse basis in "real-time", producing an endless array of drive waveform possibilities. For such complex waveforms, it may be necessary to employ a digital signal processor type of microcontroller.

8.0 Determining Parameter(s) of Piezoelectric Actuator

One use of one or more embodiments and modes of operation of the piezoelectric actuator drive circuit 18 described above involves determining one or more parameters or characteristics of piezoelectric actuator 14 or of a system in which the piezoelectric actuator 14 operates.

8.1 Determining Capacitance of Piezoelectric Actuator

For accurate operation of pump 10 it is important to have an accurate determination of the capacitance of the piezoelectric actuator 14. As a general rule, a higher capacitance piezoelectric element has more energy and displaces further than a lower capacitance piezoelectric element. While the particular piezoelectric material employed in piezoelectric actuator 14 may have a specified or nominal capacitance, experience shows that the capacitance of piezoelectric elements produced in a same manufacturing lot may vary as much as five percent from piece to piece, and that the capacitance of the same type of piezoelectric elements produced in different lots may vary by as much as twenty five percent.

Embodiments of the piezoelectric actuator drive circuit 18 herein described enable a pump manufacturer to use a piezoelectric element which differs from the nominal capacitance for its type. Advantageously, these embodiments of piezoelectric actuator drive circuit 18 can automatically determine the actual capacitance and thereby deliver the appropriate voltage in view of the actual capacitance. In other words, the piezoelectric actuator drive circuit 18 senses the capacitance of piezoelectric actuator 14, and customizes the drive signal accordingly. For example, for a piezoelectric actuator 14 whose ceramic degrades over time, the piezoelectric actuator drive circuit 18 can test the load (e.g., piezoelectric actuator 14) and thereafter drive the piezoelectric actuator 14 with a higher voltage to compensate for degradation or variation of the piezoelectric element over time.

Figures 9A, 9B:
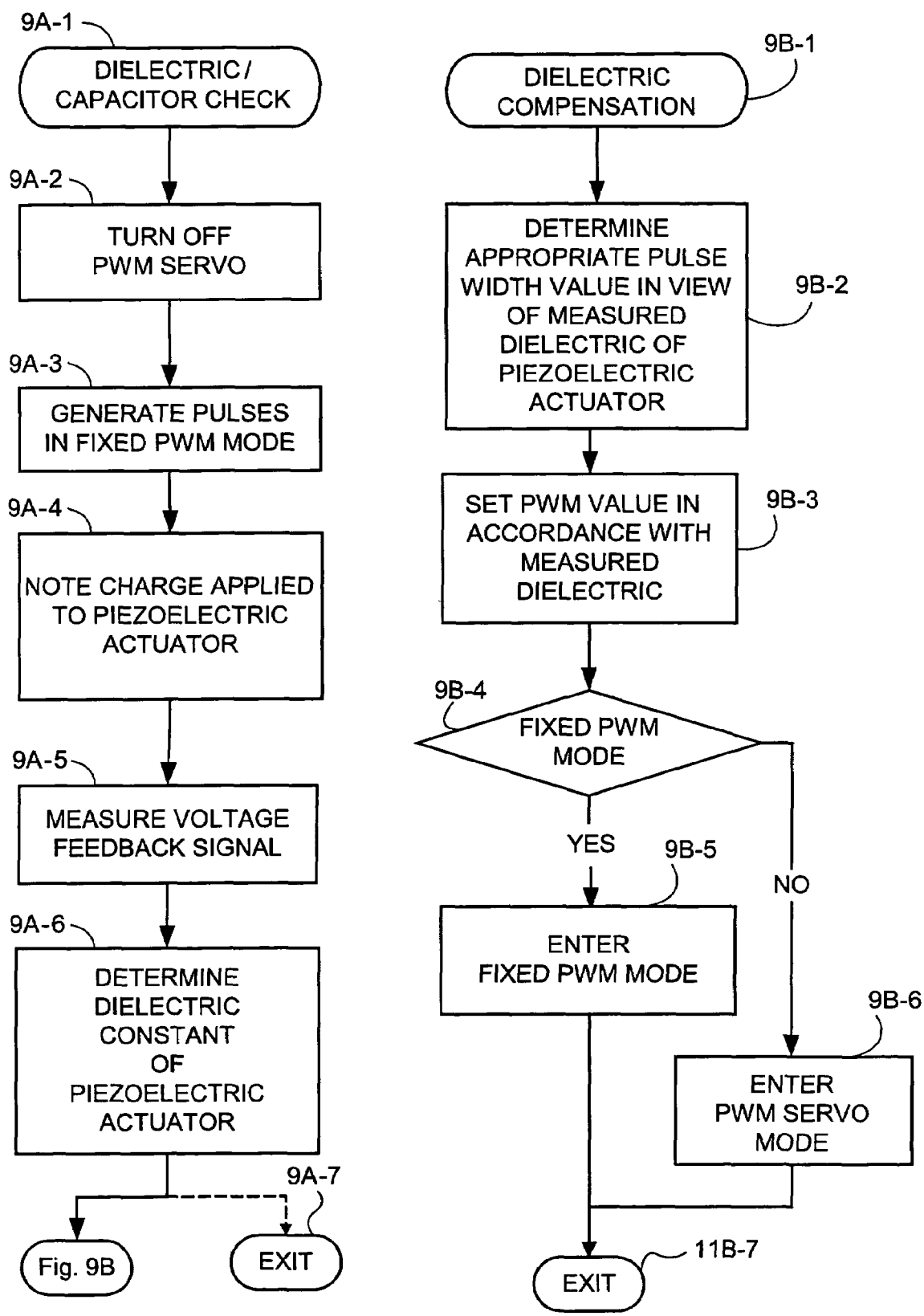
FIG. 9A is a flowchart showing basic example steps included in a capacitance check routine.
FIG. 9B is a flowchart showing basic example steps included in a capacitance compensation routine.

FIG. 9A illustrates some selected, representative, basic steps involved in a capacitance check routine which determines the capacitance of the piezoelectric actuator 14 for an example mode of operation. The capacitance check routine of FIG. 9A is executed by microcontroller 116 and is entered at step 9A-1. At step 9A-2, the capacitance check routine turns off the PWM servoing capability of piezoelectric actuator drive circuit 18. In other words, capacitance check routine disables the call to routine CheckVolts (which is illustrated in FIG. 6D), and goes into a fixed PWM mode for controlling the drive signal applied to piezoelectric actuator 14. In the fixed PWM mode, as step 9A-3 digital pulses are generated by pulse generator 100 with the pulse widths of the signal PWM-A and PWM-B applied on lines 124 and 126, respectively, being consistent and the amount of charge being applied in pulses to piezoelectric actuator 14 being known (e.g., an ascertainable electrical charge amount which can be pre-stored in a memory, for example). As step 9A-4, the user input device 106 notes the charge being applied to piezoelectric actuator 14.

Having applied a known amount of charge (in Coulombs) to the piezoelectric actuator and by subsequently measuring the voltage (in volts) on the piezoelectric actuator (at step 9A-5), the capacitance can be directly calculated. The voltage measurement is obtained by the voltage feedback signal applied by output monitor 122 on line 105 to microcontroller 106. The capacitance check routine samples the voltage feedback signal applied by output monitor 122 on line 105 to microcontroller 106.

Alternatively, the capacitance check routine samples the voltage feedback signal obtained from output monitor 122 at successive points along a waveform, and particularly at and after the peak of the waveform. For example, the capacitance check routine determines the voltage measurements at several points in a time neighborhood around peak K of a waveform such as the waveform of FIG. 10A. A line $S_{10A}$ shows a slope of the voltage measurements for the waveform of FIG. 10A after the peak K. One way of determining the capacitance constant is to use the slope. As a further alternate, the PWM mode can be exited, and two precisely timed voltage readings be taken. then, knowing the resistive leakage of the circuit (either empirically or at time of manufacture and store in a memory such as an EEPROM), the capacitance can be calculated using a simple RC time constant calculation.

After determining the capacitance of piezoelectric actuator 14, the capacitance check routine can exit (as depicted by step 9A-7). More preferably, however, the capacitance check routine can call or be succeeded by a capacitance compensation routine. FIG. 9B illustrates selected basic steps involved in the capacitance compensation routine, which is executed by microcontroller 116 and is entered at step 9B-1.

At step 9B-2, the capacitance compensation routine determines an appropriate pulse width value for the PWM signal (e.g., the signal PWM-A on line 124 and the signal PWM-B on line 126 in the FIG. 5A circuit, or the PWM signal in the FIG. 5C circuit) in view of the capacitance of piezoelectric actuator 14. In other words, the capacitance compensation routine now uses the sensed parameter of the piezoelectric actuator to control the drive signal to the piezoelectric actuator. The capacitance of piezoelectric actuator 14 may have been determined by a previous execution of capacitance check routine (see FIG. 9A). The pulse width value may be determined in any of several ways. For example, the pulse width value determination of step 9B-2 may involve checking a lookup table or the like which has a paired correspondence between stored feedback voltage values (indicative of the measured capacitance value of piezoelectric actuator 14) and stored pulse width values (which result in a corresponding charge for piezoelectric actuator 14). As another example, the capacitance compensation routine may make a calculation for pulse width. As a basic example, the capacitance previously determined can be used in a suitable equation to determine the PWM width setting that will give the desired actuator voltage. Alternatively, a lookup table operation may also be used to determine the pulse width.

After determining the necessary pulse width for the PWM signal (e.g., PWM-A on line 124 and the signal PWM-B on line 126) in view of the capacitance, as step 9B-3 the capacitance compensation routine sets the value PWM to the appropriate capacitance-determined pulse width value determined at step 9B-2. Then, as step 9B-4, the capacitance compensation routine checks whether it should initiate a fixed PWM mode of operation or a PWM servo mode of operation.

If the fixed PWM mode of operation is selected at step 9B-4, then as step 9B-5 the capacitance compensation routine enters or enables the fixed PWM mode. Entering or enabling the fixed PWM mode essentially means that a consistent PWM value (the value determined at step 9B-2 and set at step 9B-3) is consistently utilized for forming the pulse widths of the signal PWM-A and PWM-B. In other words, in the fixed PWM mode the routine CheckVolts is bypassed so that the PWM value is not updated by a feedback signal or other signal.

If the PWM servo mode of operation is selected at step 9B-4, then as step 9B-6 the capacitance compensation routine enters or enables the PWM servo mode. Entering or enabling the PWM servo mode essentially means that a the PWM value can be updated or changed in accordance with input, such as the feedback voltage signal applied on line 105 by output monitor 122. In so doing, the capacitance compensation routine may first need to turn off the fixed PWM mode (if the fixed PWM mode had been turned on, such as at step 9A-2, for example). Turning on the PWM servo functionality involves including the routine Check-Volts as part of execution of microcontroller 116, so that the PWM value is update (e.g., decremented at step 6D-9 or incremented at step 6D-11) in accordance with an input value (e.g., an ADC read value obtained at step 6D-2).

FIG. 10A has been mentioned above as illustrating a waveform of voltage measurements (obtained, e.g., at step 9A-5 of capacitance check routine) for determining the capacitance of a first example piezoelectric actuator. FIG. 10B illustrates another waveform of voltage measurements obtained for determining the capacitance of a second example piezoelectric actuator. The second piezoelectric actuator of FIG. 10B happens to have less capacitance than the first piezoelectric actuator of FIG. 10A, which is illustrated by the fact that the slope of the waveform of FIG. 10B is greater (in a negative direction) than the slope of the waveform of FIG. 10A.

8.2 Determining Impedance/Resonance of Piezoelectric System

The piezoelectric actuator drive circuit 18 facilitates determinations of the impedance of a system in which the piezoelectric actuator 14 operates, the impedance being an indication of the resonant frequency of piezoelectric actuator 14. For example, when the piezoelectric actuator 14 operates in a pump, the impedance of the system comprising the piezo pump, the attached tubing, the fluid viscosity, the trapped air, etc. The impedance of the system relates to the resonant frequency of the system. A low impedance point in a frequency spectrum indicates a resonant frequency. If the resonant frequency of the system is known, the performance of the pump can be optimized for that particular system. Typically, the resonant frequency of a system is anywhere from 40 to 130 Hertz. One pump in two different systems will have two different resonant frequencies and therefore it is desirable to be able to measure the system resonant frequency in real time. Once the resonant frequency is known, the micro controller can adjust the drive frequency for maximum performance.

Two example and non-limiting impedance/resonance determination techniques are an impedance measurement technique and an impulse response technique. Both the impedance measurement technique and the impulse response technique are preferably implemented during real time operation of pump 10, e.g., while piezoelectric actuator 14 is actually pumping fluid in pump 10.

8.2.1 Impedance Measurement Technique

The first technique is very similar to the previously described capacitance technique. A constant power drive is applied at various drive frequencies and the signal attenuation is measured. The frequency at which maximum attenuation occurs indicates minimum impedance and thus indicates the resonant frequency.

Figure 11A:
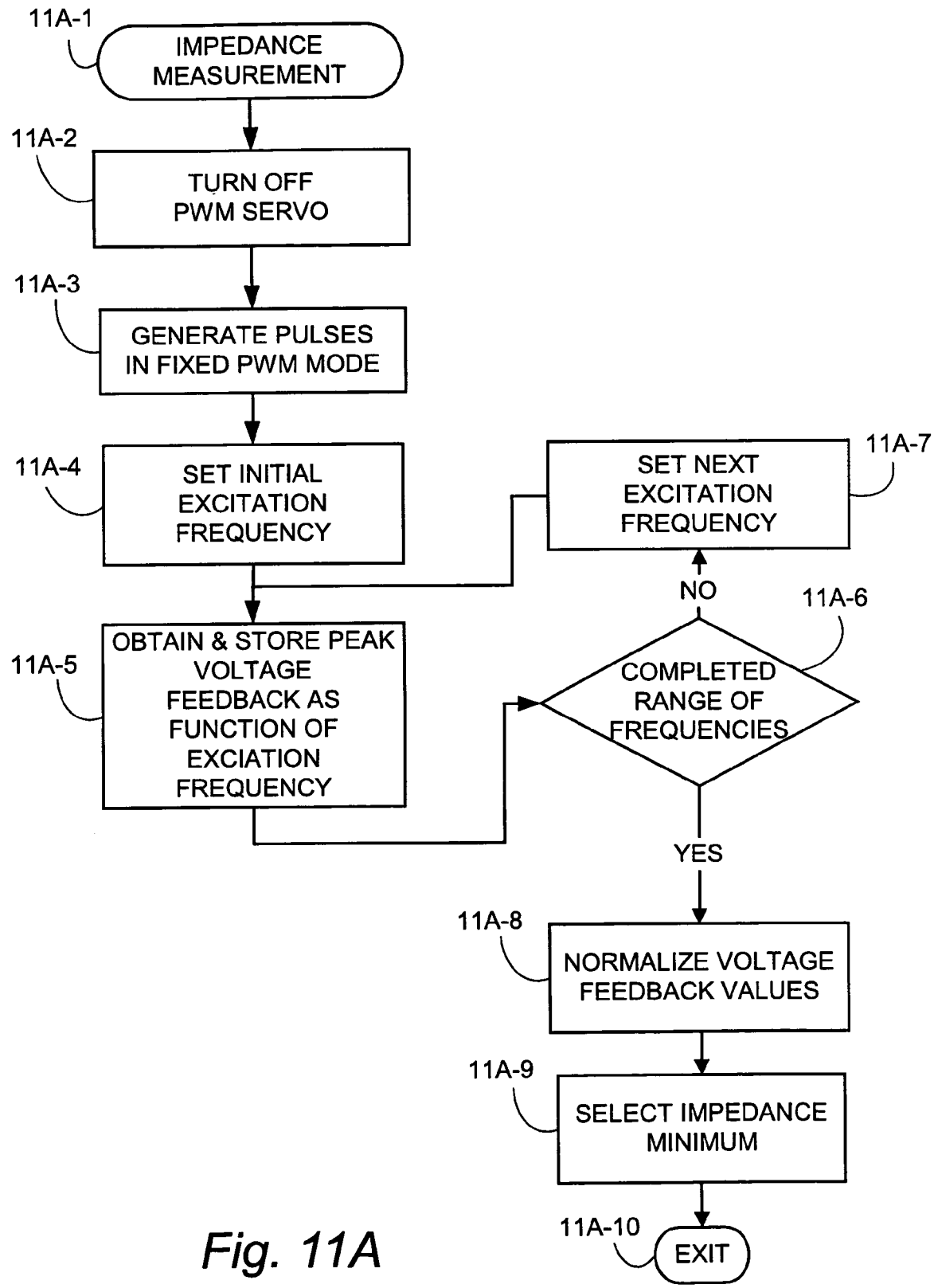
FIG. 11A is a flowchart showing basic example steps included in an impedance measurement routine.

Basic example steps of the impedance measurement technique are illustrated in FIG. 11A. In the impedance measurement technique, the resonant frequency of pump 10 is indirectly found by making a series of crude impedance measurements for the piezoelectric actuator 14 at many different frequencies and finding a minimum frequency. A routine for implementing the impedance measurement technique can be executed by microcontroller 116, and is entered at step 11A-1.

As step 11A-2, the impedance measurement routine turns off the PWM servoing capability of piezoelectric actuator drive circuit 18. This is because the impedance of piezoelectric actuator 14 at a particular frequency is made by driving piezoelectric actuator 14 with the voltage control servo circuitry disabled. This is accomplished by the impedance measurement routine disabling the call to or otherwise bypassing the routine CheckVolts (which is illustrated in FIG. 6D), and going into a fixed PWM mode as indicated by step 11A-3. In the fixed PWM mode, the microcontroller 116 generates signals PWM-A and PWM-B with a fixed pulse width modulation so that the piezoelectric actuator 14 is driven with a constant power input which will translate to an achieved peak voltage on piezoelectric actuator 14 that is proportional to its impedance.

In its remaining steps, the impedance measurement routine of FIG. 11A sweeps through a series of excitation frequencies, takes a voltage feedback measurement for each frequency, normalizes the voltage feedback signals, and then determines an impedance minimum. At step 11A-4 the impedance measurement routine sets the initial excitation frequency. With the excitation frequency having been set, at step 11A-5 the impedance measurement routine obtains (from output monitor 122 on line 105) a peak voltage feedback signal from piezoelectric actuator 14. The voltage feedback signal obtained at step 11A-5 is stored in association with the excitation frequency with which it was generated. At step 11A-6 the impedance measurement routine determines whether it has completed the entire range of excitation frequencies through which it is to sweep. If not, at step 11A-7 a next excitation frequency of the range is chosen, and thereafter at step 11A-5 the peak voltage feedback for the next excitation frequency is obtained and stored. Thus, the impedance measurement routine has varied the drive signal through a range of excitation frequencies, and has obtained a voltage value from the feedback signal for each of the excitation frequencies.

After it has been determined at step 11A-6 that the entire range of excitation frequencies has been checked, at step 11A-8 the peak voltage feedback signal values obtained for the entire range are normalized. Then, as step 11A-9, the impedance measurement routine determines the resonant frequency of pump 10 as the particular excitation frequency in the scan range that resulted in the minimum impedance value (i.e., the minimum voltage feedback peak value).

8.2.2 Impulse Response Technique

The second technique measures the resonant frequency not by measuring the dynamic impedance but by measuring the system's impulse response. This is exactly equivalent to hitting a tuning fork with a hammer and measuring the fork frequency. The piezo is hit with an electrical impulse and then "listened to" via the voltage feedback line for the physical shock wave to propagate into the pump system, and then "bounce" back to the piezo and physically displace it, generating an echoed electrical impulse. The inverse of the time between the impulse excitation and the echo is the resonant frequency of the system.

Figure 11B:
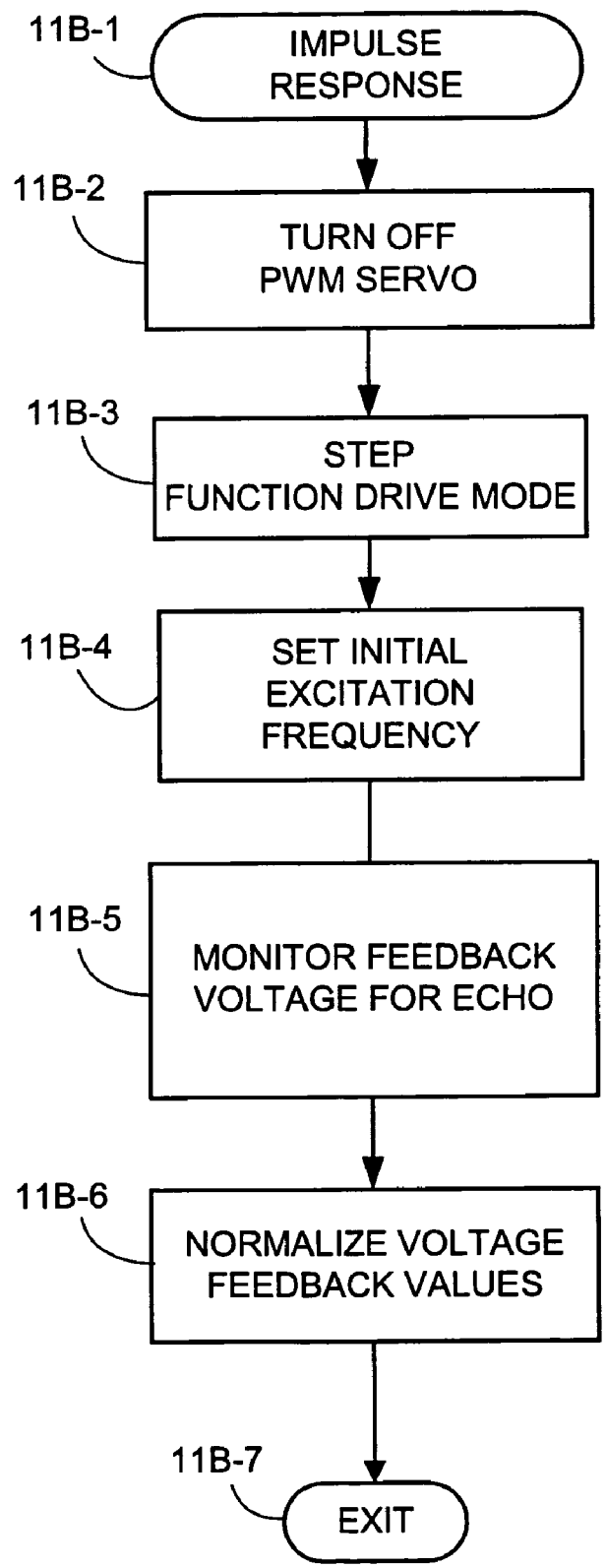
FIG. 11B is a flowchart showing basic example steps included in an impedance impulse response routine.

Basic example steps of the impulse response technique are illustrated in FIG. 11B. A routine for implementing the impulse response technique can be executed by microcontroller 116, and is entered at step 11B-1. As understood in view of previous discussions, at step 11B-2 the impulse response routine turns off the PWM servoing capability of piezoelectric actuator drive circuit 18. Then, in the remaining steps of the impulse response routine, the resonant frequency of pump 10 is directly measured by "pinging" the piezoelectric diaphragm (e.g., piezoelectric actuator 14) with a step function drive signal, and then continuously monitoring the voltage across the piezoelectric actuator 14 to look for the "echo". The inverse of the echo period is the resonant frequency.

As step 11B-4, the microcontroller 116 enters a step function drive mode in which the pulse widths of the signals PWM-A and PWM-B are set in accordance with a step function. That is, the pulse widths of the signals PWM-A and PWM-B are initially set at a first value, then increased to a second (greater) value, then increased to a third (yet greater) value, and so forth. In other words, the impulse response routine varies the drive signal, and all the while, as step 11B-5, the voltage feedback signal from output monitor 122 on line voltage feedback signal on line 105 is monitored by microcontroller 116 or some other processor. When the echo is found, at step 11B-6 the inverse of the echo period is taken as the resonant frequency of the piezoelectric actuator 14.

9.0 Drive Circuit Receiving Sensor Signals

Figure 19:
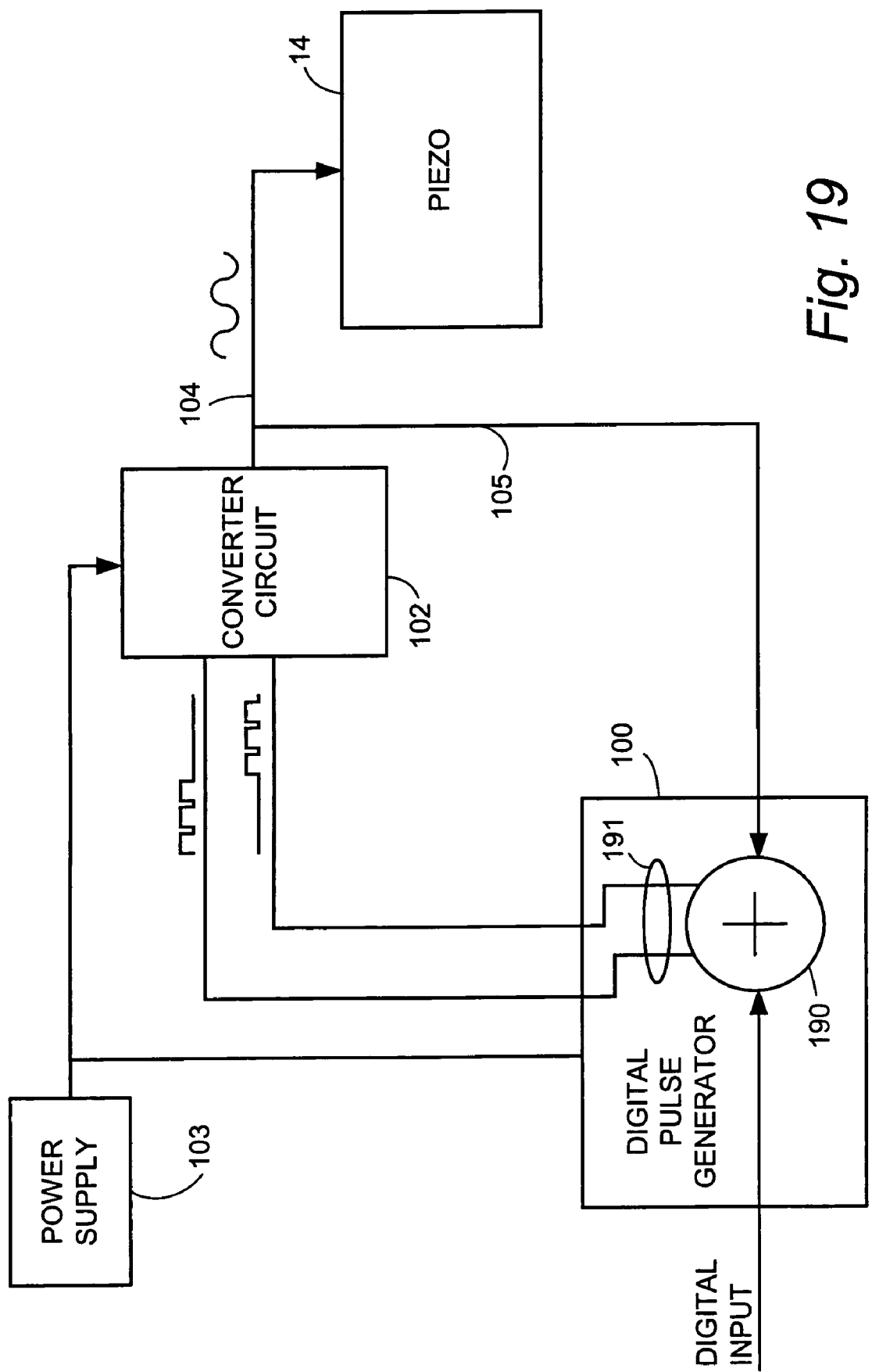
FIG. 19 is a schematic view showing receipt and handling of a digital input signal by an example piezoelectric actuator drive circuit.

As mentioned above, the connector 110 can be connected to one or more sensors. Such sensor(s) supply a corresponding sensor signal(s) to piezoelectric actuator drive circuit 18, and to microcontroller 116 in particular. For example, FIG. 19 shows a digital input signal, e.g., from a sensor, which is applied to actuator drive circuit 18. The pulse generator (e.g., microcontroller 116) receives the digital input and has a signal logic combination function 190 which combines the digital input signal with the feedback signal on line 105 to produce a combined output 191. Prior to being input to signal logic combination function, the feedback signal on line 105 can be converted from analog to digital. The person skilled in the art understands the workings of signal logic combination function 190 in view of widely understood control theory, since the signal logic combination function 190 essentially uses the digital input signal to modify the output that pulse generator 100.

The digital input signal shown in FIG. 19 can be from a graphical user interface or the like as shown in FIG. 3C, or from an in-pump sensor as shown in FIG. 3D, or from sensors elsewhere located such as (for example) as shown in FIG. 3E, FIG. 3F, and FIG. 3G. For example, if the pump were used for cooling and the digital input signal to the pulse generator 100 were to indicate that a sensed temperature is rising, using control theory the signal logic combination function 190 would increase pump operation. Conversely, if the temperature were to drop as indicated by the digital input signal, the pulse generator would decrease pump operation.

10.0 Drive Signal Waveform Optimization

As previously indicated, in a waveform optimization mode the piezoelectric actuator drive circuit 18 can use previously prepared and/or pre-stored information (e.g., waveform shape data) in order to generate a drive signal with optimized waveform for application to the piezoelectric actuator 14 of a pump. The previously prepared and prestored information can be stored in a table, such as lookup table 140 (see FIG. 5B). The information can be prepared so that the waveform is optimized with respect to one or more criteria (e.g., one or more operational parameters/variables). The waveform shape data is optimized in the waveform optimization mode for purposes including those of making the piezoelectric actuator use the power with which it is supplied more efficiently, and for less noise, and hopefully with minimum (if any) charge recovery measures.

10.1 Waveform Optimization Apparatus

Figure 13:
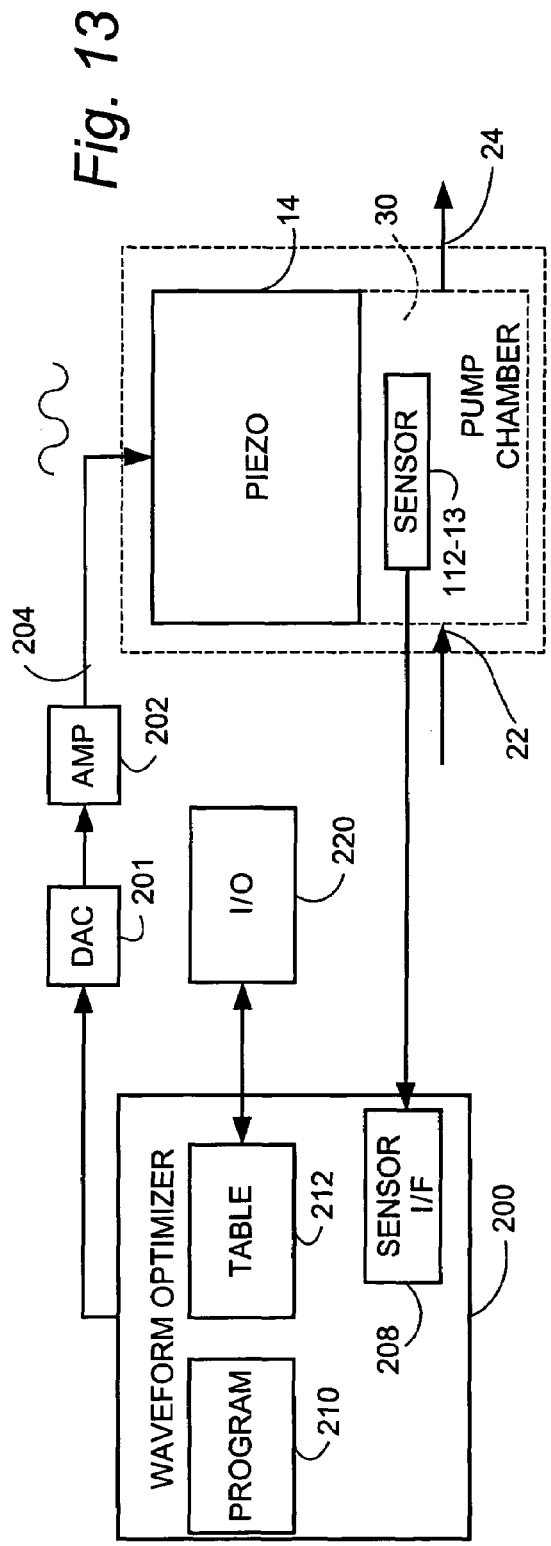
FIG. 13 is a schematic view showing use of a waveform optimizer to generate a table of waveform optimization values for a driving signal for a piezoelectric pump.

FIG. 13 shows an example embodiment waveform optimizer 200 which generates a table of waveform optimization values. The waveform optimization values developed by waveform optimizer 200 are intended for use as waveform shape data by a target drive circuit for generating a driving signal for a target piezoelectric pump. To develop these waveform optimization values, the waveform optimizer 200 generates a drive signal which is applied to a digital to analog converter (DAC) 201, after which the analog drive signal is amplified (by amplifier 202) and applied on line 204 to a piezoelectric actuator. The piezoelectric actuator is situated in an operating pump. Although the same reference numerals have been employed in FIG. 13 as in previous figures to refer to piezoelectric actuator 14 and elements of pump 10, it should be understood that the waveform optimization data being prepared by waveform optimizer 200 is for a target pump and target piezoelectric actuator, which target pump and target actuator can be but are not necessarily the same pump/piezoelectric actuator being driven during the generation of the waveform optimization data. In this regard, the waveform optimization data being prepared by waveform optimizer 200 may be for another (but preferably similar type) piezoelectric actuator or for another (but preferably similar type) pump than the one utilized during the generation of the waveform optimization data.

Figure 16:
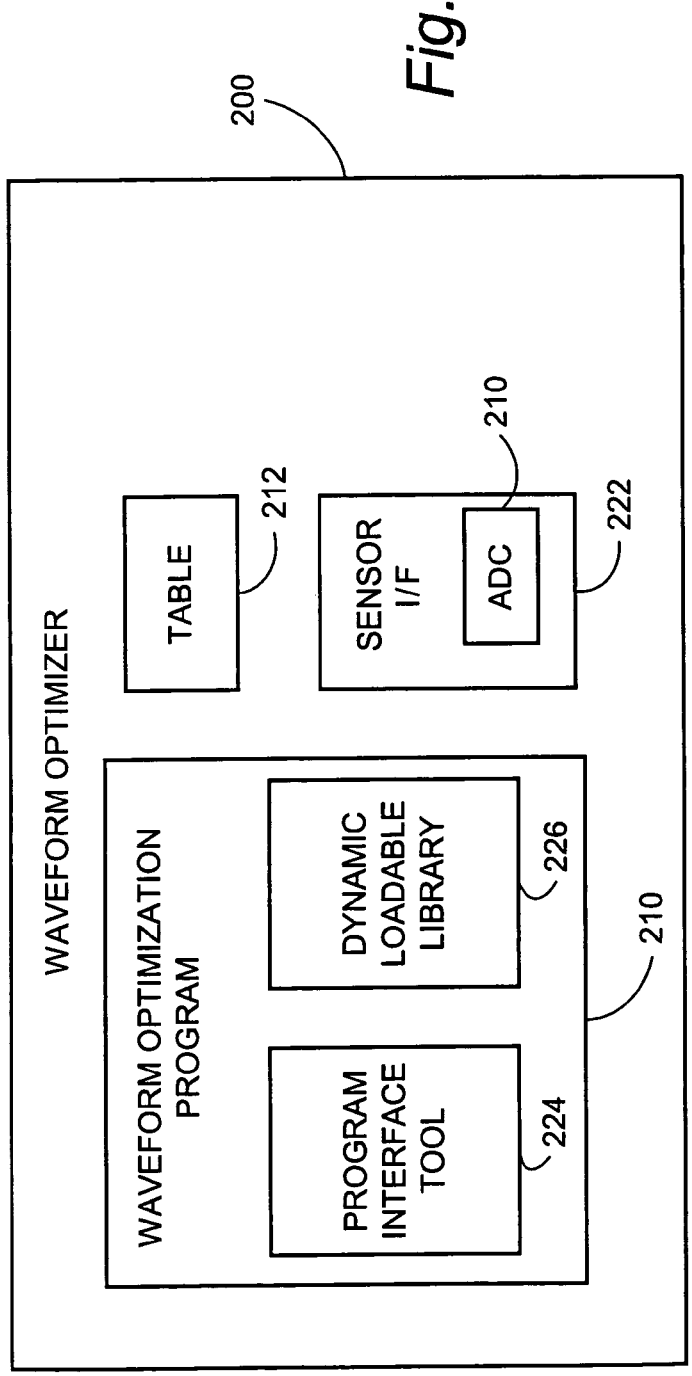
FIG. 16 is a diagrammatic view of an example waveform optimizer.

As indicated previously, the waveform data being prepared by waveform optimizer 200 can be optimized with respect to one or more operational parameters, e.g., one or more criteria. Examples of optimizable criteria include flow (e.g., rate of flow of fluid through the pump), acceleration, noiselessness, pressure, temperature, elevation, power consumption, and signals or input from any other analog or digital feedback device. Optimization of a driving signal waveform typically involves the use of a sensor in order to obtain a signal (e.g., feedback signal) regarding the operational parameter being optimized. More than one such sensor may be utilized, and the location and/or positioning of such sensor(s) depends upon the parameter being sensed/optimized. For sake of simplicity, FIG. 13 generically shows a single sensor 112-13. Depending on the type and nature of sensor(s) employed, the waveform optimizer 200 may include a sensor interface 208 which renders the sensor signal usable by waveform optimizer 200. For example, the sensor interface 208 may include an analog to digital converter (ADC) 222 (see FIG. 16).

In the ensuing discussion an example, non-limiting waveform optimization scenario is described in which the optimized parameter is fluid flow through the pump. In such example scenario it should be understood that the sensor can be a flowmeter, and that the flowmeter may be positioned either at an outlet or downstream from an outlet of the pump.

The waveform optimizer 200 outputs a drive signal on line 204. It will be appreciated that in one example embodiment the waveform optimizer 200 has constituency and operation similar to that of the previously described pulse generators and/or microcontrollers for generating a digital output signal for use as the drive signal. In addition, the waveform optimizer 200 typically includes an executable program, such as waveform optimization program 210. The waveform optimization program 210 executes steps based on instructions stored in a memory in order to generate the drive signal to be applied to the piezoelectric actuator and in order to generate a waveform equation which is solved in order to obtain a table of waveform optimization data values. The waveform optimization data values are stored in a table memory of waveform optimizer 200, illustrated as table 212 in FIG. 13.

An input/output device 220 is connected to waveform optimizer 200 so that the waveform optimization data stored in table 212 can be extracted therefrom. The input/output device 220 can take various forms, such as a display (for reading data values from table 212), or a hardware memory production device (such as a ROM burner for storing values in a read only memory (ROM)).

10.2 Waveform Optimization Convenance Techniques

Figure 14:
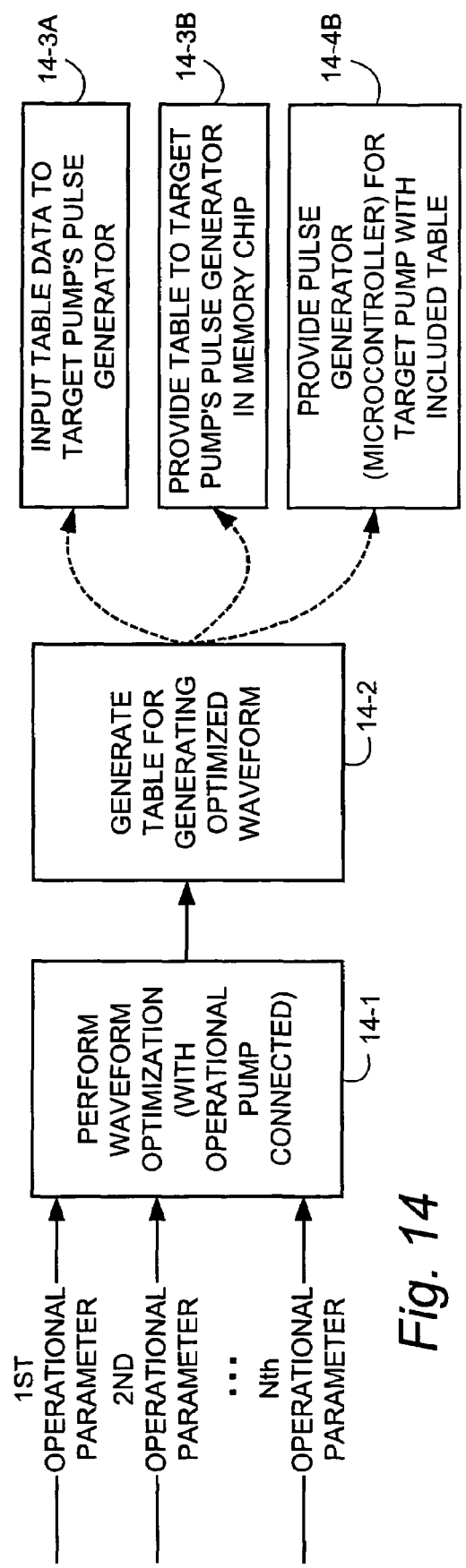
FIG. 14 is a diagrammatic view of general aspects of a procedure for enabling a pulse generator of a piezoelectric pump to produce an optimized waveform.

FIG. 14 shows general aspects or events of a procedure for enabling a pulse generator of a piezoelectric pump to produce an optimized waveform. As event 14-1, the waveform optimizer 200 performs a waveform optimization procedure (e.g., by executing waveform optimization program 210) while connected (in the example manner illustrated in FIG. 13) to apply a drive signal to a piezoelectric actuator which is operating in a functional pump. As indicated above, the particular actuator or pump involved in the connection may or may not be the same as the target actuator/pump with which the waveform optimization data will be utilized. As shown in FIG. 14, in performing event 14-1 the waveform optimizer 200 may receive feedback or at least boundary conditions with respect to one or more operational parameters ("criteria") which influence the waveform optimization. The example sensor 112-13 described above is an example of application of a signal for one type of operational parameter. While in some embodiments the waveform optimization may be performed for only one operational parameter, the FIG. 14 allows for inputs for any number ("N") of operational parameters.

The output of waveform optimizer 200 is a table or listing of waveform optimization data, also known as waveform shape data. Generation of the waveform optimization data for such table is depicted as event 14-2 of FIG. 14. Examples formats of such a table are illustrated in subsequently described FIG. 18A and FIG. 18B.

The waveform optimization data generated by waveform optimizer 200 will subsequently be used in a target piezoelectric actuator drive circuit 18 (such as embodiments described herein) in order to optimize the waveform applied on line drive signal applied on line 104 to piezoelectric actuator 14 in a target pump. Conveyance of the waveform optimization data generated by waveform optimizer 200 to the target pump can occur in several modes, such as the modes respectively illustrated by events 14-3A, 14-3B, and 14-3C in FIG. 14.

As waveform optimization data conveyance mode 14-3A, the particular waveform optimization data generated by waveform optimizer 200 can be input to a memory table comprising or accessible to pulse generator 100 of the target pump in which it is to be utilized. For example, a graphical user interface (GUI) or the like can be utilized for inputting the waveform optimization data developed by waveform optimizer 200 into a memory for piezoelectric actuator drive circuit 18. The memory can be either on-board memory (e.g., for microcontroller 116) or other form of memory (e.g., read only memory (ROM)).

Figures 15A, 15B:
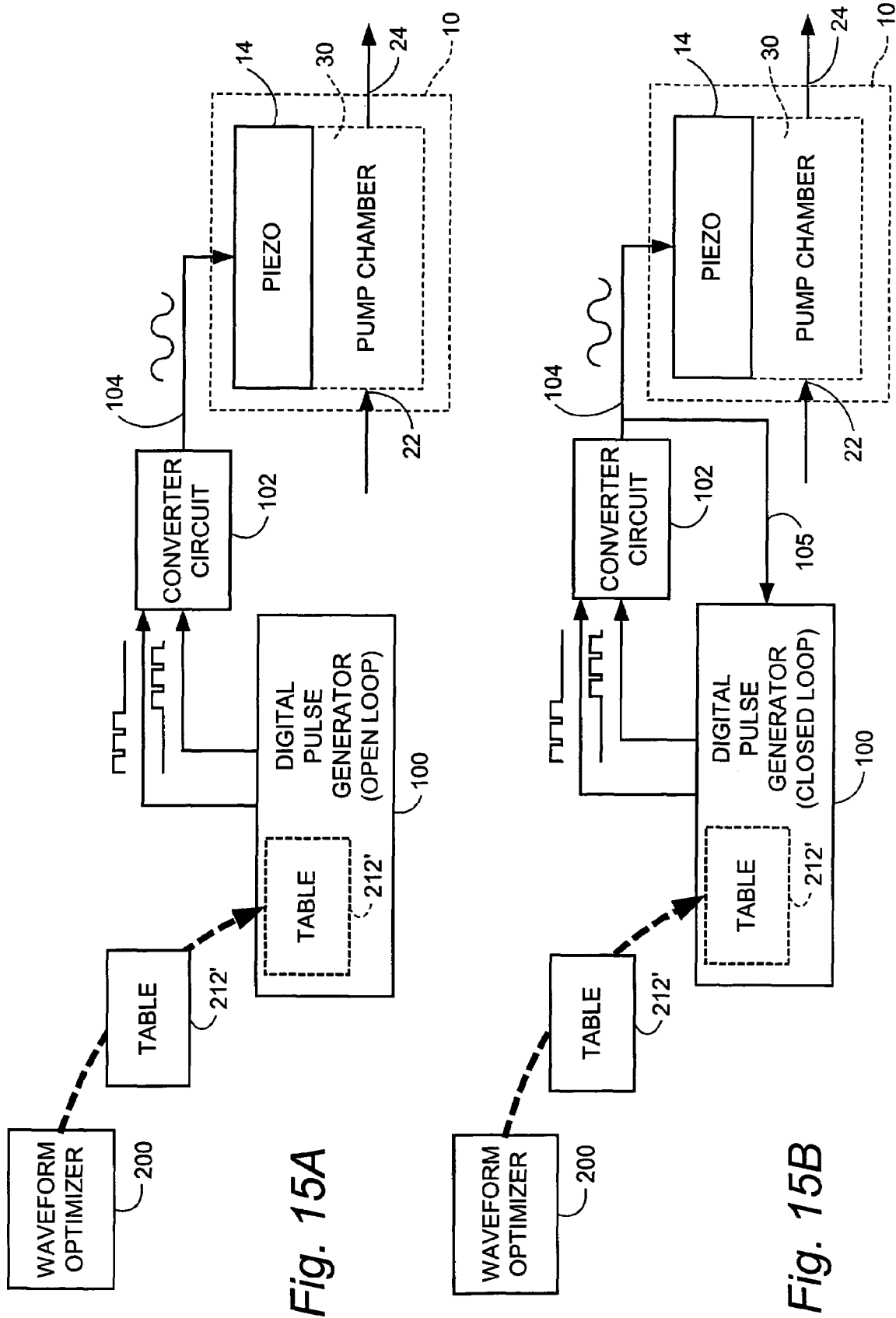
FIG. 15A is a diagrammatic view of a drive circuit for a piezoelectr0069c pump which generates an optimized waveform using an open loop control technique.
FIG. 15B is a diagrammatic view of a drive circuit for a piezoelectric pump which generates an optimized waveform using a closed loop control technique.

As waveform optimization data conveyance mode 14-3B, the particular waveform optimization data generated by waveform optimizer 200 can be stored in table form in a memory chip or other memory device, and afterwards the memory chip/device bearing the waveform optimization data can be installed in the piezoelectric actuator drive circuit 18 of the target pump. This mode is also illustrated in FIG. 15A and FIG. 15B, which shows a version of the waveform optimization data in the form of memory table 212 essentially being incorporated into pulse generator 100 of target pumps.

As waveform optimization data conveyance mode 14-3C, the particular waveform optimization data generated by waveform optimizer 200 can be stored in table form or otherwise in a microprocessor or nicrocontroller of the target pump. For example, in the conveyance mode 14-3C the entire microcontroller 116, and perhaps the entire piezoelectric actuator drive circuit 18, is supplied for the target pump.

10.3 Waveform Optimization Data Preparation Procedure

The logic of the waveform optimization program 210 executed by waveform optimizer 200 can be sequenced, arranged, formatted, and programmed in a variety of ways. Moreover, the waveform optimizer 200 may include one or more controllers, processors, or ASICs which, either in distributed or consolidated manner, perform basic operations such as the example steps hereinafter depicted. In one non-limiting, example configuration illustrated in FIG. 16, the waveform optimization program 210 includes a program interface tool 224 which works in conjunction with a dynamic loadable library 226. An example of a suitable program interface tool is National Instruments LabVIEW™. The dynamic loadable library 226 is a module that is created by a complier, and may be code that is written in a programming language such as C, for example. Other types of program interface tools or programming approaches may alternatively be employed.

FIG. 17A–FIG. 17D are flowcharts which depict basic example steps performed in a non-limiting, example waveform optimization procedure performed by waveform optimizer 200. Step 17-1 reflects commencement of the waveform optimization procedure.

Essentially, the waveform optimization procedure first determines coefficients for a wave equation. The coefficients of the waveform equation are determined to optimize at least one operational parameter of the pump. Then the waveform optimization procedure solves the waveform equation to obtain waveform shape data which can be utilized by the piezoelectric actuator drive circuit of the pump so that, for each of plural points within a period of the waveform, the drive signal has an appropriate amplitude for a predetermined waveform shape (e.g., a waveform shape optimized for the pump). The waveform shape data is stored in a memory (such as table memory 212 of FIG. 13), and can be conveyed to a piezoelectric actuator drive circuit in modes such as those illustrated by event 14-3A, 14-3B, and 14-3C of FIG. 14. The waveform shape data may take the form of amplitude values, e.g., amplitude values which are paired with the plural points of the waveform period as in the manner of table 140-18A of FIG. 18A. Alternatively or additionally, the waveform shape data may take the form of pulse width modulation values which are paired with the plural points of the waveform period, for example in the manner of table 140-18B of FIG. 18B.

Any suitable basic waveform equation can be utilized by waveform optimizer 200, e.g., sine wave, square wave, rectangular wave, etc. In a non-limiting example mode now discussed, the fundamental wave equation having the general form of Equation 1 is utilized.

$$V = D \cdot \sum_{i=0}^{N-1} (A_i \sin(2\pi \cdot f \cdot t) + B_i \cos(2\pi \cdot f \cdot t)) \quad \text{Equation 1}$$

In Equation 1, D is the drive amplitude in volts; f is the operating frequency in Hz; N is the number of harmonics to be considered; and i=0, . . . N−1 is the index range for the harmonics.

As mentioned above and explained in more detail below, the coefficients $A_i$ and $B_i$ of the waveform equation of Equation 1 are first determined, after which the waveform equation is solved for its amplitude (voltage) V. In Equation 1, for the coefficients $A_i$ and $B_i$ the subscript i is respectively associated with the sine term and the cosine term of the fundamental term pair (when i=0) and harmonic term pairs (terms in which i>0).

Step 17-2 through step 17-4 involve initialization operations for various variables utilized in the waveform optimization procedure. These initialization operations are performed preparatory to invocation of a coefficient determination routine having example steps illustrated in FIG. 17C. The coefficient determination routine involves execution of an outer loop in which a harmonic pair counter for the coefficients, also known as a coefficient subscript counter i, is incremented as further harmonic terms are added to the waveform equation. Therefore, as step 17-2, the coefficient subscript counter i is initialized at zero. Moreover, the determination of each coefficient as preformed by the coefficient determination routine involves increasing or decreasing the magnitude of the coefficient by a certain value step_size. Accordingly, as step 17-3, an initial step_size (e.g., 0.2) is chosen. Further, although the coefficient determination routine determines coefficients of the waveform equation for both the sine and cosine terms pair of a harmonic pair of terms, only one term (the "active" term) has its coefficient determined at any given time. Therefore, as step 17-4 the sine term is set as the first active term (e.g., active_term=sine).

As mentioned above, the waveform optimization procedure can produce waveform shape data that is optimized in accordance with one or more operational parameters (e.g., operational criteria). For one or more of these operational parameters there may be certain boundary conditions within which the pump must operate. For example, if fluid flow is such an operational parameter, the operation of the pump may be acceptable only within a certain range of flow values. Therefore, optional step 17-5 involves inputting boundary conditions for the waveform optimization procedure. For example, at step 17-5 an upper fluid flow rate and/or a lower fluid flow rate may be input to the waveform optimization procedure.

A forthcoming step 17-10 involves execution of the coefficient determination routine for determining the coefficients of the waveform equation. As a precursor, nominal preliminary values for the coefficients $A_i$ and $B_i$ of the waveform equation are obtained at step 17-7. In one example implementation, these nominal preliminary values for the coefficients $A_i$ and $B_i$ are preferably stored in non-volatile memory. Then, using these nominal preliminary values for the coefficients $A_i$ and $B_i$ of the waveform equation, the waveform equation is utilized by waveform optimizer 200 at step 17-8 to generate a drive signal which is applied on line 204 to the piezoelectric actuator of the operative pump. As indicated by step 17-9, the waveform optimization program 210 waits a (preferably predetermined) settling time before continuing further operation. The settling time depends on the field of employment of the pump but may be, for example, on the order of twenty seconds. After expiration of the settling time, as indicated by symbol 17-10 the waveform optimization program 210 continues execution with the steps shown in FIG. 17B.

Figure 17:
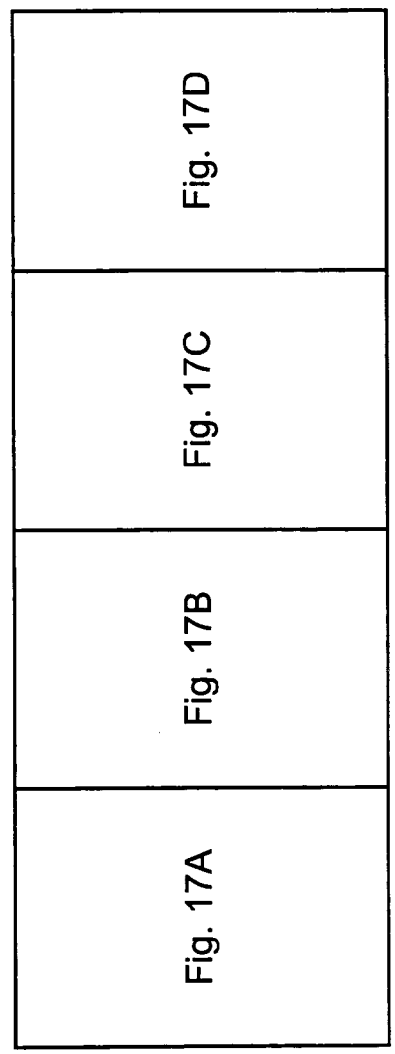
FIG. 17 is a diagrammatic view showing a relation of FIG. 17A-FIG. 17D.
Figure 17A:
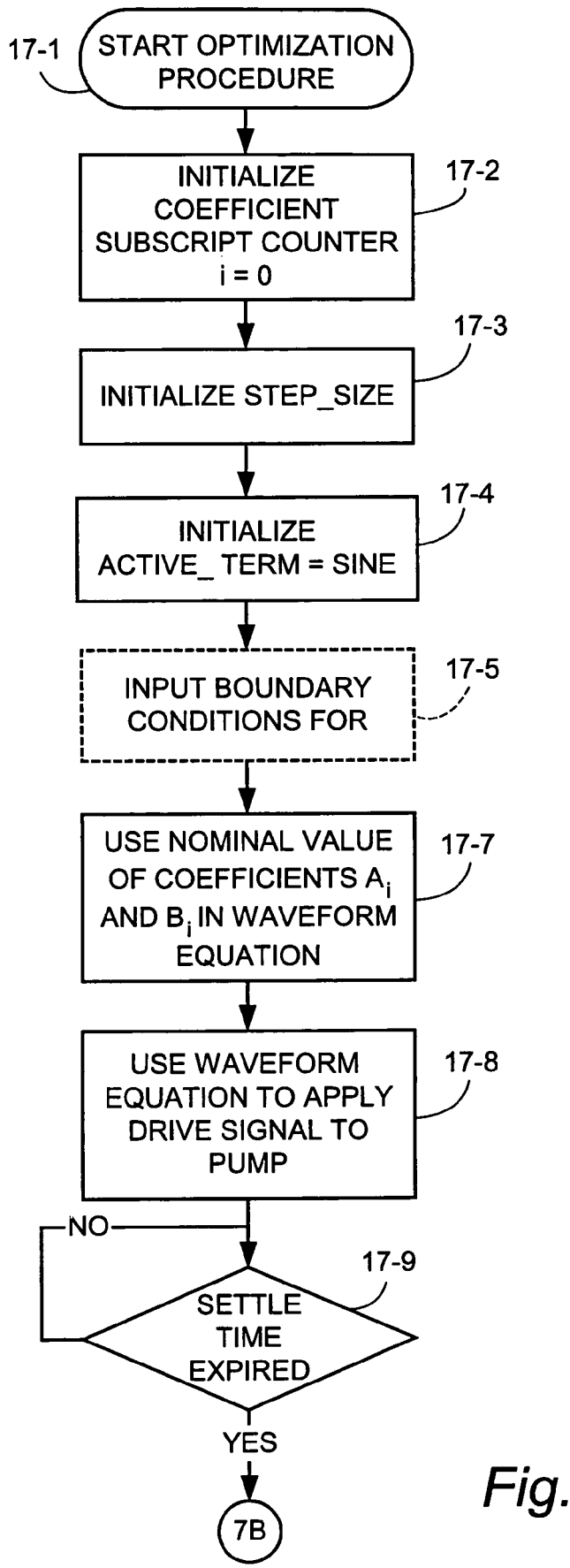
FIG. 17A–FIG. 17D are flowcharts which depict basic example steps performed in a waveform optimization procedure.
Figure 17B:
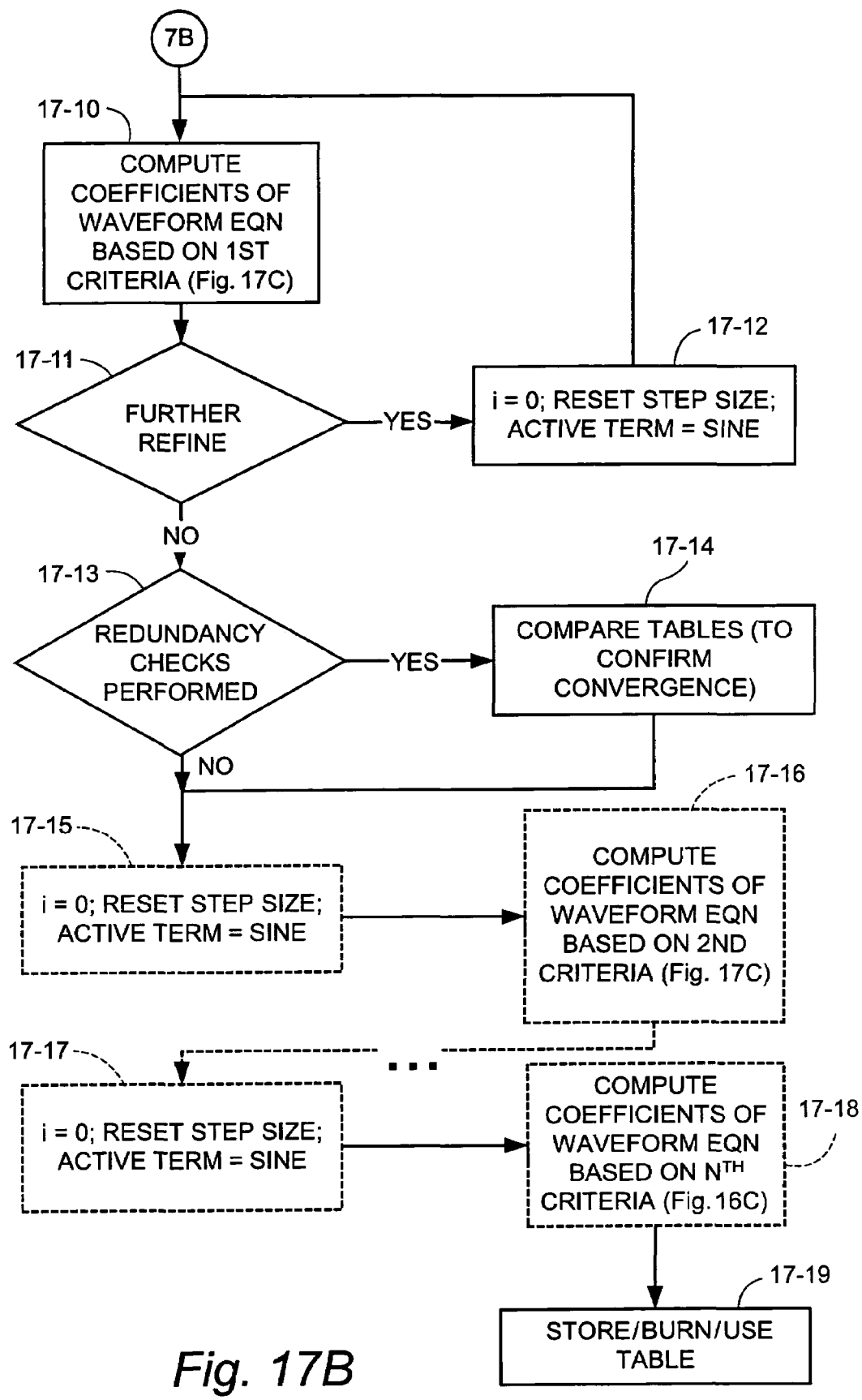

As step 17-10 of FIG. 17B, the coefficients of the waveform equation are computed based on a first operational criteria. This step 17-10 essentially involves invoking the coefficient determination routine having the sub-steps shown in FIG. 17C. As subsequently explained, the performance of the coefficient determination routine of FIG. 17C calls a table generation routine (shown in FIG. 17D), which ultimately results in generation of a table of waveform shape data (such as table 212 of FIG. 13).

After the coefficient determination routine of step 17-10 has determined all coefficients for the waveform equation, e.g., all harmonic term pairs, at step 17-11 the waveform optimization program 210 provides an opportunity to further refine the coefficients. In particular, starting from and building on the coefficients determined at step 17-10, the waveform optimizer continues to operate by essentially repeating step 17-10. Before so doing, at step 17-12 the appropriate counters and values are reset or reinitialized. For example, the coefficient subscript counter is reinitialized at zero, the value of step_size again reset, and active_term set to point to the sine term. The waveform optimizer may loop back to repeat step 17-10 several times, each time using the coefficients calculated during the last loop as the starting coefficients for the successive loop. For example, the loop may be repeated such that step 17-10 is performed three times based on the first criteria.

In addition to refinement, as an option the waveform optimizer also provides an opportunity for redundancy check. That is, after making a first determination of waveform coefficients with respect to a first criteria, at step 17-13 the waveform optimizer can start all over again with newly initialized coefficients, performing step 17-10 one or more times in order to check whether the redundancy-initiated performance(s) of step 17-10 yielded comparable coefficients as the original performance(s) of step 17-10. The redundancy check of step 17-13 can involve using the same basic waveform equation, or another waveform equation. The redundancy check of step 17-11 can be performed as many times as desired. Although not so illustrated, it will be appreciated that, prior to repeating the coefficient determination routine of step 17-10, in like manner as step 17-12 the appropriate counters and values are reset or reinitialized. If redundancy checks have been performed (as determined at step 17-13), there will be plural versions of tables of waveform shape data prepared by the coefficient determination routine of FIG. 17C (one version for each execution of the coefficient determination routine). Step 17-14 involves comparing the plural versions to confirm a similar convergence of the coefficients in both tables. If confirmation is not obtained by the comparison, appropriate measures can be taken (e.g., further repetition of the coefficient determination routine, or majority voting, or implementation of predetermined logic to accept one or the other tables).

As indicated above, in some applications and/or modes of operation the waveform optimization program 210 may optimize the waveform shape data based on only one operational parameter (e.g., only one criteria). On the other hand, in other applications and/or modes of operation the waveform optimization program 210 may optimize the waveform shape data based on plural operational parameter (e.g., more than one criteria). The series of steps of FIG. 17B labeled as step 17-15 through step 17-18 can be executed when optimization is based on or takes into consideration plural operational criteria. Since these plural criteria steps are optional (e.g., may not be performed for modes which optimized for only one operation parameter), these steps are shown as being framed with broken lines.

In the example, non-limiting implementation, should the waveform optimization program 210 perform its optimization based on plural operational criteria (e.g., multivariable optimization), the coefficients of the waveform equation are considered one at a time and in sequential fashion. For example, the coefficients of the waveform equation are first determined at step 17-10 with respect to the first operational parameter (first operational criteria, based e.g., on a first feedback signal) by a first execution of the coefficient determination routine. Then, after the first set of coefficients have been determined, those coefficients are utilized as a starting point for a second execution of the coefficient determination routine (at step 17-16) in which the second operational parameter influences coefficient determination (beased, e.g., on a second feedback signal). Similarly, if there are other operational criteria upon which the optimization is to be dependent, the most recently determined coefficients are utilized as a starting point for another execution of the coefficient determination routine (at step 17-18) in which the another operational parameter influences coefficient determination (based, e.g., on yet another feedback signal).

Of course, prior to each performance of the coefficient determination routine, the appropriate initializations and resets have to be made (e.g., i=0; step_size; active_term=sine). These initializations and resets are reflected by step 17-15 and step 17-17, which precede respective step 17-16 and step 17-18.

Other techniques are possible for performing waveform optimization when receiving plural criteria (e.g., receiving plural sensor input). As an alternative implementation, for example, a step such as step 17-10 can be performed with respect to one of the sensor/inputs (which is deemed a primary input). For example, the primary input might be flow in the pump. The waveform optimizer also keeps track of the signal(s) from other sensor(s), which are considered as secondary criteria. In particular, the waveform optimizer in this alternative implementation monitors to ensure that the input signal received for the secondary criteria sensor is within prescribed boundary values for the secondary criteria. So long as the input signal received for the secondary criteria sensor is within prescribed boundary values, the readings obtained for the primary sensor are validated and used to compute waveform coefficients. However, at any time that the input for the secondary sensor is outside of its boundary conditions, the primary input signals are discarded and therefore not used in the coefficient calculation. Therefore, only data collected when all of the plural sensor inputs are within boundary conditions is used for calculating the waveform coefficients based on the primary input.

Figure 17C:
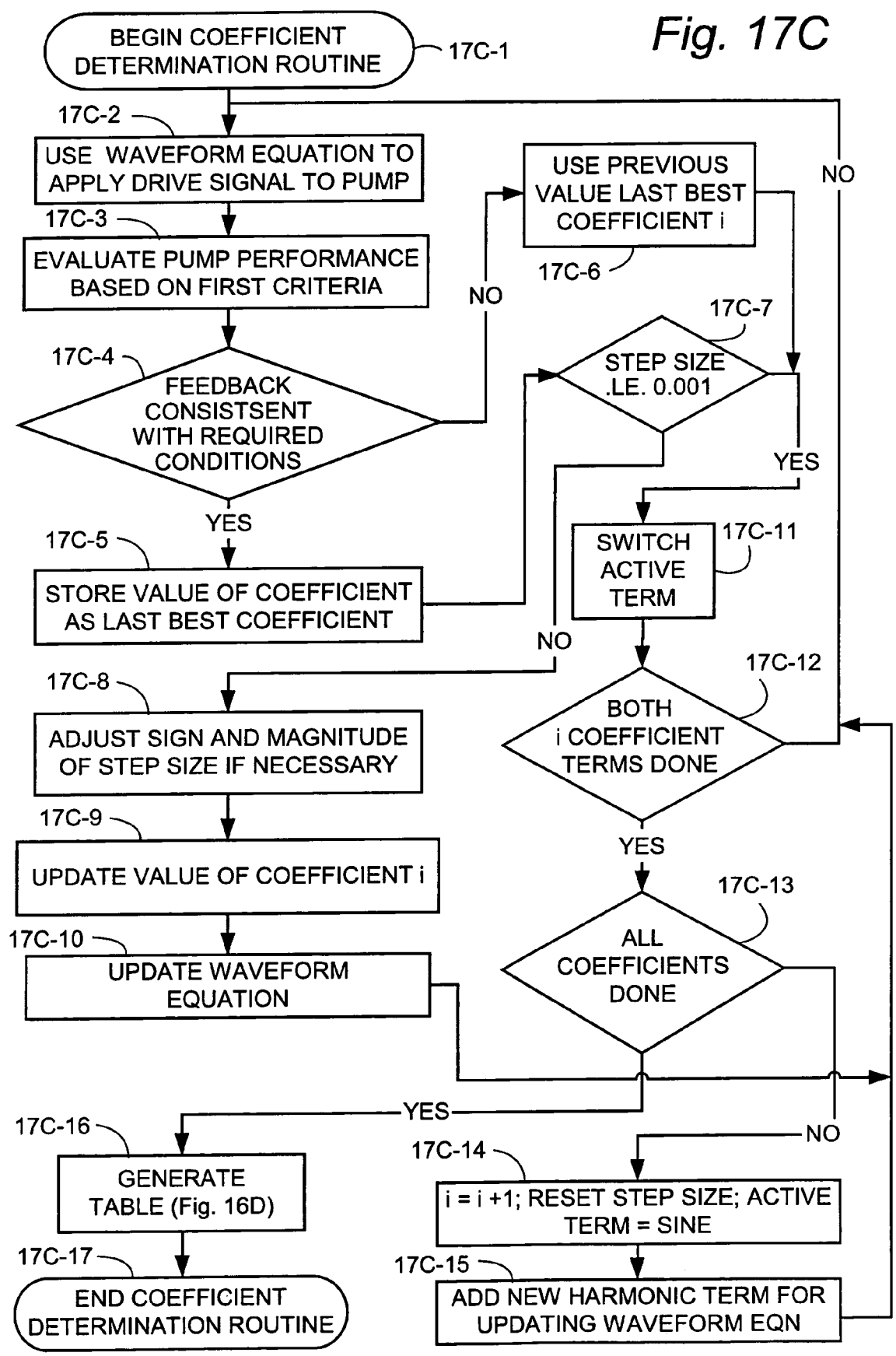
Figure 17D:
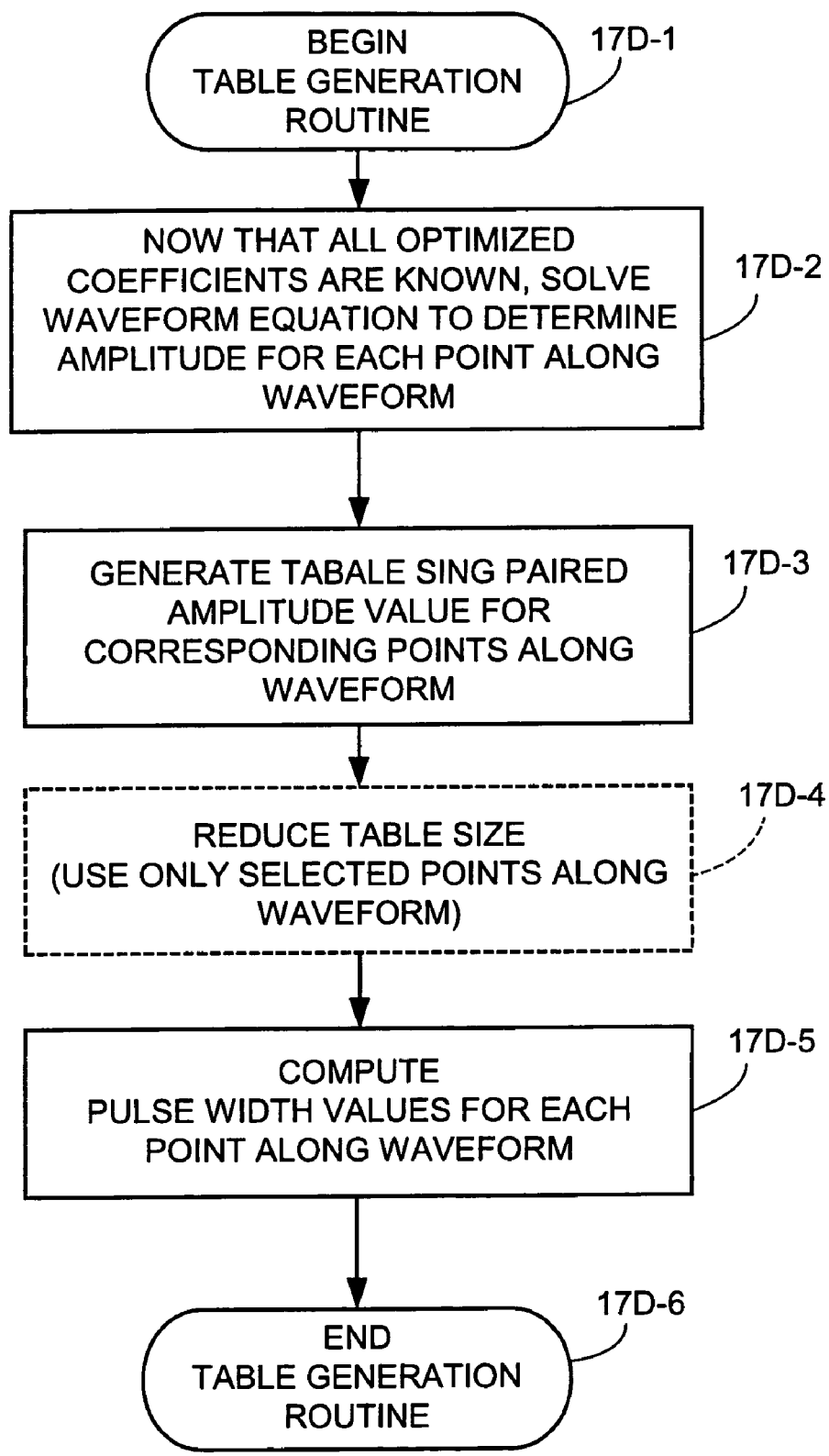

After as few or as many operational parameters as necessary have been considered, and the final coefficients determined, the table generation routine of FIG. 17D includes the final waveform shape data. As step 17-19, the final waveform shape data is stored or burned in table 212.

While in the preceding example discussion the plural operational criteria were considered essentially sequentially in determining the coefficients, it should be understood that, in other embodiments, the coefficients of the waveform equation can be determined while essentially simultaneously considering all operational criteria.

10.3.1 Coefficient Determination Routine

Basic steps involved in an example scenario of the coefficient determination routine are illustrated in FIG. 17C. As indicated previously, the coefficient determination routine is called whenever the waveform optimization procedure of waveform optimization program 210 is ready to determine coefficients of the waveform equation. For example, in the example logic of the waveform optimization procedure of FIG. 17A and FIG. 17B, when the coefficients of the waveform equation are to be determined for optimizing the waveform shape data according to a first operational criteria, the coefficient determination routine is called at step 17-10. Moreover, in the example logic of the waveform optimization procedure of FIG. 17A and FIG. 17B, when the waveform shape data is to be optimized in dependency upon plural operational criteria for the pump, the coefficient determination routine may subsequently be called for each of the plural operational criteria, as at example step 17-16 and example step 17-18 in FIG. 17B.

As evident from the ensuing discussion, the coefficient determination routine comprises an inner loop of steps which is nested within an outer loop of steps. The outer loop of steps increments the coefficient subscripter counter i. That is, in a first execution of the outer loop, the inner loop is repetitively executed, as many times as necessary, to determine both the coefficient $A_0$ for the sine term and the coefficient $B_0$ for the cosine term for the fundamental pair of terms of the waveform equation. During a second execution of the outer loop, the inner loop is repetitively executed, as many times as necessary, to determine both the coefficient $A_1$ for the sine term and the coefficient $B_1$ for the cosine term for the first harmonic pair of terms of the waveform equation. Similarly, during a third execution of the outer loop, the inner loop is repetitively executed, as many times as necessary, to determine both the coefficient $A_2$ for the sine term and the coefficient $B_2$ for the cosine term for the second harmonic pair of terms of the waveform equation, and so forth.

The inner loop of steps is repetitively executed, as many times as necessary, for determining an optimized coefficient value for a single term of the waveform equation. For a given pair of terms of the waveform equation (e.g., either the fundamental pair of terms or a harmonic pair of terms), the inner loop is first executed as many times as necessary (while active_term=sine) to find an optimal coefficient for the sine term. After the optimal coefficient for the sine term is determined, the active_term is switched (to active_term=cosine) so that the inner loop is executed as many times as necessary to find an optimal coefficient for the cosine term. Thus, the coefficient being determined at any given moment is determined by the active_term variable (which indicates either the sine or the cosine term), and the coefficient subscript counter i (which indicates to which pair of terms the term belongs: either to the fundamental pair of terms (i=0) or to one of the harmonic pairs of terms (i>0).

The commencement of the coefficient determination routine is indicated by step 17C-1. After the coefficient determination routine is initiated, as step 17C-2 the currently existing version of the waveform equation is used to apply a drive signal to the piezoelectric actuator 14 of the operational pump connected to waveform optimizer 200. Thereafter, e.g., possibly after a time delay, as step 17C-3 the coefficient determination routine evaluates the feedback signal received from the pump. For example, if the criteria of interest for this execution of the coefficient determination routine is fluid flow in the pump, then as step 17C-3 the sensor signal from the flowmeter is evaluated.

In conjunction with the evaluation, as step 17C-4 the coefficient determination routine determines if the feedback signal from the criteria sensor is consistent with required conditions for that criteria. For example, if the feedback signal is fluid flow, the logic of step 17C-3 may determine whether the fluid flow through the pump continues to increase (as is desired), or whether the fluid flow undesirably decreases. If the feedback is consistent with the required conditions (e.g., if the fluid flow continues to increase), then as step 17C-5 the current value of the coefficient being determined is stored as the latest best coefficient. On the other hand, if the feedback is inconsistent with the required conditions (e.g., if the fluid flow decreases rather than increases), then the coefficient determination routine knows that it has stepped too far in attempting to determine the coefficient, and accordingly as step 17C-6 the coefficient determination routine settles for using the latest best coefficient value for coefficient subscript i.

The feedback consistency check of step 17C-4 has been described with reference to the one operational criteria in view of which the waveform optimization program 210 is currently attempting to optimize the coefficients, and thus the waveform shape data. It should be understood that the feedback consistency check of step 17C-4 may also involve checks with respect to any other operational criteria for which the waveform optimizer 200 may also be requested to optimize the waveform shape data. For example, while checking at step 17C-4 to ensure that the signal from the flowmeter indicates that the fluid flow through the pump is increasing, the check at step 17C-4 may also involve determining that a feedback signal or sensor signal with respect to another operational parameter (e.g., operational criteria) is within boundary conditions for that other parameter/criteria. As an illustration, consider an example embodiment in which the waveform shape data is to be optimized not only in view of fluid flow but also fluid temperature. In such illustration, a second check performed at step 17C-4 may be to ensure that the signal indicative of temperature in the pump chamber is within boundary conditions (e.g., either above or below a predetermined temperature, or between a first predetermined temperature and a second predetermined temperature).

If it is determined at step 17C-4 that the feedback signal from the criteria sensor is consistent with required conditions for that criteria, after step 17C-5 a check is made whether the value of step_size is less than or equal to a predetermined value. In the illustrated mode, the predetermined smallest value of step_size which is utilized by the coefficient determination routine is 0.001.

If the variable step_size has not reached its predetermined smallest value, then further iterations of the inner loop of the coefficient determination routine are necessary for optimizing the coefficient. In preparation for further executions of the inner loop for the same coefficient, step 17C-8 through step 17C-10 are performed. At step 17C-8, the sign and magnitude of the variable step_size are adjusted (e.g., decremented to a smaller value). This is done for reducing the step_size as the coefficient determination routine gets closer and closer to the optimized value for the coefficient currently being handled. In one example implementation, at step 17C-8 the value of step_size is halved. At step 17C-9 an new coefficient value for the term currently being handled by coefficient determination routine is computed by adding the value of the variable step_size (as just computed at step 17C-8) to the latest best coefficient value for the current term. Then, as step 17C-10, the waveform equation is updated to that coefficient of the term currently being handled by the coefficient determination routine has the value just determined at step 17C-9. Thereafter, the inner loop is repeated (branching back to step 17C-2) so that the waveform equation as updated at step 17C-10 is used to apply the drive signal to the pump.

Should it be determined at step 17C-7 that the variable step_size has reached its predetermined smallest value, then no further iterations of the inner loop of the coefficient determination routine are necessary for optimizing the coefficient. At this point, the optimized value of the coefficient for the term currently being handled by the coefficient determination routine has been determined, at least with respect to the operational criteria for which optimization is now being performed. As such, the coefficient determination routine is now ready to determine a coefficient for the next term of the waveform equation, and continues with step 17C-11.

The value of the variable step_size reaching its predetermined smallest value is just one way in which the coefficient determination routine may realize that it is finished with determining a coefficient for a particular term. The coefficient determination routine can also realize that it has determined the optimum coefficient (at least for the current criteria) when the required conditions check of step 17C-4 is not satisfied. When the check of step 17C-4 fails (e.g., the fluid flow starts to decrease rather than increase), the coefficient determination routine realizes that it has gone too far in its increasing of the value of the coefficient. Accordingly, in such case as step 17C-6 the coefficient determination routine uses the latest best value of the coefficient (as determined at a previous execution of step 17C-5) as the coefficient for the term currently being handled. Thereafter the coefficient determination routine continues with step 17C-11.

Step 17C-11 is preformed when the coefficient determination routine realizes that it has just found the optimum coefficient for the criteria currently being optimized. The coefficient determination routine is now ready to execute the inner loop (as many times as necessary) for the next term of the waveform equation. If the term just processed was sine, then the next term will be cosine, and vise versa. For this reason, as step 17C-11 the coefficient determination routine switches the active_term variable (e.g., either from sine to cosine, or from cosine to sine).

As step 17C-12 the coefficient determination routine ascertains whether coefficients for both the sine term and the cosine term for a given term pair have been completed. If the coefficient subscript i is zero, then as step 17C-12 the coefficient determination routine checks whether coefficient $A_0$ for the sine term and the coefficient $B_0$ for the cosine term for the fundamental term pair have been completed. Or if the coefficient subscript i is one, then as step 17C-12 the coefficient determination routine checks whether coefficient $A_1$ for the sine term and the coefficient $B_1$ for the cosine term for the first harmonic term pair have been completed. If both coefficients for a given term pair have not been processed, execution loops back to step 17C-2 so that the inner loop can be repetitively performed as necessary for determining the coefficient for the cosine term of the term pair.

When it has been determined at step 17C-12 that the optimum coefficients for both the sine term and the cosine term of a given term pair have been determined, a further check is made at step 17C-13 whether all term pairs have been processed. In other words, step 17C-13 determines whether the value of the coefficient subscript counter equals the maximum number of harmonics for which the waveform equation is being optimized. In an illustrated embodiment, seven harmonics of the waveform equation are considered to be within the bandwidth of the pump, for which reason the coefficient determination routine realizes that it has found all coefficients for all term pairs when the check at step 17C-13 indicates that i=7.

When (as determined at step 17C-13) there remain other term pairs for which coefficients need be determined, the outer loop of the coefficient determination routine is again entered. In this regard, as step 17C-14 various re-initializations and re-settings occurs. For example, the value of the coefficient subscript counter is incremented (e.g., i=i+1); the value of step_size is again reset to its initial value; and active_term=sine). As step 17C-15, a new pair of terms for a new harmonic is added to the waveform equation. Thereafter the outer loop again initiates the inner loop, this time for the new harmonic term pair, by branching back to step 17C-2.

When (as determined at step 17C-13) the optimum values for coefficients for all term pairs of the waveform equation have been determined (at least with respect to the currently considered operational criteria), as step 17C-16 the table generation routine of FIG. 17D is performed. After the table generation routine of FIG. 17D has been completed and a version of a table such as the table 212-18A of FIG. 18A or the table 212-18B of FIG. 18B has been generated for this execution of coefficient determination routine, the coefficient determination routine is exited as indicated by step 17C-17.

10.3.2 Table Generation Routine

The table generation routine of FIG. 17D is invoked whenever one of several possible executions of the coefficient determination routine (see FIG. 17C) determines that it has determined optimum coefficients for the waveform equation (at least with respect to the operational criteria for which the coefficient determination routine was invoked). In the example logic of the coefficient determination routine of FIG. 17C, the table generation routine is invoked as step 17C-16.

Entry into the table generation routine is depicted as step 17D-1. At this point, all optimized coefficients for the waveform equation as determined on the optimized criteria are known. As step 17D-2, the waveform optimization program 210 executed by waveform optimizer 200 solves or evaluates the waveform equation (the waveform equation now having the known optimized coefficients) for each point along the waveform, in order to determine an amplitude (e.g., voltage V) for each point along the waveform. Since the waveform period is taken as 360 degrees, the points along the waveform are taken as degrees (or should the number of points be sufficiently great, as fractions of degrees). In the example sinusoidal waveform of FIG. 12, each point $X_1$, $X_2$, . . . , etc., corresponds to a degree or a fraction of a degree of one period, with each point X the waveform having a corresponding (voltage) amplitude V.

As step 17D-3, the table generation routine builds an initial table using the amplitude values determined at step 17D-2. An example such table has a format generally similar to that of table 212-18A illustrated in FIG. 18A, with amplitude values V being paired with corresponding period points X along the waveform.

In one implementation, the number of points X for which the waveform equation is evaluated at step 17D-2 may be over one thousand (e.g., ten thousand or even twenty thousand). As a practical matter, however, values for a much smaller number of points are really necessary. Accordingly, as optional step 17D-4, the size of the table generated at step 17D-3 may be reduced by using only selected (preferably evenly spaced) points along the waveform. For example, if the table generated at step 17D-3 has a size of twenty thousand points, the table size may be reduce by utilizing only every one thousandth point along the waveform.

As another optional but preferably action, as step 17D-5 the table generation routine can also include, in the table which it generates, the pulse width modulation values for each of the points $X_1$, $X_2$, etc., which yield the desired respective amplitudes and hence the desired overall waveform. An example format of such a table is illustrated by table 140-18B of FIG. 18B. In this implementation, the table 140-18B provides the pulse width for the signals PWM-A and PWM-B on line 124 and 126 (to be utilized by the piezoelectric actuator drive circuit 18 for the target pump) at selected intervals or points along the waveform through it period P.

After the table generation routine of FIG. 17D has completed generation of its table, the table generation routine is exited as indicated by step 17D-6. If the table so generated remains as the last version of the table upon completion of the waveform optimization program 210 of FIG. 17A and FIG. 17B, as step 17-19 the table is appropriate stored, burned, or utilized. In other words, the table is stored or utilized consistent with the chosen conveyance mode for conveying of the waveform shape data stored therein to the target piezoelectric actuator drive circuit for the target pump.

11.0 Drive Circuit: Scheduling Dose Delivery

The internal clock system of microcontroller 116 is used both (1) to generate the signal PWM-A and signal PWM-B for the flyback circuit 102 and (2) to control the applied field reversal. These signals are entirely under software control and thus, the drive amplitude and frequency can be manipulated in real-time and in an unlimited number of ways. For example, a piezoelectric pump can be driven in a traditional fashion of (for example) 400 volts at 60 Hz to produce a continuous flow, or it can be driven in an entirely unconventional and much more complex fashion of say 60 Hz for 1/30 of a second (1 pump "stroke") at 400 volts every 1 minute to reliably deliver a drop of medication to a patient on schedule. Such unconventional operation can be initiated by delivery scheduler 160, described in conjunction with FIG. 3H(1) and FIG. 3H(2). For such example, the drive circuit changes dynamically the drive signal whereby the drive signal varies over time so that an essentially non-continuous dosage of fluid is delivered by the pump.

In low-flow applications the pump may be driven at extremely slow frequencies (i.e. 1 stroke per minute). The circuit allows for the flyback generation to be interrupted at any time in a way that the pump will electrically "float" for a period of time, holding its position at any point in the mechanical pump stroke cycle. Thus, the micro can float the transducer and go to sleep for a period, knowing that the pump will remain at its last position until flyback generation resumes. This allows for extremely low power consumption in low-flow applications. Extremely long "float" periods can be achieved through slight circuit modifications.

Furthermore, the precise timing capabilities of the microcontroller and delivery scheduler 160 are further employed to control piezo actuators in certain applications in ways that are related to world clock time such as using a piezo pump to water a plant once a day.

12.0 Two-Way Communications with Drive Circuit

Non-volatile on-board memory also allows for each piezoelectric control circuit 18, or piezoelectric-actuated host (utilization) device to be serialized and uniquely identified. This aids in manufacturing quality control and is particularly important when actuators are employed in certain remote system applications. For 10 example, the communications channel 164 as shown in FIG. 3H(2) and communications interfaces can provide 2-way communications between one or more pumps and a controlling entity (e.g., remote unit 162). Via the serialization described above, each pump in a network can be individually controlled and any local parameters being monitored can be accessed by the system controller.

13.0 Epilogue

The piezoelectric actuator drive circuit 18, preferably but not exclusively embodied in the form of an electronic printed circuit board (PCB), steps a relatively low DC voltage up to a very high AC voltage operating at various frequencies to drive piezoelectric actuator 14. The piezoelectric actuator drive circuit 18 could also drive electromechanical devices other than pumps, such as (for example) oscillating fans, air compressors, speaker exciters, aerosolizers (e.g., ultrasonic agitators), actuators, active valves, precision actuators, to name a few. The piezoelectric actuator drive circuit 18 provides the necessary voltage and frequency to drive piezoelectric elements and other electromechanical devices, and advantageously has onboard capability to vary the voltages and frequencies necessary to optimize the efficiency of the piezoelectric actuator 14.

The piezoelectric actuator drive circuit 18 provides essentially total control over piezo/electromechanical devices in terms of voltage, frequency, waveform and feedback loops. The piezoelectric actuator drive circuit 18 eliminates the need for large testing and driving devices such as power amps, signal generators and oscilloscopes to test, evaluate and run piezoelectric devices. The feedback loops such as pressure and temperature allows the PDC to automatically set the proper frequency for efficient operation.

In a PWM servo mode of operation, the microcontroller 116 continuously monitors the voltage applied to the transducer and dynamically varies the PWM characteristics to regulate the applied voltage in a conventional switching power supply sort of way. Because the microcontroller 116 has access to elements of the pump drive environment-voltage, PWM duty, drive frequency—the load and/or efficiency of the actuator can be measured by correlating drive frequency to load. This is an extremely valuable capability in, for example, piezoelectric pumps. Using this capability the "resonant frequency" of a pump can be dynamically determined and it is anticipated that pump back pressure can be measured.

The piezoelectric actuator drive circuit 18 with its microcontroller 116 can monitor external local inputs such as that provided by adjustment potentiometers and temperature or pressure transducers or even something as simple as an on/off switch. These inputs can be used to control piezoelectric actuator 14 by controlling the drive signal applied thereto.

As described above, the micro has many available digital/analog I/O lines available. These can be used to monitor things such as temperature, pressure, diaphragm position, flow, etc. via either digital or analog sensor means. These inputs can then be used in the micro to control the pump via software in many ways. The inputs can also be fed back out to a controlling system via the 2-wire serial interface for system monitoring.

In accordance with one or more of its plural and distinct aspects, the piezoelectric actuator drive circuit 18 offers several advantages over the electroluminescent (EL) lamp driver and other circuits. Among these advantages, the piezoelectric actuator drive circuit 18 can provide, in accordance with a selected aspect thereof:

- An automatically seek of resonance frequency for the piezoelectric element (e.g., piezoelectric actuator 14), thereby ensuring optimum performance under varying pressures and flows.
- One or more feedback loops, thereby allowing for one or more sensors to provide sensed information (such as pressure and temperature) for influencing the drive signal and thus the driving waveform.
- Feedback directly from the piezoelectric element, thereby allowing a sensing of "work" being done by the piezoelectric element.
- A sleep mode for reducing power consumption and for remote sensing applications.
- Higher voltages than previously achievable by EL Lamp drivers.
- A variable drive signal waveform, thereby rendering the piezoelectric quieter and more efficient.
- Control of voltage and frequency trimmers/pots on the board rather than setting them through board components such as capacitors or resistors which cannot be changed in the field.
- Multiple drive electronics on a printed digital circuit, thereby allowing several piezoelectric elements to be driven at one time at the same voltage and frequency.
- A "syringe"-like mode, i.e., careful positioning of the piezoelectric element for highly precise flows.
- A "set and hold" feature to allow positioning a piezoelectric element at a full deflection position and holding it there to allow development of liquid piezoelectric valves.

In essence, the piezoelectric actuator drive circuit 18 allows the piezoelectric element (e.g., piezoelectric actuator 14) to operate at optimum efficiency and precision within the range of its operation at all times. This allows:

- piezoelectric pumps to be used for drug infusion which requires precision pumping
- more effective electronic cooling devices using liquid cooling rather than air (e.g., allowing computer manufacturers to operate processors at much higher frequencies than can currently be achieved with passive cooling thereby changing the face of the entire computer/electronics industries).
- piezo devices to be made smaller, lighter, and cheaper than ever before (e.g., for the computer industry).
- piezo pumps to be enabling technology for fuel cells.

Thus, piezoelectric actuator drive circuit 18 generates the required high-voltage, reversing actuator drive signal; drives piezoelectric elements or electromechanical devices at varying frequencies and voltages; provides means for monitoring many key parameters of the actuator and its environment; as well as receiving external inputs. In accordance with distinctly implementable aspects of piezoelectric actuator drive circuit 18, these parameters and inputs can be acted upon in real-time to control the piezoelectric actuator and optimize its performance. The operating characteristics of the piezoelectric actuator can be programmed into the microcontroller at any time, totally eliminating the "Mona Lisa" characteristics of existing architectures Further, drive circuits described herein have the capability to vary the frequency or voltage dynamically (e.g., after installed), and thereby facilitate optimization of frequency or voltage to address back pressures, temperatures and other operating conditions.

While the invention has been described in connection with what is presently considered to be the most practical and preferred embodiment, it is to be understood that the invention is not to be limited to the disclosed embodiment, but on the contrary, is intended to cover various modifications and equivalent arrangements included within the spirit and scope of the appended claims.

What is claimed is:

1. A method for determining a parameter for a piezoelectric actuator, the method comprising:
    applying a drive signal to the piezoelectric actuator;
    controlling the drive signal so that an ascertainable electrical charge is applied to the piezoelectric actuator;
    operating the piezoelectric actuator;
    obtaining a feedback signal from the piezoelectric actuator;
    obtaining a voltage value from the feedback signal;
    using the electrical charge and the voltage value from the feedback signal to determine capacitance of the piezoelectric actuator.

2. The method of claim 1 wherein the step of operating the piezoelectric actuator comprises using the piezoelectric actuator to pump fluid in a pump.

3. The method of claim 1, further comprising:
    deriving the drive signal from a pulse width modulated signal;
    controlling pulse widths of the pulse width modulated signal so that the ascertainable electrical charge is applied to the piezoelectric actuator.

4. The method of claim 1, further comprising subsequently using the capacitance of the piezoelectric actuator to control the drive signal to the piezoelectric actuator.

5. The method of claim 4, further comprising subsequently using the capacitance of the piezoelectric actuator to control pulse widths of a pulse width modulated signal from which the drive signal is derived.

6. A method for determining a parameter for a piezoelectric actuator, the method comprising:
    varying a drive signal applied to the piezoelectric actuator;
    operating the piezoelectric actuator;
    monitoring a feedback signal from the piezoelectric actuator as the drive signal is varied for an "echo";
    determining a resonant frequency of the piezoelectric actuator as an inverse of a period of the echo.

7. The method of claim 6, further comprising varying the drive signal through a step function.

8. A drive circuit for sensing capacitance of a piezoelectric actuator operating in a device and for adjusting a drive signal of the piezoelectric actuator in accordance with the capacitance, wherein the drive circuit comprises:
    a controller for controlling a drive signal applied to the piezoelectric actuator;
    a feedback monitor for obtaining a feedback signal from the piezoelectric actuator while the piezoelectric actuator operates;
    a processor for using the feedback signal to determine the capacitance of the piezoelectric actuator;
    wherein the controller controls the drive signal so that an ascertainable electrical charge is applied to the piezoelectric actuator; wherein the feedback monitor obtains a voltage value from the feedback signal; and wherein the processor uses the electrical charge and the voltage value from the feedback signal to determine the capacitance of the piezoelectric actuator.

9. The drive circuit of claim 8, wherein the device is a pump and wherein the piezoelectric actuator operates to pump fluid in the pump.

10. The apparatus of claim 8, wherein the drive circuit derives the drive signal from a pulse width modulated signal; and wherein the controller controls pulse widths of the pulse width modulated signal so that the ascertainable electrical charge is applied to the piezoelectric actuator.

11. The apparatus of claim 8, wherein the controller subsequently uses the capacitance of the piezoelectric actuator to control the drive signal to the piezoelectric actuator.

12. The apparatus of claim 11, wherein the controller subsequently uses the capacitance of the piezoelectric actuator to control pulse widths of a pulse width modulated signal from which the drive signal is derived.

13. A drive circuit for sensing a parameter of a piezoelectric actuator operating in a device and for adjusting a drive signal of the piezoelectric actuator in accordance with the parameter, wherein the drive circuit comprises:
 a controller for controlling a drive signal applied to the piezoelectric actuator;
 a feedback monitor for obtaining a feedback signal from the piezoelectric actuator while the piezoelectric actuator operates; wherein the feedback monitor obtains the feedback signal as the drive signal is varied for an "echo";
 a processor for using the feedback signal to determine the a resonant frequency of the piezoelectric actuator as an inverse of a period of the echo.

14. The apparatus of claim 13, wherein the controller varies the drive signal through a step function.

15. A drive circuit for sensing capacitance of a piezoelectric actuator operating in a device and for adjusting a drive signal of the piezoelectric actuator in accordance with the capacitance, wherein the drive circuit comprises:
 means for applying a drive signal to the piezoelectric actuator;
 means for obtaining a feedback signal from the piezoelectric actuator while the piezoelectric actuator operates;
 means for using the feedback signal to determine a capacitance of the piezoelectric actuator;
 wherein the means for applying controls the drive signal so that an ascertainable electrical charge is applied to the piezoelectric actuator; wherein means for obtaining obtains a voltage value from the feedback signal; and wherein the means for using uses the electrical charge and the voltage value from the feedback signal to determine the capacitance of the piezoelectric actuator.

16. The apparatus of claim 15, wherein the means for using determines the resonant frequency of the piezoelectric actuator as corresponding to the frequency in the range that had a minimum peak voltage value from the feedback signal.

17. A drive circuit for sensing a parameter of a piezoelectric actuator operating in a device and for adjusting a drive signal of the piezoelectric actuator in accordance with the parameter, wherein the drive circuit comprises:
 means for applying and varying a drive signal to the piezoelectric actuator;
 means for obtaining a feedback signal from the piezoelectric actuator while the piezoelectric actuator operates; wherein means for obtaining obtains the feedback signal as the drive signal is varied for an "echo";
 means for using the feedback signal to determine a resonant frequency of the piezoelectric actuator as an inverse of a period of the echo.

18. A piezoelectrically-actuated device comprising:
 a piezoelectric actuator which is responsive to a drive signal for pumping fluid between the inlet and outlet; and
 a drive circuit for sensing a capacitance of the piezoelectric actuator and for adjusting a drive signal of the piezoelectric actuator in accordance with the capacitance, wherein the drive circuit comprises:
 a controller for applying a drive signal to the piezoelectric actuator;
 a feedback monitor for obtaining a feedback signal from the piezoelectric actuator while the piezoelectric actuator operates;
 a processor for using the feedback signal to determine the capacitance of the piezoelectric actuator;
 wherein the controller controls the drive signal so that an ascertainable electrical charge is applied to the piezoelectric actuator; wherein the feedback monitor obtains a voltage value from the feedback signal; and wherein the processor uses the electrical charge and the voltage value from the feedback signal to determine the capacitance of the piezoelectric actuator.

19. The apparatus of claim 18, wherein the device is a pump having a pump body for at least partially defining a pumping chamber having an inlet and an outlet which communicate with the pumping chamber, and wherein the piezoelectric actuator pumps fluid between the inlet and outlet.

20. The apparatus of claim 18, wherein the drive circuit derives the drive signal from a pulse width modulated signal; and wherein the controller controls pulse widths of the pulse width modulated signal so that the ascertainable electrical charge is applied to the piezoelectric actuator.

21. The apparatus of claim 18, wherein the controller subsequently uses the capacitance of the piezoelectric actuator to control the drive signal to the piezoelectric actuator.

22. The apparatus of claim 21, wherein the controller subsequently uses the capacitance of the piezoelectric actuator to control pulse widths of a pulse width modulated signal from which the drive signal is derived.

23. The apparatus of claim 18, wherein the controller varies the drive signal through a range of excitation frequencies; and wherein the output monitor obtains a voltage value from the feedback signal for each of the excitation frequencies; and wherein the processor determines a resonant frequency of the piezoelectric actuator as corresponding to a frequency in the range that had a minimum voltage value from the feedback signal.

24. The apparatus of claim 23, wherein the processor determines the resonant frequency of the piezoelectric actuator as corresponding to the frequency in the range that had a minimum peak voltage value from the feedback signal.

25. A piezoelectrically-actuated device comprising:
 a piezoelectric actuator which is responsive to a drive signal for pumping fluid between the inlet and outlet; and
 a drive circuit for sensing a parameter of the piezoelectric actuator and for adjusting a drive signal of the piezoelectric actuator in accordance with the parameter, wherein the drive circuit comprises:

a controller for applying a drive signal to the piezoelectric actuator;

a feedback monitor for obtaining a feedback signal from the piezoelectric actuator while the piezoelectric actuator operates;

a processor for using the feedback signal to determine the parameter of the piezoelectric actuator;

wherein the controller varies the drive signal; wherein the feedback monitor obtains the feedback signal as the drive signal is varied for an "echo"; and wherein the processor determines a resonant frequency of the piezoelectric actuator as an inverse of a period of the echo.

26. The apparatus of claim 25, wherein the controller varies the drive signal through a step function.

* * * * *